US008771715B2

(12) United States Patent
Oslob et al.

(10) Patent No.: US 8,771,715 B2
(45) Date of Patent: Jul. 8, 2014

(54) COMPOSITIONS AND METHODS FOR TREATMENT

(75) Inventors: Johan Oslob, Sunnyvale, CA (US); Wang Shen, San Mateo, CA (US); Kenneth Barr, Boston, MA (US); Min Zhong, Palo Alto, CA (US)

(73) Assignee: Sarcode Bioscience Inc., Brisbane, CA (US)

(*) Notice: Subject to any disclaimer, the term of this patent is extended or adjusted under 35 U.S.C. 154(b) by 0 days.

(21) Appl. No.: 13/011,760

(22) Filed: Jan. 21, 2011

(65) Prior Publication Data

US 2011/0165228 A1 Jul. 7, 2011

Related U.S. Application Data

(63) Continuation of application No. 12/508,311, filed on Jul. 23, 2009, now abandoned, and a continuation of application No. 12/508,367, filed on Jul. 23, 2009, now Pat. No. 8,084,047, which is a continuation of application No. 11/436,906, filed on May 17, 2006, now Pat. No. 8,168,655, said application No. 12/508,311 is a continuation of application No. 11/436,906, filed on May 17, 2006, now Pat. No. 8,168,655.

(60) Provisional application No. 60/681,722, filed on May 17, 2005, provisional application No. 60/681,772, filed on May 17, 2005, provisional application No. 60/681,723, filed on May 17, 2005, provisional application No. 60/681,684, filed on May 17, 2005.

(51) Int. Cl.
*A61K 9/00* (2006.01)

(52) U.S. Cl.
USPC .......................................... 424/400; 514/912

(58) Field of Classification Search
USPC ................... 424/400; 514/912, 307
See application file for complete search history.

(56) References Cited

U.S. PATENT DOCUMENTS

| | | |
|---|---|---|
| 3,773,919 A | 11/1973 | Boswell et al. |
| 4,668,506 A | 5/1987 | Bawa |
| 4,713,244 A | 12/1987 | Bawa |
| 4,767,628 A | 8/1988 | Hutchinson |
| 4,908,202 A | 3/1990 | Schulz |
| 4,931,279 A | 6/1990 | Bawa et al. |
| 4,992,445 A | 2/1991 | Lawter et al. |
| 5,001,139 A | 3/1991 | Lawter et al. |
| 5,023,252 A | 6/1991 | Hseih |
| 5,134,122 A | 7/1992 | Orsolini |
| 5,149,780 A | 9/1992 | Plow et al. |
| 5,192,741 A | 3/1993 | Orsolini et al. |
| 5,236,704 A | 8/1993 | Fujioka et al. |
| 5,288,854 A | 2/1994 | Diamond et al. |
| 5,298,492 A | 3/1994 | Neustadt et al. |
| 5,340,800 A | 8/1994 | Liu et al. |
| 5,397,791 A | 3/1995 | Hartman et al. |
| 5,424,289 A | 6/1995 | Yang et al. |
| 5,424,399 A | 6/1995 | Arnaout |
| 5,445,832 A | 8/1995 | Orsolini et al. |
| 5,470,953 A | 11/1995 | Gallatin et al. |
| 5,585,359 A | 12/1996 | Breslin et al. |
| 5,597,567 A | 1/1997 | Whitcup et al. |
| 5,612,052 A | 3/1997 | Shalaby |
| 5,622,700 A * | 4/1997 | Jardieu et al. ............... 424/144.1 |
| 5,672,659 A | 9/1997 | Shalaby et al. |
| 5,747,035 A | 5/1998 | Presta et al. |
| 5,840,332 A | 11/1998 | Lerner et al. |
| 5,849,327 A | 12/1998 | Berliner et al. |
| 5,877,224 A | 3/1999 | Brocchini et al. |
| 5,893,985 A | 4/1999 | Luo et al. |
| 5,922,356 A | 7/1999 | Koseki et al. |
| 5,936,089 A | 8/1999 | Carpino et al. |
| 5,968,895 A | 10/1999 | Gefter et al. |
| 5,973,188 A | 10/1999 | Alig et al. |
| 5,980,945 A | 11/1999 | Ruiz |
| 6,180,608 B1 | 1/2001 | Gefter et al. |
| 6,204,280 B1 | 3/2001 | Gante et al. |
| 6,294,522 B1 | 9/2001 | Zablocki et al. |
| 6,331,640 B1 | 12/2001 | Fotouhi et al. |
| 6,340,679 B1 | 1/2002 | Peyman et al. |
| 6,358,976 B1 | 3/2002 | Wityak et al. |
| 6,515,124 B2 | 2/2003 | Fotouhi et al. |

(Continued)

FOREIGN PATENT DOCUMENTS

| | | |
|---|---|---|
| EP | 0314863 A2 | 5/1989 |
| EP | 0314863 A3 | 4/1990 |

(Continued)

OTHER PUBLICATIONS

Patani et al., Bioisosterism: A Rational Approach in Drug Design, Chem Rev, 1996, 3147-3176.*
Solomons, Fundamentals of Organic Chemistry, 1982, 5th Edition, p. 630.*
Gennaro et al., Remington: The Science and Practice of Pharmacy, 1995, 19th Edition, Mack Publishing Company, pp. xiv-xvi,1496-1503,1562-1567, 1588-1589,1598-1599,1672-1677.*
Lang, Ocular drug delivery conventional ocular formulations, Advanced Drug Delivery Reviews, 16 (1995) 39-43.*
Boschelli, et al. 3-Alkoxybenzo[b]thiophene-2-carboxamides as inhibitors of neutrophil-endothelial cell adhesion. J Med Chem. 1994; 37(6): 717-8.

(Continued)

Primary Examiner — Gigi Huang
(74) Attorney, Agent, or Firm — Troutman Sanders LLP

(57) ABSTRACT

The present invention provides compounds and methods for the treatment of LFA-1 mediated diseases. In particular, LFA-1 antagonists are described herein and these antagonists are used in the treatment of LFA-1 mediated diseases. One aspect of the invention provides for diagnosis of an LFA-1 mediated disease and administration of a LFA-1 antagonist, after the patient is diagnosed with a LFA-1 mediated disease. In some embodiments, the LFA-1 mediated diseases treated are dry eye disorders. Also provided herein are methods for identifying compounds which are LFA-1 antagonists.

19 Claims, 12 Drawing Sheets

(56) References Cited

U.S. PATENT DOCUMENTS

| | | |
|---|---|---|
| 6,524,581 B1 | 2/2003 | Adamis |
| 6,605,597 B1 | 8/2003 | Zablocki et al. |
| 6,620,422 B1 | 9/2003 | Maquin et al. |
| 6,642,225 B2 | 11/2003 | Albert et al. |
| 6,653,478 B2 | 11/2003 | Urbanski et al. |
| 6,667,060 B1 | 12/2003 | Vandecruys et al. |
| 6,667,318 B2 | 12/2003 | Burdick et al. |
| 6,670,321 B1 | 12/2003 | Adamis |
| 6,773,916 B1 | 8/2004 | Thiel et al. |
| 6,803,384 B2 | 10/2004 | Fotouhi et al. |
| 6,872,382 B1 | 3/2005 | Gamache et al. |
| 6,872,735 B2 | 3/2005 | Burdick et al. |
| 7,097,851 B1 | 8/2006 | Takada |
| 7,211,586 B2 | 5/2007 | Fenton et al. |
| 7,217,728 B2 | 5/2007 | Fotouhi et al. |
| 7,314,938 B2 * | 1/2008 | Shen et al. .................. 546/146 |
| 7,785,578 B2 | 8/2010 | Miller et al. |
| 7,989,626 B2 | 8/2011 | Shen et al. |
| 8,080,562 B2 | 12/2011 | Burnier et al. |
| 8,084,047 B2 | 12/2011 | Shen et al. |
| 2001/0031260 A1 | 10/2001 | Lee et al. |
| 2002/0019446 A1 | 2/2002 | Brocchini et al. |
| 2002/0115692 A1 | 8/2002 | Archibald et al. |
| 2002/0119994 A1 | 8/2002 | Burdick et al. |
| 2002/0132807 A1 | 9/2002 | Wang et al. |
| 2002/0176841 A1 | 11/2002 | Barker et al. |
| 2002/0177591 A1 | 11/2002 | O'Donnell et al. |
| 2003/0044406 A1 | 3/2003 | Dingivan |
| 2003/0064105 A1 | 4/2003 | Kim et al. |
| 2003/0068320 A1 | 4/2003 | Dingivan |
| 2003/0068384 A1 | 4/2003 | Brocchini et al. |
| 2003/0138488 A1 | 7/2003 | Kohn et al. |
| 2003/0166630 A1 | 9/2003 | Auvin et al. |
| 2003/0171296 A1 | 9/2003 | Gefter et al. |
| 2003/0216307 A1 | 11/2003 | Kohn et al. |
| 2004/0006236 A1 | 1/2004 | Fotouhi et al. |
| 2004/0028648 A1 | 2/2004 | Adamis |
| 2004/0038973 A1 | 2/2004 | Nahra et al. |
| 2004/0058968 A1 | 3/2004 | Burdick et al. |
| 2004/0120960 A1 | 6/2004 | Jardieu et al. |
| 2004/0122047 A1 | 6/2004 | Fenton et al. |
| 2005/0080119 A1 | 4/2005 | Fotouhi et al. |
| 2005/0148588 A1 | 7/2005 | Burdick et al. |
| 2005/0267098 A1* | 12/2005 | Shen et al. ............... 514/212.07 |
| 2006/0281739 A1 | 12/2006 | Gadek et al. |
| 2007/0025990 A1 | 2/2007 | Dingivan |
| 2007/0155671 A1 | 7/2007 | Fotouhi et al. |
| 2008/0019977 A1 | 1/2008 | Adamis |
| 2008/0176896 A1 | 7/2008 | Shen et al. |
| 2008/0182839 A1 | 7/2008 | Shen et al. |
| 2009/0155176 A1 | 6/2009 | Burnier et al. |
| 2009/0258069 A1 | 10/2009 | Burnier et al. |
| 2009/0258070 A1 | 10/2009 | Burner et al. |
| 2009/0298869 A1 | 12/2009 | Burnier et al. |
| 2010/0092541 A1 | 4/2010 | Burnier et al. |
| 2010/0092542 A1 | 4/2010 | Burnier et al. |
| 2011/0092707 A1 | 4/2011 | Burnier et al. |
| 2011/0124669 A1 | 5/2011 | Shen et al. |
| 2011/0165229 A1 | 7/2011 | Burnier et al. |
| 2012/1017404 | 5/2012 | Burnier et al. |

FOREIGN PATENT DOCUMENTS

| | | |
|---|---|---|
| EP | 0362526 A2 | 4/1990 |
| EP | 0362531 A1 | 4/1990 |
| EP | 0362526 A3 | 7/1990 |
| EP | 0326151 B1 | 6/1993 |
| EP | 0656789 B1 | 12/1997 |
| EP | 0467389 B1 | 10/1999 |
| EP | 1392306 B1 | 1/2008 |
| JP | 4193895 | 7/1992 |
| WO | WO 90/03400 A1 | 4/1990 |
| WO | WO 90/10652 A1 | 9/1990 |
| WO | WO 90/13316 A1 | 11/1990 |
| WO | WO 91/19511 A1 | 12/1991 |
| WO | WO 92/03473 A1 | 3/1992 |
| WO | WO 93/16702 A1 | 9/1993 |
| WO | WO 93/24150 A1 | 12/1993 |
| WO | WO 94/03481 A1 | 2/1994 |
| WO | WO 94/11400 A1 | 5/1994 |
| WO | WO 94/15587 A2 | 7/1994 |
| WO | WO 94/15587 A3 | 9/1994 |
| WO | WO 95/04531 A1 | 2/1995 |
| WO | WO 95/28170 A1 | 10/1995 |
| WO | WO 96/09836 A1 | 4/1996 |
| WO | WO 97/04744 A1 | 2/1997 |
| WO | WO 97/26015 A1 | 7/1997 |
| WO | WO 97/40085 A2 | 10/1997 |
| WO | WO 97/40085 A3 | 1/1998 |
| WO | WO 98/13029 A1 | 4/1998 |
| WO | WO 98/25642 A2 | 6/1998 |
| WO | WO 98/25642 A3 | 7/1998 |
| WO | WO 98/46599 A1 | 10/1998 |
| WO | WO 99/49856 A2 | 10/1999 |
| WO | WO 99/49856 A3 | 11/1999 |
| WO | WO 00/21920 A1 | 4/2000 |
| WO | WO 00/38714 A1 | 7/2000 |
| WO | WO 00/44731 A1 | 8/2000 |
| WO | WO 01/01964 A2 | 1/2001 |
| WO | WO 01/12233 A2 | 2/2001 |
| WO | WO 01/27102 A1 | 4/2001 |
| WO | WO 01/01964 A3 | 6/2001 |
| WO | WO 01/49249 A2 | 7/2001 |
| WO | WO 01/49311 A1 | 7/2001 |
| WO | WO 01/58853 A1 | 8/2001 |
| WO | WO 01/12233 A3 | 11/2001 |
| WO | WO 01/87840 A1 | 11/2001 |
| WO | WO 01/49249 A3 | 1/2002 |
| WO | WO 02/30398 A2 | 4/2002 |
| WO | WO 02/38129 A2 | 5/2002 |
| WO | WO 02/50080 A1 | 6/2002 |
| WO | WO 02/058672 A2 | 8/2002 |
| WO | WO 02/059114 A1 | 8/2002 |
| WO | WO 02/074247 A2 | 9/2002 |
| WO | WO 02/058672 A3 | 12/2002 |
| WO | WO 02/074247 A3 | 12/2002 |
| WO | WO 02/098426 A1 | 12/2002 |
| WO | WO 02/38129 A3 | 2/2003 |
| WO | WO 02/30398 A3 | 3/2003 |
| WO | WO 03/053401 A2 | 7/2003 |
| WO | WO 03/075887 A1 | 9/2003 |
| WO | WO 03/053401 A3 | 1/2004 |
| WO | WO 2004/026406 A1 | 4/2004 |
| WO | WO 2005/014532 A1 | 2/2005 |
| WO | WO 2005/014533 A2 | 2/2005 |
| WO | WO 2005/014533 A3 | 4/2005 |
| WO | WO 2005/042710 A1 | 5/2005 |
| WO | WO 2005/044817 A1 | 5/2005 |
| WO | WO 2005/123706 A1 | 12/2005 |
| WO | WO 2006/125119 A1 | 11/2006 |
| WO | WO 2009/139817 A2 | 11/2009 |
| WO | WO 2009/139817 A3 | 1/2010 |

OTHER PUBLICATIONS

Boschelli, et al. Inhibition of E-Selectin-, ICAM-1-, and VCAM-1-mediated cell adhesion by benzo[b]thiophene-, benzufuran-, indole-, and naphthalene-2-carboxamides: Identification of PD 144795 as an antiinflammatory agent. J Med Chem. 1995; 38: 4597-614.

Burdick, et al. N-Benzoyl amino acids as ICAM/LFA-1 inhibitors. Part 2: Structure-activity relationship of the benzoyl moiety. Bioorganic & Medicinal Chemistry Letters. 2004; 14(9): 2055-9.

Burdick, et al. N-Benzoyl amino acids as LFA-1/ICAM inhibitors 1: amino acid structure-activity relationship. Bioorganic & Medicinal Chemistry Letters. 2004; 13(6): 1015-8.

Chang, et al. Effects of pharmacologic agents on the reversed passive Arthus reaction in the rat. Eur J Pharmacol. 1981; 69(2): 155-64.

Chavanpatil, et al. Novel sustained release, swellable and bioadhesive gastroretentive drug delivery system for ofloxacin. Int J Pharm. 2006; 316(1-2): 86-92.

Coleman, et al. Chemoselective Cleavage of Benzyl Ethers, Esters, and Carbamates in the Presence of Other Easily Reducible Groups. Synthesis. 1999;1399-1400.

(56) References Cited

OTHER PUBLICATIONS

Cosimi, et al. In vivo effects of monoclonal antibody to ICAM-1 (CD54) in nonhuman primates with renal allografts. J Immunol. 1990; 144(12): 4604-12.
Diamond, et al. The dynamic regulation of integrin adhesiveness. Current Biology. 1994; 4(6): 506-32.
European Office Action dated Nov. 9, 2010 for Application No. 6770607.7.
European search report dated May 20, 2009 for Application No. 06770607.7.
Fischer, et al. Prevention of graft failure by an anti-HLFA-1 monoclonal antibody in HLA-mismatched bone-marrow transplantation. The Lancet. 1986; 2: 1058-60.
Fox. Systemic diseases associated with dry eye. Int Ophthalmol Clin, 1994; 34(1):71-87.
Gadek, et al. Generation of an LFA-1 antagonist by the transfer of the ICAM-1 immunoregulatory epitope to a small molecule. Science. 2002; 295: 1086-9.
Gao, et al. ICAM-1 expression predisposes ocular tissues to immune-based inflammation in dry eye patients and Sjögrens syndrome-like MRL/lpr mice. Exp Eye Res. Apr. 2004;78(4):823-35.
Gorski, A. The role of cell adhesion molecules in immunopathology. Immunology Today. 1994; 15: 251-5.
Hildreth, et al. Monoclonal antibodies against porcine LFA-1: Species cross-reactivity and functional effects of β-subunit-specific antibodies. Molecular Immunology. 1989; 26(9): 883-95.
Hoffman, et al. Pharmacokinetic and pharmacodynamic aspects of gastroretentive dosage forms. Int J Pharm. 2004; 277(1-2): 141-53.
Huang, et al. A binding interface of the I domain of lymphocyte function-associated antigen-1 (LFA-1) required for specific interaction with intercellular adhesion molecule 1 (ICAM-1). J Biological Chemistry. 1995; 270(32): 19008-16.
International search report dated Sep. 19, 2006 for PCT Application No. PCT/US2006/19327.
Kavanaugh, et al. Treatment of refractory rheumatoid arthritis with a monoclonal antibody to intercellular adhesion molecule 1. Arthritis Rheum. 1994; 37(7): 992-1004.
Keating, et al. Competition between intercellular adhesion molecule-1 and a small-molecule antagonist for a common binding site on the alpha1 subunit of lymphocyte function-associated antigen-1. Protein Sci. 2006; 15(2):290-303.
Keating, et al. Putting the pieces together : Contribution of fluorescence polarization assays to small molecule lead optimization. Proc. SPIE. 2000; vol. 3913, p. 128-137. (Online Publication Date: Jul. 2, 2003).
Kishimoto, et al. Integrins, ICAMs, and selectins: Role and regulation of adhesion molecules in neutrophil recruitment to inflammatory sites. Adv Pharmacol. 1994; 25: 117-69.
Klausner, et al. Novel gastroretentive dosage forms: evaluation of gastroretentivity and its effect on levodopa absorption in humans. Pharm Res. 2003; 20(9): 1466-73.
Kunert, et al. Analysis of Topical Cyclosporine Treatment of Patients with Dry Eye Syndrome. Arch Ophthalmol, vol. 118, Nov. 2000, 1489-1496.
Le Mauff, et al. Effect of anti-LFA1 (CD11a) monoclonal antibodies in acute rejection of human kidney transplantation. Transplantation. 1991; 52(2): 291-5.
Legarreta Eye Center, Dry Eye, Jan. 2002, printed from http://www.legarretaeyecenter.com/dry-eye.html with Google date entry, 3 pages.
Liu, G. Inhibitors of LFA-1/ICAM-1 interaction: from monoclonal antibodies to small molecules. Drugs of the Future. 2001; 26: 767-78.
Liu, G. Small molecule antagonists of the LFA-1/ICAM-1 interaction as potential therapeutic agents. Expert Opin Ther Patents. 2001; 11: 1383-93.
Lu, et al. The binding sites for competitive antagonistic, allosteric antagonistic, and agonistic antibodies to the I domain of the integrin LFA-1. J Immunol. 2004; 173: 3972-8.
Musza, et al. Potent new cell adhesion inhibitory compounds from the root of *Trichilia rubra*. Tetrahedron. 1994; 50(39): 11369-78.

Office Action dated Sep. 28, 2010 for U.S. Appl. No. 12/508,311.
Office Action dated Dec. 21, 2010 for U.S. Appl. No. 11/436,906.
Park, et al. Effects of fluorine substitution on drug metabolism: pharmacological and toxicological implications. Drug Metab Rev. 1994;26(3):605-43.
Park, et al. Metabolism of fluorine-containing drugs. Annu Rev Pharmacol Toxicol. 2001;41:443-70.
Plobeck, et al. New diarylmethylpiperazines as potent and selective nonpeptidic δ opioid receptor agonists with increased in vitro metabolic stability. J Med Chem. 2000; 43: 3878-94.
Rothlein, et al. 1. Leukocyte adhesion in inflammation: From discovery to the clinic. Adhesion Molecules. Wegner, C.D., Ed.; 1994: 1-8.
Salas, et al. Rolling adhesion through an extended conformation of integrin $\alpha L\beta 2$ and relation to $\alpha$ I and $\beta$ I-like domain interaction. Immunity. 2004; 20(4): 393-406.
Sanfilippo, et al. Novel thiazole based heterocycles as inhibitors of LFA-1/ICAM-1 mediated cell adhesion. J Med Chem. 1995; 38: 1057-9.
Shimaoka, et al. Reversibly locking a protein fold in an active conformation with a disulfide bond: Integrin alpha L I domains with high affinity and antagonist activity in vivo. PNAS. 2001; 98(11): 6009-14.
Shimaoka, et al. Small molecule integrin antagonists that bind to the β2 subunit I-like domain and activate signals in one direction and block them in the other. Immunity. 2003; 19(3): 391-402.
Shimaoka, et al. Structures of the αL I domain and its complex with ICAM-1 reveal a shape-shifting pathway for integrin regulation. Cell. 2003; 112(1): 99-111.
Shimaoka, et al. Therapeutic antagonists and the conformational regulation of the β2 integrins. Curr Topics Med Chem. 2004; 4: 1485-95.
Springer, T. Adhesion receptors of the immune system. Nature. 1990; 346: 425-34.
Stern, et al. Conjunctival T-cell subpopulations in Sjögren's and non-Sjögren's patients with dry eye. Invest Ophthalmol Vis Sci. Aug. 2002;43(8):2609-14.
Streubel, et al. Gastroretentive drug delivery systems. Expert Opin Drug Deliv. 2006; 3(2): 217-33.
The Eye Digest, Eye Exam for Dry Eyes, Mar. 2003, printed from http://www.agingeye.net/dryeyes/dryeeyeseyeexam.php and google date entry, 4 pages.
Welzenbach, et al. Small molecule inhibitors induce conformational changes in the I domain and the I-like domain of lymphocyte function-associated antigen-1. J Biological Chemistry. 2002; 277(12): 10590-8.
Wermuth, C. G. The practice of medicinal chemistry-molecular variations based on isosteric replacements. Academic Press Limited. 1996; 203, 226-228.
Office Action dated Sep. 28, 2010 for U.S. Appl. No. 12/508,367.
Zhong, et al. Discovery and Development of Potent LFA-1/ICAM-1 Antagonist SAR 1118 as an Ophthalmic Solution for Treating Dry Eye. ACS Med. Chem. Lett. DOI: 10.1021/ml2002482. Publication Date (Web): Jan. 31, 2012.
Crocker, et al. The role of fluorine substitution in the structure-activity relationships (SAR) of classical cannabinoids. Bioorg med chem lett. 2007; 17(6):1504-1507.
European office action dated Nov. 24, 2011 for Application No. 06770607.7.
Frishberg, et al. Cyclosporine A regulates T cell-epithelial cell adhesion by altering LFA-1 and ICAM-1 expression. Kidney Int. Jul. 1996;50(1):45-53.
Hecht, et al. Effects of methyl and fluorine substitution on the metabolic activation and tumorigenicity of polycyclic aromatic hydrocarbons. ACS Symposium series. 1985; 283(5):85-105. Abstract only.
Kunert, et al. Goblet cell numbers and epithelial proliferation in the conjunctiva of patients with dry eye syndrome treated with cyclosporine. Arch Ophthalmol. Mar. 2002;120(3):330-7.
Murphy, et al. The Pharmacologic Assessment of A Novel Lymphocyte Function-Associated Antigen-1 Antagonist (SAR 1118) for the Treatment of Keratoconjunctivitis Sicca in Dogs. Invest Ophthalmol Vis Sci. May 16, 2011;52(6):3174-80.
Office action dated Jun. 7, 2011 for U.S. Appl. No. 11/436,906.
Office action dated Jun. 8, 2011 for U.S. Appl. No. 12/508,367.

(56) References Cited

OTHER PUBLICATIONS

Office action dated Oct. 5, 2011 for U.S. Appl. No. 13/011,775.
U.S. Appl. No. 13/398,542, filed Feb. 16, 2012, Gadek et al.
European office action dated Mar. 28, 2012 for Application No. 11181066.9.
Davies et al. Physiological Parameters in Laboratory Animals and Humans. Pharmaceutical Research. 1993;10:1093-1095.
Earle et al. A Simplified Clinical Procedure for Measurement of Glomerular Filtration Rate and Renal Plasma Flow. Froc. Soc. Exp. Biol. Med. 1946;62:262-269.
Ley, et al. Getting to the site of inflammation: the leukocyte adhesion cascade updated. Nat Rev Immunol. Sep. 2007;7(9):678-689.
Sapirstein et al. Volumes of Distribution and Clearances of Intravenously Injected Creatinine in the Dog. American Journal of Physiology. 1955; 181 :330-336.
Shulman, et al. Lymphocyte crawling and transendothelial migration require chemokine triggering of high-affinity LFA-1 integrin. Immunity. Mar. 20, 2009;30(3):384-396.
Ward, S. Millipede-like lymphocyte crawling: feeling the way with filopodia. Immunity. Mar. 20, 2009;30(3):315-317.
Goodman, et al. Amino acid active esters. III. Base-catalyzed racemization of peptide active ester. Journal of Organic Chemistry, 1962; 27:3409-3416.
Kaiser, et al. Hydrolysis-induced racemization of amino acids. Limnol. Oceanogr. Methods. 2005; 3:318-325.
International search report and written opinion dated Dec. 22, 2010 for PCT Application No. PCT/US2010/053571.
International search report and written opinion dated Sep. 24, 2009 for PCT Application No. PCT/US2009/002391.
Office action dated Jun. 25, 2012 for U.S. Appl. No. 12/909,241.
Paschides et al. Evaluation of tear break-up time, Schirmer's-I test and rose bengal staining as confirmatory tests for keratoconjunctivitis sicca, Clin Exp Rheumatol. 1989, 7(2), printed from http://www.ncbi.nlm.nih.gov/pubmed/2736828, Abstract only.
Lupus erythematorsus. Retrieved Dec. 28, 2006 from the internet URL: http://en.wikipedia.org/wiki/Lupus_erythematorsus.
Liebeskind, et al. Paraneoplastic encephalopyelitis. eMedicine. Updated Jun. 11, 2009, Available: http://emedicine.medscape.com/article/1157060. Accessed Dec. 29, 2009.
International Search Report dated Mar. 30, 2005, issued in International Application No. PCT/US2004/036942.

* cited by examiner

Interaction of LFA-1 Immunological Synapse Formation

Immunological Synapse Formation

Inhibition of Proper Immunological Synapse Formation via LFA-1 Inhibition

Compound 1, R = (C=S)NH-Fluorescein

Compound 2A, R = H
Compound 2B, R = (C=S)NH-Fluorescein

Compound 3

Compound 4

A-286982

Compound 5

Table 1. Cation dependence of the affinities of small molecule antagonists for LFA-1

| Antagonist | Divalent Cations | $K_i$ (nM) | $K_d$ (nM) |
|---|---|---|---|
| Compound 3 | $CaCl_2$ + $MgCl_2$ | 95 | |
| | $MnCl_2$ | 3.2 | |
| Compound 4 | $CaCl_2$ + $MgCl_2$ | 6.0 | |
| | $MnCl_2$ | 0.58 | |
| ICAM-1-Ig[1] | $CaCl_2$ + $MgCl_2$ | ~2700 | |
| | $MnCl_2$ | ~600 | |
| Compound 1 | $CaCl_2$ + $MgCl_2$ | | 24 |
| | $MnCl_2$ | | 0.77 |

FIGURE 5

COMPOSITIONS AND METHODS FOR TREATMENT

CROSS-REFERENCE

This application is a Continuation Application under 35 U.S.C. §120 of U.S. application Ser. No. 12/508,367, filed Jul. 23, 2009, issued as U.S. Pat. No. 8,084,047 on Dec. 27, 2011, and a Continuation Application under 35 U.S.C. §120 of U.S. application Ser. No. 12/508,311, filed Jul. 23, 2009, each of which is a Continuation Application under 35 U.S.C. §120 of U.S. application Ser. No. 11/436,906, filed May 17, 2006, issued as U.S. Pat. No. 8,168,655 on May 1, 2012; which claims the benefit under 35 U.S.C. §119(e) of U.S. Provisional Patent Application No. 60/681,684, filed May 17, 2005; U.S. Provisional Application No. 60/681,722, filed May 17, 2005; U.S. Provisional Application No. 60/681,772, filed May 17, 2005, and U.S. Provisional Application No. 60/681,723, filed May 17, 2005; each of which is incorporated herein by reference in its entirety.

BACKGROUND OF THE INVENTION

An ophthalmological disorder, dry eye, is a common complaint of ophthalmic patients. Unaddressed conditions of dry eye can lead to erosion and abrasion of the epithelial cell surface of the cornea, raising susceptibility to infection. Progression of the disease can lead to ulceration of the cornea, even loss of sight.

A variety of irritants, injuries, and medical conditions predispose individuals to initiation of decreased lacrimal gland secretion resulting in deficient levels of aqueous tears protecting and nourishing the surface of the eye. There are environmental factors such as high altitudes, and windy climates, air pollution, desiccated air from central heat and central air conditioning, and exposure to cigarette smoke which can establish and/or enhance deterioration of the quantity and quality of tear production. Even extensive computer use can be a contributing factor as studies have shown significantly decreased blinking rates for users concentrating their attention on computer screens. Some advances in eye care, starting with the introduction of contact lenses, and currently, the popularity of the LASIK procedure for vision correction, have contributed to the recent growth of subject numbers with dry eye. Use of contact lenses results in absorption of tear film by the lens, with resultant physical irritation of the conjunctiva in the eyelids. LASIK can have a secondary effect of eye injury as nerves often can be severed or ablated during laser refractive surgery, which can lead to at least temporary dry eye syndrome of several months duration.

Disease and some physical conditions can predispose individuals to dry eye disorder, including; allergies, diabetes, lacrimal gland deficiency, lupus, Parkinson's disease, Sjogren's syndrome, rheumatoid arthritis, rosacea, and others. Medications for other diseases may cause or exacerbate dry eye disorders, including diuretics, antidepressants, allergy medications, birth control pills, decongestants and others.

Age related changes may induce or exacerbate dry eye as well. Post menopausal women experience changes in hormonal levels that can instigate or worsen dry eye, and thyroid imbalances may cause similar changes. Finally, aging itself can cause a reduction in lipid production with resultant dry eye.

Until recently, therapeutic interventions were limited to palliative measures to increase the moisture level of the eye. This is most frequently achieved with instillation of fluids which act as artificial tears. These fluids are often solutions which are instilled once or several times a day. For more severe cases of dry eye, artificial tear solutions which incorporate a thickener or ocular gels can enhance the amount of film retained on the eye. Alternatively, several night-time ointment therapies are available. The thickened solutions, gels, and ointments suffer from the limitation that vision can be impaired significantly upon application, rendering them less useful to the average subject who may require numerous applications during their waking, active hours. Another palliative intervention is the installation of temporary punctal occlusions, or even surgical closure of the normal drainage route of tears into the nasal cavity adjacent to the eye.

However, none of these interventions are effective in the treatment of this disorder. Hence, it is desirable to develop agents which effectively treat dry eye, preferably with minimal side effects.

SUMMARY OF THE INVENTION

In one aspect, the present invention provides methods for treatment of inflammatory disorders mediated by LFA-1 by administering an effective amount of an antagonist of LFA-1 by itself or in combination with other therapeutic agents to a subject. In some embodiments of the invention, diseases in which the anti-LFA-1 antibody, Raptiva, has shown therapeutic effect or effect on inflammatory cells in the diseased tissue are disease that are treated by the LFA-1 compounds of the present invention. Patients with immune mediated allergic diseases including rhinitis may be treated with the compounds of the invention to reduce the inflammation associated with LFA-1 mediated immune and/or allergic responses. In some embodiments, a local administration of the compounds of the invention, delivered via the mouth or nose as a misted solution or dispersed powder is useful in the treatment of asthma or other LFA-1 mediated pulmonary inflammatory diseases. In some embodiments, a cream formulation of the compounds of the invention is useful in the local delivery of a LFA-1 antagonist to the skin in dermatologic diseases mediated by LFA-1 such as eczema and psoriasis. In some embodiments, an oral formulation of a LFA-1 antagonist which is known to be poorly absorbed at the systemic level is administered by the oral route in animal studies is useful for local topical deliver of LFA-1 antagonists in the treatment of inflammatory diseases of the gastrointestinal (GI) tract, including Crohn's disease and irritable bowel syndrome, or other GI disease mediated by LFA-1 or other leucocyte integrins including VLA4 and Mac-1.

In some embodiments, the disorder that is mediated by LFA-1 is an eye disorder. In some embodiments the inflammatory disorder that is mediated by LFA-1 is dry eye. In particular, the methods of the present invention are useful for treatment of dry eye syndrome. This syndrome encompasses symptoms caused by: keratoconjunctivitis sicca, Sjorgen's syndrome, corneal injury, age-related dry eye, Stevens-Johnson syndrome, congenital alachrima, pharmacological side effects, infection, Riley-Day syndrome, conjunctival fibrosis, eye stress, glandular and tissue destruction, ocular cicatrical pemphogoid, blepharitis, autoimmune and other immunodeficient disorders, allergies, diabetes, lacrimal gland deficiency, lupus, Parkinson's disease, Sjogren's syndrome, rheumatoid arthritis, rosacea, environmental exposure to excessively dry air, airborne particulates, smoke, and smog and inability to blink, amongst others. Many patients suffering from dry eye may also have an underlying autoimmune disease, Sjogren's syndrome. Currently recognized diagnostic criteria for patient identification include clinical signs and symptoms of dry mouth. The compounds of the present invention may be useful in treating this symptom, in formulations of mouthwash or lozenges. A skin cream applied to the outer surface of the eyelids thus delivering a LFA-1 antagonist across the eyelid to the inner lining of the eyelid and the intervening conjunctival tissue and accessory lacrimal glands is desirable in treating LFA-1 mediated inflammation of the eyelid and eye, particularly in the treatment of dry eye.

Another aspect of the present invention provides pharmaceutical compositions which comprise a LFA-1 antagonist for administration in the methods of treatment of inflammatory disorders mediated by LFA-1. In some embodiments the inflammatory disorder mediated by LFA-1 is an eye disorder for which pharmaceutical compositions which comprise a LFA-1 antagonist are provided. In some embodiments the inflammatory disorder mediated by LFA-1 is dry eye, for which pharmaceutical compositions which comprise a LFA-1 antagonist have been provided. It is further provided that the compositions may further comprise another therapeutic agent to be co-administered either in the same formulation or separately. In some embodiments, the pharmaceutical compositions are administered orally, via injection, intranasally, via inhalation, rectally, topically, via instillation to the ocular surface, or transdermally.

In another aspect, the present invention provides formulations for the compositions which are adminstered in the methods of treatment of inflammatory disorders mediated by LFA-1. In some embodiments, gastro-retentive formulations of compositions are provided for administration to treat inflammatory disorders mediated by LFA-1. In some embodiments, gastro-retentive formulations of compositions are provided for administration to treat eye disorders which are inflammatory disorders mediated by LFA-1. In some embodiments, ocular formulations of compositions are provided for administration to treat dry eye which is the inflammatory disorder mediated by LFA-1. In some embodiments, ocular formulations of compositions are provided for administration to treat inflammatory disorders mediated by LFA-1. In some embodiments, formulations of compositions are provided for administration to treat inflammatory disorders mediated by LFA-1, which are solutions, creams, powders, suspensions, mists, gels, solids, and the like. Controlled release formulations are also provided for in some embodiments of the invention. In some embodiments of the invention, the compounds of the invention are formulated as prodrugs.

In another aspect, compounds are provided for use in the methods of the invention. Compounds that are useful in the methods of the invention include antibodies, fragments of antibodies, polypeptides, peptides, polymers, and organic small molecules. In another an embodiment of the method of the present invention, Raptiva is used in an ocular formulation to treat dry eye.

One aspect of the invention combines a diagnostic with a method of treatment with an LFA-1 antagonist. In one embodiment, a diagnostic test for Sjorgren's is performed and after a diagnosis of the disease is made, the patient is administered an LFA-1 antagonist as described herein. In another embodiment, a diagnostic test for dry eye is performed and after a diagnosis of dry eye is made, the patient is administered an LFA-1 antagonist as described herein.

The compounds provided herein are administered to increase tear or mucin production to a subject suffering from an inflammatory disorder mediated by LFA-1. Preferably, the inflammatory disorder treated is an eye disorder. Even more preferably, the inflammatory disorder is dry eye.

In another aspect, a method for identifying inhibitors of the LFA-1: ICAM-1 interaction is provided. In some embodiments, the inhibitors are identified as being directly competitive with ICAM-1 binding to LFA-1 at the αL subunit of LFA-1. In some embodiments, the method utilizes competitive binding experiments to identify antagonists of the LFA-1: ICAM-1 interaction. In some embodiments, labeled probe molecules which are known to bind at metal ion dependent adhesion site of the LFA-1:ICAM-1 interaction on the αL subunit of LFA-1 are employed.

In another aspect a method of identifying useful pharmaceutical agents for human disease is described using the pattern of the inhibition of cell growth by siRNA (small interfering RNA sequences) directed against a cellular target involved in cell growth and human disease to identify compounds with a similar pattern of cell growth inhibition in a group of cultured cell lines. The methods of this invention can also be used to identify useful inhibitors of LFA-1, the B-cell receptor BR3, Grb2 (a protein downstream of growth factor receptors in signaling cascades) and other protein targets inside and outside of cells. In another embodiment of this invention, the identification of compounds which fit an activity pattern opposite of the inhibition of cell growth by siRNA can be stimulants of cell growth useful in diseases and conditions of slow cell growth. Enhanced cell growth could be useful in wound healing and other clinical settings. In another embodiment of this invention, this method uses siRNA cellular activity data for target or selection of targets by searching public and/or proprietary databases of compound cellular activity for a pattern of similar cellular activity in response to a compound or collection of compounds as a method to identify compounds useful in the identification of a human pharmaceutical

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 depicts Table 1 showing cation dependence of small molecule antagonists for LFA-1.

DETAILED DESCRIPTION OF THE INVENTION

Figure 1:
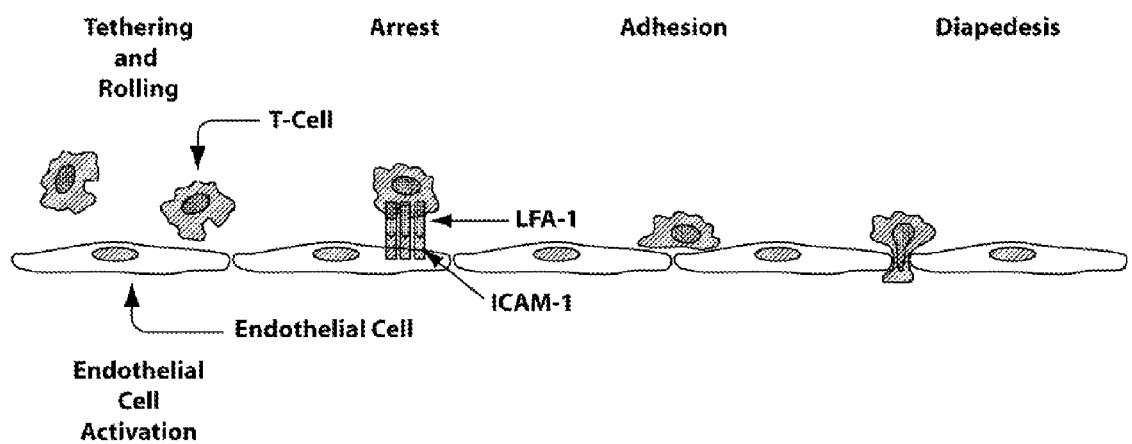
FIG. 1 depicts rolling, adhesion of leukocytes and transendothelial migration resulting from LFA-1:ICAM-1 interaction.

I. Interaction of Leukointegrins and Adhesion Receptors

Biology and Diseases

A first aspect of the present invention is methods for the treatment of the inflammatory component of immune and other disorders. In particular, the methods described herein are useful for the treatment of leukocyte mediated inflammation. This component plays a role in initiating and advancing inflammation in selected diseases, such as psoriasis, eczema, asthma, dermatitis, rheumatoid arthritis, systemic lupus erythematosis (SLE), multiple sclerosis, responses associated with inflammatory bowel disease, Reynaud's syndrome, Sjorgen's disease, juvenile onset diabetes, diabetes mellitus, granulomatosis, CNS inflammatory disorder, multiple organ injury disease, all types of transplantations, including graft versus host or host versus graft disease, HIV and rhinovirus infections, and atherosclerosis amongst other diseases.

A preferred embodiment of this invention is for the treatment of eye disorders. In particular, the methods of the present invention are useful for treatment of dry eye syndrome. This syndrome encompasses symptoms caused by: keratoconjunctivitis sicca, Sjorgen's syndrome, corneal injury, age-related dry eye, Stevens-Johnson syndrome, congenital alachrima, pharmacological side effects, infection, Riley-Day syndrome, conjunctival fibrosis, eye stress, glandular and tissue destruction, ocular cicatrical pemphogoid, blepharitis, autoimmune and other immunodeficient disorders, allergies, diabetes, lacrimal gland deficiency, lupus, Parkinson's disease, Sjogren's syndrome, rheumatoid arthritis, rosacea, environmental exposure to excessively dry air, airborne particulates, smoke, and smog and inability to blink, amongst others.

Not intending to limit the mechanism of action, the methods of the present invention involve the inhibition of initiation and progression of inflammation related disease by inhibiting the interaction between LFA-1 and ICAM-1. LFA-1 and ICAM-1 are molecules with extracellular receptor domains which are involved in the process of lymphocyte/leukocyte migration and proliferation, leading to a cascade of inflammatory responses. In preferred embodiments, such methods provide anti-inflammatory effects in-vitro and in-vivo, e.g., as described in more detail below, and are useful in the treatment of inflammation mediated diseases, and in particular, dry eye disease.

Human blood contains white blood cells (leukocytes) which are further classified as neutrophils, lymphocytes (with B- and T-subtypes), monocytes, eosinophils, and basophils. Several of these classes of leukocytes, neutrophils, eosinophils, basophils and lymphocytes, are involved in inflammatory disorders. LFA-1 is one of a group of leucointegrins which are expressed on most leucocytes, and is considered to be the lymphoid integrin which interacts with a number of ICAMs as ligands. Disrupting these interactions, and thus the immune/inflammatory response provides for reduction of inflammation, in particular, inflammation of the eye.

For example, ICAM-1 (CD54) is a member of the ICAM family of adhesion receptors (ICAM-1, ICAM-2, ICAM-3, ICAM-4) in the immunoglobulin protein super family, and is expressed on activated leucocytes, dermal fibroblasts, and endothelial cells. See Krensky, A. M.; Sanchez-Madrid, F.; Robbins, E.; Nagy, J. A.; Springer, T. A. Burakoff, S. J. "The functional significance, distribution, and structure of LFA-1, LFA-2, and LFA-3: cell surface antigens associated with CTL-target interactions." 1983 J. Immunol. 131, 611-616. It is normally expressed on the endothelial cells lining the vasculature, and is upregulated upon exposure to cytokines such as IL-1, LPS and TNF during immune/inflammatory initiation.

Research conducted over the last decade has helped elucidate the molecular events involved in the movement and activation of cells in the immune system, focusing on cell-to-cell triggering interactions within the cascade. See Springer, T. A. "Adhesion receptors of the immune system." Nature, 1990, 346, 425-434. The interaction of Intercellular Adhesion Molecules (ICAMs) with leukointegrins plays a role in the functioning of the immune system. It is believed that immune processes such as antigen presentation, T-cell mediated cytotoxicity and leukocyte transendothelial migration (diapedesis) require cellular adhesion mediated by ICAMs interacting with leukointegrins. See Kishimoto, T. K.; Rothlein; R. R. "Integrins, ICAMs, and selectins: role and regulation of adhesion molecules in neutrophil recruitment to inflammatory sites." Adv. Pharmacol. 1994, 25, 117-138 and Diamond, M.; Springer, T. A. "The dynamic regulation of integrin adhesiveness." Current Biology, 1994, 4, 506-532.

The interaction of ICAM-1 and LFA-1 (also referred to as $\alpha_L\beta_2$ and CD11a/CD18) has been shown to be involved in the processes of adhesion, leukocyte transendothelial migration, migration to sites of injury, and proliferation of lymphocytes at the activated target site, as shown in FIG. 1. For example, it is presently believed that prior to leukocyte transendothelial migration, a component of the inflammatory response, the presence of cytokines/chemokines activate integrins constitutively expressed on leukocytes. Blood vessel endothelial cells also upregulate ICAM-1 in response to the presence of the same cytokines/chemokines. As rolling leukocytes approach activated endothelial cells, their progress is first slowed by these upregulated ICAM-1 receptors. This is followed by a ligand/receptor interaction between LFA-1 and ICAM-1, expressed on blood vessel endothelial cell surfaces, which arrests the lymphocyte from rolling further. The lymphocyte then flattens, and transvasation takes place. This process is of importance both in lymphocyte transmigration through vascular endothelial as well as lymphocyte trafficking from peripheral blood to lymph nodes.

Figure 2:
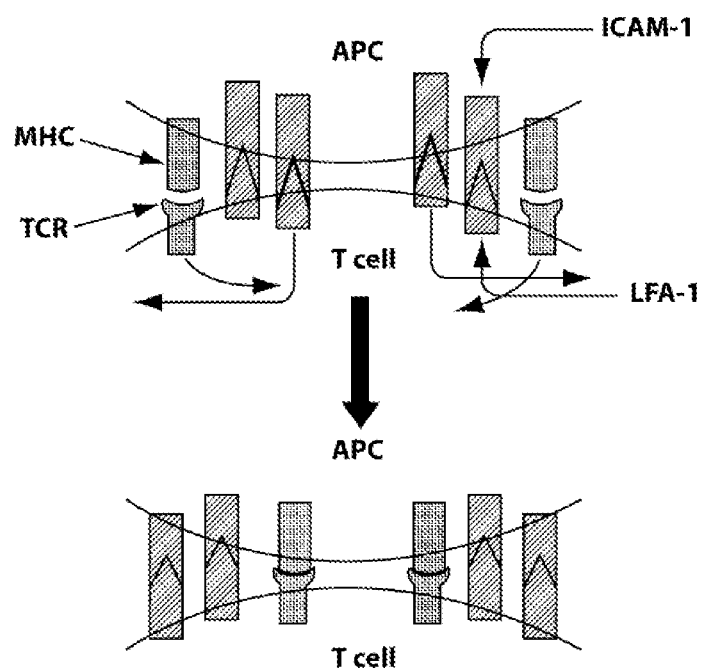
FIG. 2 depicts antigen activation of the LFA-1:ICAM-1 interaction.
Figure 2:
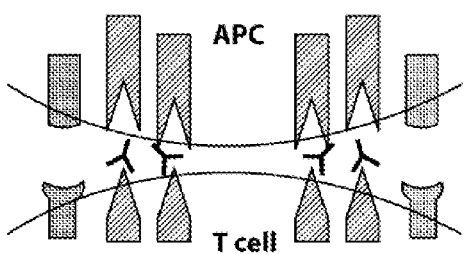
Figure 3:
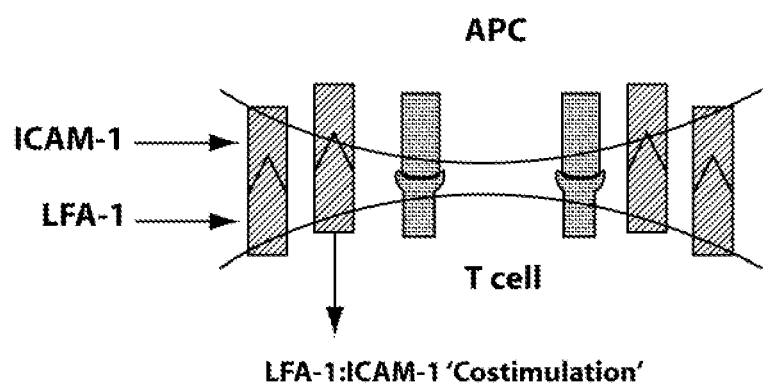
FIG. 3 depicts co-stimulatory function of the LFA-1: ICAM-1 interaction.
Figure 3:
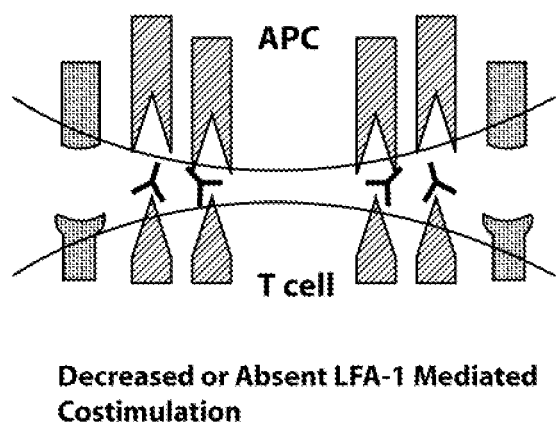

LFA-1 plays a role in creating and maintaining the immunological synapse, which may be defined as the physical structure of the interacting surfaces of T cells and Antigen Presenting Cells (APCs), as shown in FIG. 2. LFA-1 stabilizes T-cell engagement with the APC, and thus leads to activation of T cells. The interaction of LFA-1 and ICAM-1 also appears to provide co-stimulatory signals to resting T cells, as shown in FIG. 3. CD4+ T-cell proliferation and cytokine synthesis are mediated by this interaction as part of the inflammatory response.

Given the role that the interaction of ICAM-1 and LFA-1 plays in immune/inflammatory response, it is desirable to modulate these interactions to achieve a desired therapeutic result (e.g., inhibition of the interaction in the event of an overactive inflammatory response). Also, since LFA-1 has several ligand partners within the ICAM family (ICAM-1, ICAM-2 and ICAM-3), involving a number of signaling pathways, in some embodiments of the invention, it is desirable to modulate these interactions selectively. It has been demonstrated that the antagonism of the interaction between ICAMs and leukointegrins can be realized by agents directed against either component.

The methods and compositions described herein can modulate one or more components of the pathways described herein. In addition to inhibiting interaction between LFA-1 and ICAM-1, the methods and compositions of the present invention may also intervene in either earlier or later portions of the inflammatory process as well. For example, upregulation of ICAM-1 or LFA-1 (activation) on endothelial cells or leukocytes, prior to tethering and transendothelial migration, may be modulated by the methods and compositions described herein. The present invention may be useful in modulating the expression of cytokines or chemokines that activate ICAM-1 and LFA-1 in the course of leukocyte trafficking, in modulating the transport of the cytokines or chemokines, in preventing transvasation of the arrested leukocyte, in modulating signalling via other mechanisms that are involved in leukocyte proliferation at the site of injury or inflammation, and the like.

II. Methods of Treatment

The term "subject" as used herein includes animals, in particular humans as well as other mammals. The methods generally involve the administration of one or more drugs for the treatment of one or more diseases. Combinations of agents can be used to treat one disease or multiple diseases or to modulate the side-effects of one or more agents in the combination. The compounds described herein can be used in combination with other dry eye treatment agents. Also, the compounds of the invention can be used with drugs that cause dry eye as a side effect.

The term "treating" and its grammatical equivalents as used herein includes achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made. The compositions may be administered to a subject to prevent progression of physiological symptoms or of the underlying disorder.

In some embodiments, the therapeutic agent is present in an amount sufficient to exert a therapeutic effect by an average of at least about 5, 10, 15, 20, 25, 30, 40, 50, 60, 70, 80, 90, more than 90%, or substantially eliminate the disease or at least one of its underlying symptoms. Preferably the therapeutic effect is an effect on inflammation.

In some embodiments, the therapeutic agent is present in an amount sufficient to exert a therapeutic effect to reduce symptoms of dry eye by an average of at least about 5, 10, 15, 20, 25, 30, 40, 50, 60, 70, 80, 90, more than 90%, or substantially eliminate symptoms of dry eye.

In some embodiments, an effective amount of the therapeutic agent is a daily dose of about $1\times10^{-11}$, $1\times10^{-10}$, $1\times10^{-9}$, $1\times10^{-8}$, $1\times10^{-7}$, $1\times10^{-6}$, $1\times10^{-5}$, $1\times10^{4}$, $1\times10^{-3}$, $1\times10^{-2}$, $1\times10^{-1}$, 1, $1\times10^{1}$, $1\times10^{2}$ grams.

Administration of the therapeutic agent may be by any suitable means. In some embodiments, the therapeutic agent is administered by oral administration. In some embodiments, the therapeutic agent is administered by transdermal administration. In some embodiments, the therapeutic agent is administered by injection. In some embodiments, the therapeutic agent is administered topically. If combinations of agents are administered as separate compositions, they may be administered by the same route or by different routes. If combinations of agents are administered in a single composition, they may be administered by any suitable route. In some embodiments, combinations of agents are administered as a single composition by oral administration. In some embodiments, combinations of agents are administered as a single composition by transdermal administration. In some embodiments, the combinations of agent are administered as a single composition by injection. In some embodiments, the combinations of agent are administered as a single composition topically.

The method of the invention described herein is a method of administering an antagonist of LFA-1 to a subject to treat dry eye. In particular, the LFA-1 antagonist can modulate inflammation mediated by leukocytes. A preferred embodiment of the invention treats a subject by administering an antagonist of LFA-1 to modulate inflammation associated with ocular inflammation. Another preferred embodiment of the method is to treat a subject with inflammation associated with dry eye syndrome by administering an antagonist of LFA-1. An embodiment of the invention treats a subject with symptoms of dry eye due to allergies. An embodiment of the invention treats a subject with symptoms of dry eye disorder due to diabetes. An embodiment of the invention treats a subject with symptoms of dry eye disorder due to lacrimal gland deficiency. An embodiment of the invention treats a subject with symptoms of dry eye disorder due to lupus. An embodiment of the invention treats a subject with symptoms of dry eye disorder due to Parkinson's disease. An embodiment of the invention treats a subject with symptoms of dry eye disorder due to Sjogren's disease. An embodiment of the invention treats a subject with symptoms of dry eye disorder due to rheumatoid arthritis. An embodiment of the invention treats a subject with symptoms of dry eye disorder due to rosacea. An embodiment of the invention treats a subject with symptoms of dry eye disorder due to complications arising from LASIK therapy for vision correction. An embodiment of the invention treats a subject with symptoms of dry eye disorder due to use of contact lenses. An embodiment of the invention treats a subject with symptoms of dry eye disorder due to exposure to arid climates. An embodiment of the invention treats a subject with symptoms of dry eye disorder due to exposure to air pollution. An embodiment of the invention treats a subject with symptoms of dry eye disorder due to windy climates. An embodiment of the invention treats a subject with symptoms of dry eye disorder due to exposure due to cigarette smoke. An embodiment of the invention treats a subject with symptoms of dry eye disorder due to keratoconjunctivitis sicca. An embodiment of the invention treats a subject with symptoms of dry eye disorder due to corneal injury. An embodiment of the invention treats a subject with symptoms of dry eye disorder due to conjunctival fibrosis. An embodiment of the invention treats a subject with symptoms of dry eye disorder due to age-related dry eye. An embodiment of the invention treats a subject with symptoms of dry eye disorder due to Stevens-Johnson syndrome. An embodiment of the invention treats a subject with symptoms of dry eye disorder due to congenital alachrima. An embodiment of the invention treats a subject with symptoms of dry eye disorder due to pharmacological side effects of other drugs being taken by the patient. An embodiment of the invention treats a subject with symptoms of dry eye disorder due to infection. An embodiment of the invention treats a subject with symptoms of dry eye disorder due to Riley-Day syndrome. An embodiment of the invention treats a subject with symptoms of dry eye disorder due to eye stress, including that due to computer use. An embodiment of the invention treats a subject with symptoms of dry eye disorder due to glandular and tissue destruction. An embodiment of the invention treats a subject with symptoms of dry eye disorder due to ocular cicatrical pemphogoid. An embodiment of the invention treats a subject with symptoms of dry eye disorder due to blepharitis. An embodiment of the invention treats a subject with symptoms of dry eye disorder due to autoimmune and other immunodeficient disorders. An embodiment of the invention treats a subject with symptoms of dry eye disorder due to an inability to blink. An embodiment of the invention treats a subject with symptoms of psoriasis with a LFA-1 antagonist of the method. An embodiment of the invention treats a subject with symptoms of eczema with a LFA-1 antagonist of the method. An embodiment of the invention treats a subject with symptoms of lupus with a LFA-1 antagonist of the method. An embodiment of the invention treats a subject with symptoms of Reynaud's syndrome with a LFA-1 antagonist of the method. An embodiment of the invention treats a subject with symptoms of granulomatosis with a LFA-1 antagonist of the method. An embodiment of the invention treats a subject with symptoms of CNS inflammatory disorder with a LFA-1 antagonist of the method. An embodiment of the invention treats a subject with symptoms of multiple organ disease with a LFA-1 antagonist of the method. An embodiment of the invention treats a subject with symptoms of allergic rhinitis with a LFA-1 antagonist of the method. An embodiment of the invention treats a subject with symptoms of granulomatosis with a LFA-1 antagonist of the method. An embodiment of the invention treats a subject with symptoms of atherosclerosis with a LFA-1 antagonist of the method. An embodiment of the invention treats a subject with symptoms of graft versus host disease with a LFA-1 antagonist of the method. An embodiment of the invention treats a subject with symptoms of host versus graft disease with a LFA-1 antagonist of the method. An embodiment of the invention treats a subject with symptoms of inflammatory response associated with transplantation with a LFA-1 antagonist of the method. An embodiment of the invention treats a subject with symptoms of inflammatory bowel disease with a LFA-1 antagonist of the method. An embodiment of the invention treats a subject with symptoms of juvenile onset diabetes with a LFA-1 antagonist of the method. An embodiment of the invention treats a subject with symptoms of diabetes mellitus with a LFA-1 antagonist of the method. An embodiment of the invention treats a subject with symptoms of multiple sclerosis with a LFA-1 antagonist of the method. An embodiment of the invention treats a subject with symptoms of asthma with a LFA-1 antagonist of the method. An embodiment of the invention treats a subject with symptoms of dermatitis with a LFA-1 antagonist of the method. An embodiment of the invention treats a subject with symptoms of systemic lupus erythematosis with a LFA-1 antagonist of the method. An embodiment of the invention treats a subject with symptoms of HIV and rhinovirus infections with a LFA-1 antagonist of the method.

In some embodiments of the invention, diagnostic procedures will be employed to identify a subject in need of treatment by the method of the invention. Fluorescein staining of the cornea is used to diagnose symptoms of dry eye disorder. Rose Bengal staining of the cornea is used to diagnose symptoms of dry eye disorder. Corneal sensitivity is used to diagnose symptoms of dry eye disorder. Tear breakup time (BUT) is used to diagnose symptoms of dry eye disorder. Schirmer test with anesthesia is used to diagnose symptoms of dry eye disorder. Schirmer test analysis is used to diagnose symptoms of dry eye disorder. Impression cytology is used to diagnose symptoms of dry eye disorder. Subjective dry eye symptoms are used to diagnose symptoms of dry eye disorder. Tear flow analysis is used to diagnose symptoms of dry eye disorder. Immunohistochemical methods, including but not limited to human leukocyte antigen II (HLA-DR), are used to diagnose symptoms of dry eye disorder. Antinuclear antibody test (ANA) or fluorescent antinuclear antibody test (FANA) is used to diagnose symptoms of dry eye disorder. Ocular evaporation is used to diagnose symptoms of dry eye disorder. Infrared meibography is used to diagnose symptoms of dry eye disorder. Tandem scanning confocal microscopy (TSCM) is used to diagnose symptoms of dry eye disorder. This is an exemplary list of procedures that may be used to diagnose symptoms of dry eye and is in no way limiting.

The antagonist of the method of the invention may be an antibody, fragment of an antibody, peptide or small molecule. In preferred embodiments, the LFA-1 antagonist used is a peptide which is not an antibody. The antagonist of the method is a therapeutic agent.

Many therapeutic indications for LFA-1 antagonists require chronic therapy; therefore, small molecule inhibitors of the LFA-1/ICAM-1 interaction are one group of preferred embodiments of this invention as they have the potential for oral administration as well as a lowered cost of goods.

A further preferred embodiment is a method of treating dry eye disease using therapeutic agents which are suitable for formulation and administration as ocular therapeutics.

Another aspect of the present invention is described herein and below, a method of comparison of the binding of ICAM-1 and antagonists which can be utilized to identify antibodies, antibody fragments, peptides, and small molecules as antagonists of the LFA-1: ICAM-1 interaction. See Gadek et al. 2002. The method is described in terms of identifying small molecule antagonists. However, it should not be interpreted as limiting the method in any manner to exclude its use in identifying larger molecule types of inhibitors of LFA-1, such as antibodies, fragments of antibodies or peptides.

This method comprises choosing one or more of the following steps as part of the process of identifying an antagonist as a directly competitive inhibitor of LFA-1: (a) competition experiments utilizing full length wild type LFA-1 comparing the binding of potential antagonistic agents to that of sICAM-1 (the extracellular domains of LFA-1's native ligand and a competitive LFA-1/ICAM-1 inhibitor) and A-286982 (an allosteric LFA-1/ICAM-1 inhibitor known to bind to the I (inserted) domain allosteric site (IDAS)). See Liu, G.; Huth, J. R.; Olejniczak, E. T.; Mendoza, R.; DeVries, P.; Leitza, S.; Reilly; E. B., Okasinski; G. F.; Fesik, S. W.; and von Geldern, T. W. 2001. "Novel p-arylthio cinnamides as antagonists of leukocyte function-associated antigen-1/intracellular adhesion molecule-1 interaction. 2. Mechanism of inhibition and structure-based improvement of pharmaceutical properties." J. Med. Chem., 44, 1202-1210)), (b) binding studies of potential antagonistic agents and ICAM-1 with a LFA-1 mutant, and (c) chemical crosslinking studies. The ICAM-1 binding site targeted herein has previously been localized to include the metal ion dependent adhesion site (MIDAS) motif within the I domain of the LFA-1 α subunit. See Shimaoka, M., Xiao, T., Liu, J.-H., Yang, Y., Dong, Y., Jun, C-D., McCormack, A. Zhang, R., Joachimiak, A., Takagi, J., Wang, J.-H., and Springer, T. A. 2003 "Structures of the alpha L I domain and its complex with ICAM-1 reveal a shape-shifting pathway for integrin regulation" Cell 2003, 99-111. Antagonists that inhibit ICAM-1 binding to LFA-1 by direct competition for a common high affinity binding site on LFA-1 can be identified using one or more steps of this method.

A. Antibodies as Therapeutic Agents

Several suitable antibodies are known in the art. Blocking of the CAMs, such as for example ICAM-1, or the leukointegrins, such as for example, LFA-1, by antibodies directed against either or both of these molecules can inhibit inflammatory response. Previous studies have investigated the effects of anti-CD11a MAbs on many T-cell-dependent immune functions in vitro and a number of immune responses in vivo. In vitro, anti-CD11a MAbs inhibit T-cell activation (See Kuypers T. W., Roos D. 1989 "Leukocyte membrane adhesion proteins LFA-1, CR3 and p150,95: a review of functional and regulatory aspects" Res. Immunol., 140: 461-465; Fischer A, Durandy A, Sterkers G, Griscelli C. 1986 "Role of the LFA-1 molecule in cellular interactions required for antibody production in humans" J. Immunol., 136, 3198; target cell lysis by cytotoxic T-lymphocytes (Krensky et al., supra), formation of immune conjugates (Sanders V M, Snyder J M, Uhr J W, Vitetta E S., "Characterization of the physical interaction between antigen-specific B and T cells". J. Immunol., 137: 2395 (1986); Mentzer S J, Gromkowski S H, Krensky A M, Burakoff S J, Martz E. 1985 "LFA-1 membrane molecule in the regulation of homotypic adhesions of human B lymphocytesn" J. Immunol., 135: 9), and the adhesion of T-cells to vascular endothelium (Lo S K, Van Seventer G A, Levin S M, Wright S D., Two leukocyte receptors (CD11a/CD18 and CD11b/CD18) mediate transient adhesion to endothelium by binding to different ligands., J. Immunol., 143: 3325 (1989)). Two anti-CD11a MAbs, HI 111, and G43-25B are available from Pharmingen/BD Biosciences. Additionally, a study including F8.8, CBR LFA 1/9, BLS, May.035, TS1/11, TS1/12, TS1/22, TS2/14, 25-3-1, MHM2 and efalizumab evaluated the range of binding sites on LFA-1 these antibodies occupied. See Lu, C; Shimaoka, M.; Salas, A.; Springer, T. A. 2004, "The Binding Sites for Competitive Antagonistic, Allosteric Antagonistic, and Agonistic Antibodies to the I Domain of Integrin LFA-1" J. Immun. 173: 3972-3978 and references therein.

The observation that LFA-1:ICAM-1 interaction is necessary to optimize T-cell function in vitro, and that anti-CD11a MAbs induce tolerance to protein antigens (Benjamin R J, Qin S X, Wise M P, Cobbold S P, Waldmann H. 1988 "Mechanisms of monoclonal antibody-facilitated tolerance induction: a possible role for the CD4 (L3T4) and CD11a (LFA-1) molecules in self-non-self discrimination" Eur. J. Immunol., 18: 1079) and prolongs tumor graft survival in mice (Heagy W, Walterbangh C, Martz E. 1984 "Potent ability of anti-LFA-1 monoclonal antibody to prolong allograft survival" Transplantation, 37: 520-523) was the basis for testing the MAbs to these molecules for prevention of graft rejection in humans. Experiments have also been carried out in primates. For example, based on experiments in monkeys, it has been suggested that a MAb directed against ICAM-1 can prevent or even reverse kidney graft rejection (Cosimi et al., "Immunosuppression of Cynomolgus Recipients of Renal Allografts by R6.5, a Monoclonal Antibody to Intercellular Adhesion Molecule-1," in Springer et al. (eds.), Leukocyte Adhesion Molecules New York: Springer, (1988), p. 274; Cosimi et al., J. Immunology, 144: 4604-4612 (1990)). Furthermore, the in vivo administration of anti-CD11a MAb to cynomolgus monkeys prolonged skin allograft survival See Berlin et al., Transplantation, 53: 840-849 (1992).

B. Small Molecules

Peptides have been investigated for use in reducing the interaction of LFA-1 with ICAM-1. Polypeptides that do not contain an Fc region of an IgG are described in U.S. Pat. No. 5,747,035, which can be used to treat LFA-1 mediated disorders, in particular dry eye. Use of dual peptides, the first a modulator of ICAM-1 and the second a blocking peptide with a sequence obtained from LFA-1 is described in U.S. Pat. No. 5,843,885 to reduce the interactions between LFA-1 and ICAM-1. Cyclic peptides have been described in U.S. Pat. No. 6,630,447 as inhibitors of the LFA-1: ICAM-1 interaction.

Small molecule antagonists include statins which bind to the CD11a domain of LFA-1. See Kallen, J., Welzenbach, K., Ramage, P. Geyl, D. Kriwacki, R., Legge, G., Cottens, S., Weitz-Schmidt, G., and Hommel, U. 1999. "Structural basis for LFA-1 inhibition upon lovastatin binding to the CD11a I-domain", J. Mol. Biol., 292: 1-9; and Weitz-Schmidt, G., Welzenbach, K., Brinkmann, V., Kamata, T., Kallen, J., Bruns, C., Cottens, S., Takada, Y., and Hommel, U. 2001. Statins selectively inhibit leukocyte function antigen-1 by binding to a novel regulatory integrin site, Nature Med., 7: 687-692; and Frenette, P. S. 2001. "Locking a leukocyte integrin with statins", N. Engl. J. Med., 345: 1419-1421. Molecules derived from the mevinolin/compactin motif also show activity against LFA-1. See Welzenbach, K., Hommel, U., and Weitz-Schmidt, G. 2002. "Small molecule inhibitors induce conformational changes in the I domain and the I-like domain of Lymphocyte Function-Associated Antigen-1", J. Biol. Chem., 277: 10590-10598, and U.S. Pat. No. 6,630,492.

A family of hydantoin-based inhibitors can also be used as antagonists. See Kelly, T. A., Jeanfavre, D. D., McNeil, D. W., Woska, J. R. Jr., Reilly, P. L., Mainolfi, E. A., Kishimoto, K. M., Nabozny, G. H., Zinter, R., Bormann, B.-J., and Rothlein, R. 1999. "Cutting edge: a small molecule antagonist of LFA-1-mediated cell adhesion", J. Immunol., 163: 5173-5177. These compounds are believed to be allosteric inhibitors of LFA-1.

A family of novel p-arylthio cinnamides can act as antagonists of LFA-1. See Liu, G.; Link, J. T.; Pei, Z.; Reilly, E. B.; Nguyen, B.; Marsh, K. C.; Okasinski, G. F.; von Geldern, T. W.; Ormes, M.; Fowler, K.; Gallatin, M. 2000 "Discovery of novel p-arylthio cinnamides as antagonists of leukocyte function-associated antigen-1/intracellular adhesion molecule-1 interaction. 1. Identification of an additional binding pocket based on an anilino diaryl sulfide lead." J. Med. Chem. 43, 4015-4030.

Other families of small molecule inhibitors are disclosed in publications (See Gadek, T. R., Burdick, D. J., McDowell, R. S., Stanley, M. S., Marsters, J. C. Jr., Paris, K. J., Oare, D. A., Reynolds, M. E., Ladner, C., Zioncheck, K. A., Lee, W. P., Gribling, P., Dennis, M. S., Skelton, N. J., Tumas, D. B., Clark, K. R., Keating, S. M., Beresini, M. H., Tilley, J. W., Presta, L. G., and Bodary, S. C. 2002. "Generation of an LFA-1 antagonist by the transfer of the ICAM-1 immunoregulatory epitope to a small molecule" Science, 295: 1086-1089 and online supplementary material.) and in patents, including U.S. Pat. No. 6,872,735, U.S. Pat. No. 6,667,318, U.S. Pat. No. 6,803,384, U.S. Pat. No. 6,515,124, U.S. Pat. No. 6,331,640, and patent applications, including: U.S. 20020119994. U.S. 20040058968, U.S. 20050080119, WO99/49856, WO00/21920, WO01/58853, WO02/59114, WO05/044817, and others. The contents of all the cited references are incorporated in their entirety by reference.

In some embodiments, the compounds described herein are used in combination with restasis (Cyclosporine A). The compounds of the invention can also be used to increase mucin production and/or tear production. Thus, the compounds of the present invention can offer additional relief beyond decreasing inflammation and by also increasing the mucin production that makes up a portion of tear film.

The interaction of LFA-1 and ICAMs are known to be involved in various autoimmune and inflammatory diseases, particularly those with involvement of lymphocytic (T- or B-cell), dendritic, monocytic cells expressing LFA-1 on their surface as part of the inflammatory component of disease. LFA-1 antagonists can be particularly useful in treatment of these diseases because the therapeutic target's expression in diseased tissue is limited to infiltrating cells of the immune system. LFA-1 can block the adhesion, migration, proliferation, and release of inflammatory signals to surrounding tissue by immune system cells. The anti-LFA-1 antibody, Raptiva, which has an effect on inflammatory cells in diseased tissue may be used to treat dry eye.

Many patients suffering from dry eye may also have an underlying autoimmune disease, Sjogren's syndrome. Currently recognized diagnostic criteria include clinical signs and symptoms of Dry Mouth. The compounds of the present invention may be useful in treating this symptom, in formulations of mouthwash or lozenges. A lozenge incorporating the compounds of the invention in a solid or waxy material may stimulate salivary secretion while releasing the compound of the invention under sustained release.

Patients with immune mediated allergic diseases including rhinitis may be treated with the compounds of the invention. For example, a LFA-1 antagonist may be delivered locally to the nose, nasal passages, and/or nasal cavity to reduce the inflammation associated immune and/or allergic responses.

A local administration of the compounds of the invention, delivered via the mouth or nose as a misted solution or dispersed powder may be useful in the treatment of Asthma or other LFA-1 mediated pulmonary inflammatory dieseases.

A cream formulation of the compounds of the invention could be useful in the local delivery of a LFA-1 antagonist to the skin in dermatologic diseases mediated by LFA-1 such as eczema and psoriasis. Compounds useful in this regard include LFA-1 antagonists and their pro-drugs which are transformed into the active drug in inflamed skin. A skin cream applied to the outer surface of the eyelids thus delivering a LFA-1 antagonist across the eyelid to the inner lining of the eyelid and the intervening conjunctival tissue and accessory lacrimal glands may be desirable in treating LFA-1 mediated inflammation of the eyelid and eye, particularly in the treatment of dry eye.

An oral formulation of a LFA-1 antagonist which is known to be poorly absorbed at the systemic level by the oral route in animal studies may be useful for local topical deliver of LFA-1 antagonists in the treatment of inflammatory diseases of the gastrointestinal (GI) tract, including Crohn's disease and Irritable Bowel Syndrome, or other GI disease mediated by LFA-1 or other leucocyte integrins including VLA4 and Mac-1.

II. Compounds Useful in the Method

A. Definitions

The term "aliphatic", as used herein, includes both saturated and unsaturated, straight chain (unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like.

Furthermore, as used herein, the terms "alkyl", "alkenyl", "alkynyl", and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents.

Alkenyl groups include, but are not limited to, for example, ethenyl, propenyl, butenyl, and the like. Representative alkynyl groups include, but are not limited to, ethynyl, 2-propynyl and the like.

The term "lower alkylene" as used herein refers to a hydrocarbon chain which links together two other groups, i.e. is bonded to another group at either end, for example methylene, ethylene, butylene and the like. Such a substituent is preferably from 1 to 10 carbons and more preferably from 1 to 5 carbons. Such groups may be substituted, preferably with an amino, acetylamino (a lower alkylcarbonyl group bonded via a nitrogen atom), or cyclo lower alkyl group. By the latter is meant a saturated hydrocarbon ring, preferably with a total of 3 to 10 methylenes (inclusive of the attachment carbons), more preferably 3 to 6.

The term "alicyclic", as used herein, refers to compounds which combine the properties of aliphatic and cyclic compounds and include but are not limited to monocyclic, or polycyclic aliphatic hydrocarbons and bridged cycloalkyl compounds, which are optionally substituted with one or more functional groups.

As will be appreciated by one of ordinary skill in the art, "alicyclic" is intended herein to include, but is not limited to, cycloalkyl, cycloalkenyl, and cycloalkynyl moieties, which are optionally substituted with one or more functional groups.

Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl, cyclohexyl, —CH$_2$-cyclohexyl, cyclohexenylethyl, cyclohexanylethyl, norbornyl moieties and the like, which again, may bear one or more substituents.

The term "alkoxy" or "alkyloxy", as used herein refers to a saturated or unsaturated parent molecular moiety through an oxygen atom. In certain embodiments, the alkyl group contains about 1-20 aliphatic carbon atoms. In certain other embodiments, the alkyl group contains about 1-10 aliphatic carbon atoms. In yet other embodiments, the alkyl group employed in the invention contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy, include but are not limited to, methoxy, ethoxy, isopropoxy, n-butoxy, i-butoxy, sec-butoxy, tert-butoxy, neopentoxy, n-hexloxy and the like.

The term "lower alkoxy" as used herein refers to a lower alkyl as defined above which may be branched or unbranched as also defined above and which is bonded by an oxygen to another group (i.e. alkyl ethers).

The term "thioalkyl" as used herein refers to a saturated or unsaturated (i.e., S-alkenyl and S-alkynyl) group attached to the parent molecular moiety through a sulfur atom. In certain embodiments, the alkyl group contains about 1-20 aliphatic carbon atoms. In certain other embodiments, the alkyl group contains about 1-10 aliphatic carbon atoms. In yet other embodiments, the alkyl group employed in the invention contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of thioalkyl include, but are not limited to, methylthio, ethylthio, propylthio, isopropylthio, n-butylthio, and the like.

The term "lower alkylthio" as used herein refers to a lower alkyl group bonded through a divalent sulfur atom, for example, a methylmercapto or an isopropylmercapto group. By lower alkylenethio is meant such a group which is bonded at each end.

The term "alkylamino" refers to a group having the structure-NHR' wherein R' is alkyl, as defined herein. The term "aminoalkyl" refers to a group having the structure $NH_2R'$—, wherein as defined herein. In certain embodiments, the alkyl group contains about 1-20 aliphatic carbon atoms. In certain other embodiments, the alkyl group contains about 1-10 aliphatic carbon atoms. In yet other embodiments, the alkyl group employed in the invention contains about aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; $R_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S, and N within the ring in place of a ring carbon atom). In certain embodiments, the term "heteroaromatic moiety" refers to a planar ring comprising at least one heteroatom, having p-orbitals perpendicular to the plane of the ring at each ring atom, and satisfying the Huckel rule where the number of pi electrons in the ring is (4n+2) wherein n is an integer.

It will also be appreciated that aromatic and heteroaromatic moieties, as defined herein may be attached via an alkyl or heteroalkyl moiety and thus also include-(alkyl) aromatic, -(heteroalkyl) aromatic, -(heteroalkyl) heteroaromatic, and -(heteroalkyl) heteroaromatic moieties. Thus, as used herein, the phrases"aromatic or heteroaromatic moieties" and"aromatic, (heteroalkyl) aromatic, -(heteroalkyl) heteroaromatic, and (heteroalkyl) heteroaromatic" are interchangeable. Substituents include, but are not limited to, any of the previously mentioned substituents, e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl" as used herein, does not differ significantly from the common meaning of the term in the art, and refers to a cyclic aromatic radical having from five to ten ring atoms of which one ring atom is selected from S, and N; zero, one or two ring atoms are additional heteroatoms independently selected from S, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(=O)$R_x$; —C(=O)N($R_x$)$_2$; —OC(=O)$R_x$; —$OCO_2R_x$; —OC(=O)N($R_x$)$_2$; —N($R_x$)$_2$; —S(O)$_2R_x$; —$NR_x$(CO)$R_x$ wherein each occurrence of $R_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl) aryl or -(alkyl) heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —C(=O)N(R$_x$)$_2$; —OC(=O)R$_x$; —OCO$_2$R$_x$; —OC(=O)N(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e. place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —C(=O)N(R$_x$)$_2$; —OC(=O)R$_x$; —OCO$_2$R$_x$; —OC(=O)N(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom heteroatom selected from S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —C(=O)N(R$_x$)$_2$; —OC(=O)R$_x$; —OCO$_2$R$_x$; —OC(=O)N(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl described above and herein may be substituted or unsubstituted. Additionally, it will be appreciated that any of the alicyclic or heterocyclic moieties described above and herein may comprise an aryl or heteroaryl moiety fused thereto.

The terms "halo" and "halogen" used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino" as used herein, refers to a primary (—NH₂), secondary (—NHR$_x$), tertiary (—NR$_x$R$_y$), or quaternary amine (—N'R$_x$R$_y$R$_z$), where R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, iso-propylamino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "sulfonamido" as used herein, refers to a group of the general formula —SO2NRxRy where Rx and Ry are independently hydrogen, or an aliphatic, alicyclic, heteroaliphatic, heterocyclic, aromatic, heteroaromatic or acyl moiety, as defined herein.

The term "benzamido", as used herein, refers to a group of the general formula PhNRx, where Rx is hydrogen, or an aliphatic, alicyclic, heteroaliphatic, heterocyclic, aromatic, heteroaromatic or acyl moiety, as defined herein.

The term "C 1-6 alkylidene" as used herein, refers to a substituted or unsubstituted, linear or branched saturated divalent radical consisting solely of carbon and hydrogen atoms, having from one to six carbon atoms, having a free valence "-" at both ends of the radical.

The term "C 2-6 alkylidene" as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", heterocycloalkyl", "heterocycle" and the like, encompass substituted and unsubstituted, and saturated and unsaturated groups. Additionally, the terms "cycloalkyl", cycloalkenyl", cycloalkynyl", "heterocycloalkyl" "heterocycloalkenyl", "heterocycloalkynyl", "aromatic", "heteroaromatic", "aryl", "heteroaryl" and the like encompass both substituted and unsubstituted groups.

The term "natural amino acid" as used herein refers to any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

The term "unnatural amino acid" as used herein refers to all amino acids which are not natural amino acids. This includes, for example, α-, β-, D-, L-amino acid residues, and compounds of the general formula:

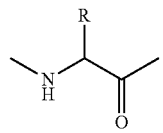

wherein the side chain R is other than the amino acid side chains occurring in nature.

More generally, the term "amino acid", as used herein, encompasses natural amino acids and unnatural amino acids.

The term "bioisosteres", as used herein, generally refers to two or more compounds or moieties that possess similar molecular shapes and/or volumes. In certain embodiments, bioisosteres have approximately the same distribution of electrons. In certain other embodiments, bioisosteres exhibit similar biological properties. In preferred embodiments, bioisosteres possess similar molecular shapes and volumes; have approximately the same distribution of electrons; and exhibit similar biological properties.

The term "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

As used herein, the term pharmaceutically acceptable salt" refers to those salts which are suitable for pharmaceutical use, preferably for use in the tissues of humans and lower animals without undue irritation, allergic response and the like. Pharmaceutically acceptable salts of amines, carboxylic acids, and other types of compounds, are well known in the art. For example, S. M. Berge, et al., describe pharmaceutically acceptable salts in detail in J Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzoate, bisulfate, borate, butyrate, camphorate, camphorsulfonate, citrate, cyclopentanepropionate, digluconate, dodecylsulfate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, nicotinate, nitrate, oleate, oxalate, palmitate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate and aryl sulfonate.

As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic alcohol compounds, particularly alkanes, alkenes, ethylene glycol, cycloalkanes, and the like in which each alkyl or alkenyl moiety advantageously has not more than 6 carbon atoms. These are exemplary only and in no way limit the possibilities of esters known in the art.

As used herein, the term "pharmaceutically acceptable prodrugs" refers to those prodrugs of the compounds of the present invention which are suitable for pharmaceutical use, preferably for use with the tissues of humans and lower animals with undue toxicity, irritation, allergic response, and the like, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference.

B. Exemplary Compounds of the Method

In one embodiment, compounds useful in the methods of the present invention include compounds of Formula I:

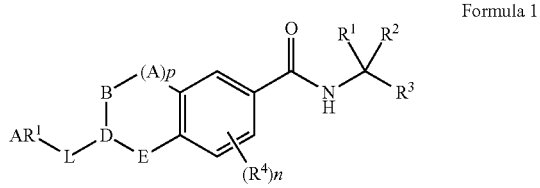

Formula 1 where $R^1$ and $R^2$ are each independently hydrogen, an amino acid side chain, —$(CH_2)_m$OH, —$(CH_2)_m$aryl, —$(CH_2)_m$heteroaryl, wherein m is 0-6, —$CH(R^{1A})(OR^{1B})$, —$CH(R^{1A})(NHR^{1B})$, U-T-Q, or an aliphatic, alicyclic, heteroaliphatic or heteroalicyclic moiety optionally substituted with U-T-Q; wherein U may be absent or one of the following: —O—, —S(O)$_{0\text{-}2}$—, —SO$_2$N(R$^{1A}$), —N(R$^{1A}$)—, —N(R$^{1A}$)C(=O)—, —N(R$^{1A}$)C(=O)—O—, —N(R$^{1A}$)C(=O)—N(R$^{1B}$)—, —N(R$^{1A}$)—SO$_2$—, —C(=O)—, —C(=O)—O—, —O—C(=O)—, aryl, heteroaryl, alkylaryl, alkylheteroaryl, —C(=O)—N(R$^{1A}$)—, —OC(=O)N(R$^{1A}$)—, —C(=N—R$^{1E}$C(=N—R$^{1E}$)—O—, —C(=N—R$^{1E}$)—N(R$^{1A}$)—, O—C(=N—R$^{1E}$)—N(R$^{1A}$)—, —N(R$^{1A}$)C(=N—R$^{1E}$)—, —N(R$^{1A}$)C(=N—R$^{1E}$)—O—, —N(R$^{1A}$)C(=N—R$^{1E}$)—N(R$^{1B}$)—, —P(=O)(OR$^{1A}$)—O—, or —P(=O)(R$^{1A}$)—O—; wherein T is absent or, an aliphatic, heteroaliphatic, aryl, heteroaryl, alkylaryl or alkylheteroaryl moiety; and Q is hydrogen, halogen, cyano, isocyanate, —OR$^{1B}$; —SR$^{1B}$; —N(R$^{1B}$)$_2$, —NHC(=O)OR$^{1B}$, —NHC(=O)N(R$^{1B}$)$_2$, —NHC(=O)R$^{1B}$, —NHSO$_2$R$^{1B}$, NHSO$_2$N(R$^{1B}$)$_2$, —NHSO$_2$NHC(=O)OR$^{1B}$, —NHC(=O)NHSO$_2$R$^{1B}$, —C(=O)NHC(=O)OR$^{1B}$, C(=O)NHC(=O)R$^{1B}$, —C(=O)NHC(=O)N(R$^{1B}$)$_2$, —C(=O)NHSO$_2$R$^{1B}$, —C(=O)NHSO$_2$N(R$^{1B}$)$_2$, C(=S)N(R$^{1B}$)$_2$, —SO$_2$R$^{1B}$, —SO$_2$OR$^{1B}$, —SO$_2$N(R$^{1B}$)$_2$, —SO$_2$—NHC(=O)OR$^{1B}$, —OC(=O)—N(R$^{1B}$)$_2$, —OC(=O)R$^{1B}$, —OC(=O)NHC(=O)R$^{1B}$, —OC(=O)NHSO$_2$R$^{1B}$, —OSO$_2$R$^{1B}$, or an aliphatic heteroaliphatic, aryl or heteroaryl moiety, or wherein $R^1$ and $R^2$ taken together are an alicyclic or heterocyclic moiety, or together are

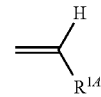

wherein each occurrence of $R^{1A}$ and $R^{1B}$ is independently hydrogen, an aliphatic, alicyclic, heteroaliphatic, heterocyclic, aryl, heteroaryl, alkylaryl or alkylheteroaryl moiety, —C(=O)R$^{1C}$, or —C(=O)NR$^{1C}$R$^{1D}$); wherein each occurrence of R$^{1C}$ and R$^{1D}$ is independently hydrogen, hydroxyl, or an aliphatic, heteroaliphatic, aryl, heteroaryl, alkylaryl or alkylheteroaryl moiety; and $R^{1E}$ is hydrogen, an aliphatic, alicyclic, heteroaliphatic, heterocyclic, aryl, heteroaryl, alkylaryl or alkylheteroaryl moiety, —CN, —OR$^{1C}$, —NR$^{1C}$R$^{1D}$ or —SO$_2$R$^{1C}$;

where $R^3$ is —C(=O)OR$^{3A}$, —C(=O)H, —CH$_2$OR$^{3A}$, —CH$_2$OC(=O)-alkyl, —C(=O)NH(R$^{3A}$), —CH$_2$X$^0$; wherein each occurrence of R$^{3A}$ is independently hydrogen, a protecting group, an aliphatic, alicyclic, heteroaliphatic, heteroalicyclic, aryl, heteroaryl, alkylaryl, alkylheteroaryl, heteroalkylaryl, heteroalkylheteroaryl moiety, or a pharmaceutically acceptable salt or ester, or R$^{3A}$, taken together with $R^1$ and $R^2$, forms a heterocyclic moiety; wherein X$^0$ is a halogen selected from F, Br or I;

$R^4$ for each occurrence, is independently hydrogen, halogen, —CN, —NO$_2$, an aliphatic, alicyclic, heteroaliphatic, heteroalicyclic, aryl, heteroaryl, alkylaryl or alkylheteroaryl moiety, or is GR$^{G1}$ wherein G is —O—, —S—, NR$^{G2}$—, —CO—, —SO—, —SO$_2$—, C(=O)O—, —C(=O)NR$^{G2}$—, C(=O)—, —NR$^{G2}$C(=O)— or —SO$_2$NR$^{G2}$—, and R$^{G1}$ and R$^{G2}$ are independently hydrogen, an aliphatic, alicyclic, heteroaliphatic, heteroalicyclic, aryl, heteroaryl, alkylaryl or alkylheteroaryl moiety;

n is an integer from 0-4;

AR$^1$ is a monocyclic or polycyclic aryl, heteroaryl, alkylaryl, alkylheteroaryl, alicyclic or heterocyclic moiety;

A, B, D and E are connected by either a single or double bond, as valency permits; wherein each occurrence of A, D and E is independently C=O, CR$^i$R$^{ii}$, NR$^i$, CR$^i$, N, O, S, —S(=O) or SO$_2$; wherein each occurrence of R$^i$ is independently hydrogen, halogen, —CN, —NO2, an aliphatic, alicyclic, heteroaliphatic, heteroalicyclic, aryl, heteroaryl, alkylaryl or alkylheteroaryl moiety, or is -GR$^{G1}$ wherein G is —O—, —S—, —NR$^{G2}$, —CO—, —SO—, —C(=O)O—, —C(=O)NR$^{G2}$—, —OC(=O)—, —NR$^{G2}$C(=O)— or —SO$_2$NR$^{G2}$—, and R$^{G1}$ and R$^{G2}$ are independently hydrogen, an aliphatic, alicyclic, heteroaliphatic, heteroalicyclic, aryl, heteroaryl, alkylaryl or alkylheteroaryl moiety, or any two adjacent occurrences of taken together, represent an alicyclic, heteroalicyclic, aryl, or heteroaryl moiety;

p is an integer from 0-4; and,

L is absent or is V—W—X—Y—Z, wherein each occurrence of V, W, X, Y and Z is independently absent, C=O, NR$^{L1}$, —O—, —C(R$^{L1}$)=, =C(R$^{L1}$)—, —C(R$^{L1}$)(R$^{L2}$), C(=N—O R$^{L1}$), C(=NR$^{L1}$), —N=, S(O)$_{0-2}$; a substituted or unsubstituted C$_{1-6}$ alkenylidene or C$_{2-6}$ alkenylidine chain wherein up to two non-adjacent methylene units are independently optionally replaced by —C(=O)—, —CO$_2$—, —C(=O)C(=O)—, —C(C=O)NR$^{L3}$—, —OC(=O)—, —OC(=O)NR$^{L3}$—, —NR$^{L3}$NR$^{L4}$—, —NR$^{L3}$NR$^{L4}$C(=O)—, —NR$^{L3}$C(=O)—, NR$^{L3}$CO$_2$—, NR$^{L3}$C(=O)NR$^{L4}$—, —S(=O)—, —SO$_2$—, —NR$^{L3}$SO$_2$—, —SO$_2$NR$^{L3}$, —NR$^{L3}$SO$_2$NR$^{L4}$, —O—, —S—, or —NR$^{L3}$—; wherein each occurrence of R$^{L3}$ and R$^{L4}$ is independently hydrogen, alkyl, heteroalkyl, aryl, heteroaryl or acyl; or an aliphatic, alicyclic, heteroaliphatic, heteroalicyclic, aryl, heteroaryl, alkylaryl or alkylheteroaryl moiety; and each occurrence of R$^{L1}$ and R$^{L2}$ is independently hydrogen, hydroxyl, protected hydroxyl, amino, protected amino, thio, protected thio, halogen, cyano, isocyanate, carboxy, carboxyalkyl, formyl, formyloxy, azido, nitro, ureido, thioureido, thiocyanato, alkoxy, aryloxy, mercapto, sulfonamido, benzamido, tosyl, or an aliphatic, alicyclic, heteroaliphatic, heteroalicyclic, aryl, heteroaryl, alkylaryl or alkylheteroaryl moiety, or wherein one or more occurrences of R$^{L1}$ and R$^{L2}$, taken together, or taken together with one of V, W, X, Y or Z form an alicyclic or heterocyclic moiety or form an aryl or heteroaryl moiety.

Some preferred embodiments of the method of the present invention are of Formula II:

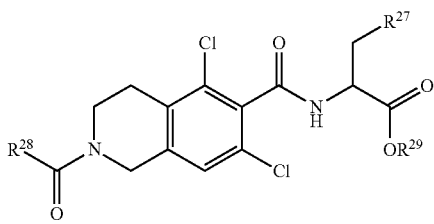

where R$^{28}$ is one of the following groups:

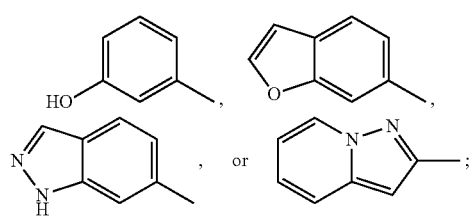

And R$^{27}$ is one of the following groups:

Formula II

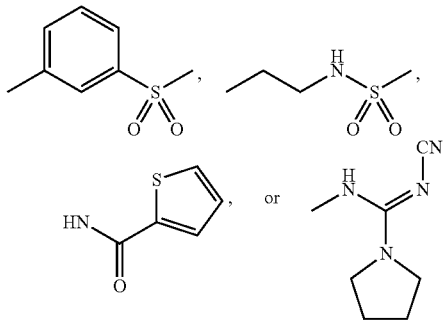

and R$^{29}$ is hydrogen, a pharmaceutically acceptable salt or ester.

Some preferred embodiments of the invention are compounds of the Formula II'

Formula II'

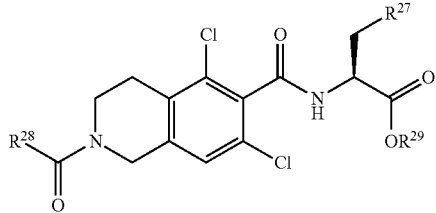

where the substitution is as in Formula II.

Some particularly preferred embodiments of compounds of the method of the present invention are compounds of Formulas IIA, IIB and IIC:

Formula IIA

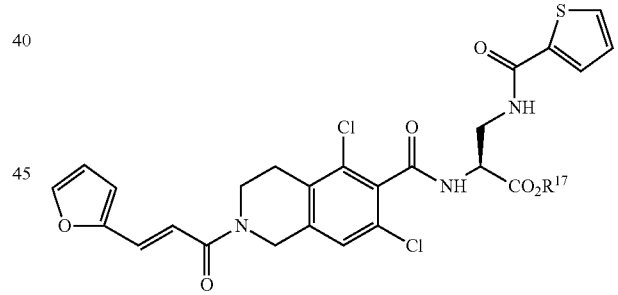

where R$^{17}$ respectively can be each be chosen from the group of hydrogen, pharmaceutically acceptable salts and esters.

Another set of preferred embodiments of compounds of the method of the invention are compounds of the Formula III:

Formula III

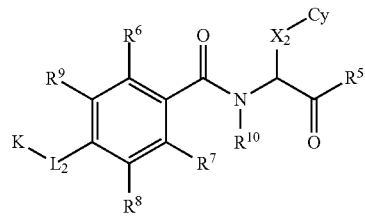

where Cy is an aromatic carbocycle, aromatic heterocycle or a non-aromatic carbocycle or heterocycle optionally substituted with hydroxyl (—OH), mercapto (—SH), thioalkyl, halogen (e.g. F, Cl, Br, I), oxo (=O), thio (=S), amino, aminoalkyl, amidine (—C(NH)—NH$_2$), guanidine (—NH$_2$—C(NH)—NH$_2$), nitro, alkyl or alkoxy. In a particular embodiment, Cy is a 3-5 member ring. In a preferred embodiment, Cy is a 5- or 6-member non-aromatic heterocycle optionally substituted with hydroxyl, mercapto, halogen (preferably F or Cl), oxo (=O), thio (=S), amino, amidine, guanidine, nitro, alkyl or alkoxy. In a more preferred embodiment, Cy is a 5-member non-aromatic heterocycle optionally substituted with hydroxyl, oxo, thio, Cl, $C_{1-4}$ alkyl (preferably methyl), or $C_{1-4}$ alkanoyl (preferably acetyl, propanoyl or butanoyl). More preferably the non-aromatic heterocycle comprises one or heteroatoms (N, O or S) and is optionally substituted with hydroxyl, oxo, mercapto, thio, methyl, acetyl, propanoyl or butyl. In particular embodiments the non-aromatic heterocycle comprises at least one nitrogen atom that is optionally substituted with methyl or acetyl. In a particularly preferred embodiment, the non-aromatic heterocycle is selected from the group consisting of piperidine, piperazine, morpholine, tetrahydrofuran, tetrahydrothiophene, oxazolidine, thiazolidine optionally substituted with hydroxy, oxo, mercapto, thio, alkyl or alkanoyl. In a most preferred embodiment Cy is a non-aromatic heterocycle selected from the group consisting of tetrahydrofuran-2-yl, thiazolidin-5-yl, thiazolidin-2-one-5-yl, and thiazolidin-2-thione-5-yl and cyclopropapyrrolidine. In a preferred embodiment, Cy is a 5- or 6-member aromatic carbocycle or heterocycle optionally substituted with hydroxyl, mercapto, halogen (preferably F or Cl), oxo (=O), thio (=S), amino, amidine, guanidine, nitro, alkyl or alkoxy. In a more preferred embodiment, Cy is a 5-member aromatic carbocycle or heterocycle optionally substituted with hydroxyl, oxo, thio, Cl, $C_{1-4}$ alkyl (preferably methyl), or $C_{1-4}$ alkanoyl (preferably acetyl, propanoyl or butanoyl). More preferably the aromatic or heterocycle comprises one or heteroatoms (N, O or S) and is optionally substituted with hydroxyl, oxo, mercapto, thio, methyl, acetyl, propanoyl or butyl.

In another preferred embodiment Cy is a 3-6 member carbocycle optionally substituted with hydroxyl, mercapto, halogen, oxo, thio, amino, amidine, guanidine, alkyl, alkoxy or acyl. In a particular embodiment the carbocycle is saturated or partially unsaturated. In particular embodiments Cy is a carbocycle selected from the group consisting of cyclopropyl, cyclopropenyl, cyclobutyl, cyclobutenyl, cyclopentyl, cyclopentenyl, cyclohexyl and cyclohexenyl. $X_2$ is a $C_{1-5}$ divalent hydrocarbon linker optionally having one or more carbon atoms replaced with N, O, S, SO or SO$_2$ and optionally being substituted with hydroxyl, mercapto, halogen, amino, aminoalkyl, nitro, oxo or thio. In a preferred embodiment $X_2$ will have at least one carbon atom. Replacements and substitutions may form an amide moiety (—NRC(=O) or —C(=O)NR—) within the hydrocarbon chain or at either or both ends. Other moieties include sulfonamide (—NRSO$_2$— or —SO$_2$NR), acyl, ether, thioether and amine. In a particularly preferred embodiment $X_2$ is the group CH$_2$ NR$^{10}$—C(O) wherein the carbonyl —C(O)— portion thereof is adjacent (i.e. covalently bound) to Cy and $R^{10}$ is alkyl i.e. methyl and more preferably H.

K is a carbocycle or heterocycle optionally substituted with hydroxyl, mercapto, halogen, oxo, thio, a hydrocarbon, a halo-substituted hydrocarbon, amino, amidine, guanidine, cyano, nitro, alkoxy or acyl. In particular embodiment, K is aryl or heteroaryl optionally substituted with halogen or hydroxyl. In a particularly preferred embodiment, K is phenyl, furan-2-yl, thiophene-2-yl, phenyl substituted with a halogen (preferably Cl) or hydroxyl, preferably at the meta position. $L_2$ is a divalent hydrocarbon optionally having one or more carbon atoms replaced with N, O, S, SO or SO$_2$ and optionally being substituted with hydroxyl, halogen oxo, or thio; or three carbon atoms of the hydrocarbon are replaced with an amino acid residue. Preferably $L_2$ is less than 10 atoms in length and more preferably 5 or less and most preferably 5 or 3 atoms in length. In particular embodiments, $L_2$ is selected from the group consisting of CH=CH—C(O) NR$^{10}$—CH$_2$—, —CH$_2$—NR$^{10}$C(O)—, —C(O)—NR$^{10}$CH$_2$—, —CH(OH)—(CH$_2$)$_2$—, —(CH$_2$)$_2$—CH (OH)—, —(CH$_2$)$_3$—, —C(O)—NR$^{10}$—CH (R$_7$)—C(O) NR$^{10}$—, —NR$^{10}$C(O)—CH(R$^{16}$)—NR$^{10}$—C(O)—, —CH (OH)CH$_2$—O— and —CH(OH)—CF$_2$—CH$_2$— wherein each R$^{10}$ is independently H or alkyl and R$^{16}$ is an amino acid side chain. Preferred amino acid side chains include non-naturally occurring side chains such as phenyl or naturally occurring side chains. Preferred side chains are those from Phe, Tyr, Ala, Gln and Asn. In a preferred embodiments $L_2$ is —CH=CH—C(O)—NR$^{10}$CH$_2$— wherein the —CH=CH— moiety thereof is adjacent (i.e. covalently bound) to K. In another preferred embodiment, $L_2$ is —CH$_2$—NR$^{10}$—C(O)— wherein the methylene moiety (—CH$_2$—) thereof is adjacent to K.

$R^5$ is H, OH, amino, O-carbocycle or alkoxy optionally substituted with amino, a carbocycle, a heterocycle, or a pharmaceutically acceptable salt or ester. In a preferred embodiment, $R^5$ is H, phenyl or $C_{1-4}$ alkoxy optionally substituted with a carbocycle such as phenyl. In a particular embodiment $R^5$ is H. In another particular embodiment $R^5$ is methoxy, ethoxy, propyloxy, butyloxy, isobutyloxy, s-butyloxy, t-butyloxy, phenoxy or benzyloxy. In yet another particular embodiment $R^5$ is NH$_2$. In a particularly preferred embodiment $R^5$ is ethoxy. In another particularly preferred embodiment $R^5$ is isobutyloxy. In another particularly preferred embodiment $R^5$ is alkoxy substituted with amino, for example 2-aminoethoxy, N-morpholinoethoxy, N,N-dialkyaminoethoxy, quaternary ammonium hydroxy alkoxy (e.g. trimethylammoniumhydroxyethoxy).

$R^{6-9}$ are independently H, hydroxyl, mercapto, halogen, cyano, amino, amidine, guanidine, nitro or alkoxy; or $R^7$ and $R^8$ together form a fused carbocycle or heterocycle optionally substituted with hydroxyl, halogen, oxo, thio, amino, amidine, guanidine or alkoxy. In a particular embodiment $R^6$ and $R^7$ are independently H, F, Cl, Br or I. In another particular embodiment, $R^8$ and $R^9$ are both H. In another particular embodiment, one of $R^6$ and $R^7$ is a halogen while the other is hydrogen or a halogen. In a particularly preferred embodiment, $R^7$ is Cl while $R^6$, $R^8$ and $R^9$ are each H. In another particularly preferred embodiment, $R^6$ and $R^7$ are both Cl while $R^8$ and $R^9$ are both H.

$R^{10}$ is H or a hydrocarbon chain optionally substituted with a carbocycle or a heterocycle. In a preferred embodiment, $R^{10}$ is H or alkyl i.e. methyl, ethyl, propyl, i-butyl, s-butyl or t-butyl. In a particular embodiment $R^{10}$ is H.

Further preferred embodiments of the method of the present invention are compounds of the Formula IV:

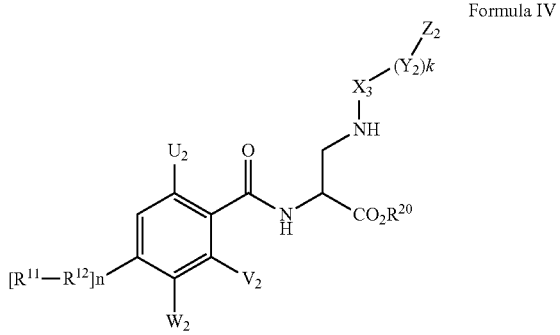

Formula IV where R[11] is a group of the formula

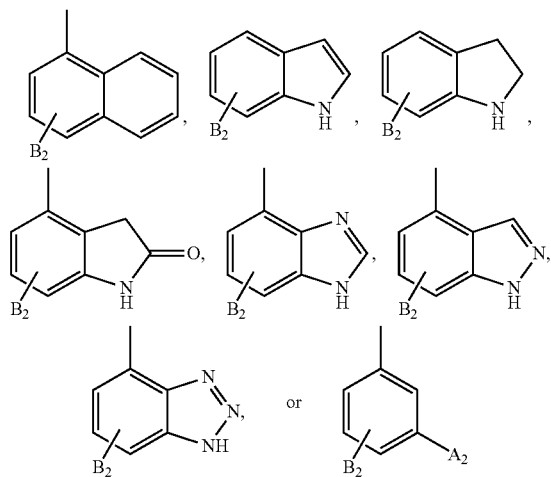

where A is hydrogen, hydroxy, amino, or halogen and B is amino, carboxy, hydrogen, hydroxy, cyano, trifluoromethyl, halogen, lower alkyl, or lower alkoxy;

R[12] is a group of the formula:

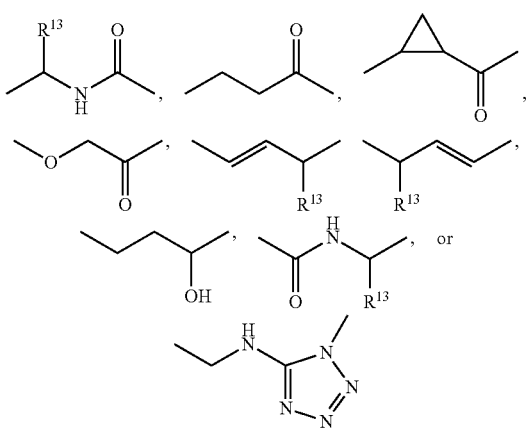

where R[13] is hydrogen, carboxy, or lower alkyl; n is 0 or 1; $U_2$, $V_2$, and $W_2$ are independently hydrogen, halogen, or lower alkyl provided $U_2$ and $V_2$ are not both hydrogen; $X_3$ is carbonyl, phenyl-substituted lower alkylene, imino, substituted imino, or sulfonyl; $Y_2$ is lower alkylene which may be substituted by one or more of amino, substituted amino, lower alkyl, or cyclo lower alkyl, or $Y_2$ is lower alkenylene or lower alkylenethio;

k is 0 or 1; when k is 1, $Z_2$ is hydrogen, lower alkylthio, —COOH, —CONH$_2$, amino; and when k is 0 or 1, $Z_2$ is 1-adamantyl, diphenylmethyl, 3-[[(5-chloropyridin-2-yl)amino]carbonyl]pyrazin-2-yl, hydroxy, phenylmethoxy, 2-chloro-4-[[[(3-hydroxyphenyl) methyl]amino]carbonyl] phenyl, [2,6-dichlorophenyl) methoxy]phenyl; further when k is 0 or 1, $Z_2$ may be cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, alkoxycarbonyl, acetoxy, or also in addition with amino lower alkyl; and R[20] is hydrogen, a pharmaceutically acceptable salt or ester.

A preferred embodiment of compounds of Formula IV has stereochemistry as indicated in Formula IV:

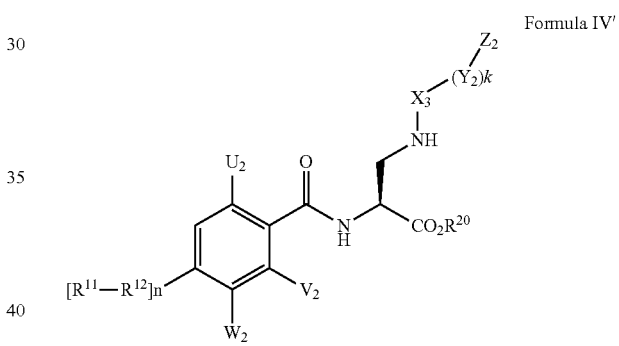

Formula IV'

Another set of preferred embodiments of the compounds of the method of the present invention are compounds of Formula V:

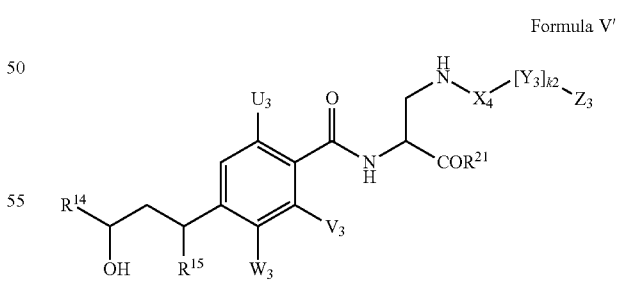

Formula V' where R[14] is a group of the formula:

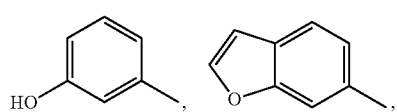

-continued

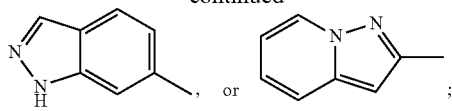

where $R^{15}$ is hydrogen, carboxy, or lower alkyl; $U_3$, $V_3$, and $W_3$ are independently hydrogen, halogen; or $U_3$, $V_3$, and $W_3$ are lower alkyl provided that $U_3$ and $V_3$ are not both hydrogen; $X_4$ is carbonyl, phenyl-substituted lower alkylene, imino, substituted imino which includes cyano, or sulfonyl; $Y_3$ is lower alkenylene, lower alkylenethio, or is lower alkylene which may be substituted by amino, acetylamino, or cyclo-lower alkyl;

$k_2$ is 0 or 1; when $k_2$ is 1, Z is hydrogen, lower alkylthio, —COOH, —CONH$_2$—, or amino; when $k_2$ is 0 or 1, $Z_3$ is 1-adamantyl, diphenylmethyl, 3-[[(5-chloropyridin-2-yl)amino]carbonyl]pyrazin-2-yl; and when $k_2$ is 0 or 1, Z may be cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, carboxy, alkoxycarbonyl, or acetoxy; and, $R^{21}$ is hydrogen, pharmaceutically acceptable salts or esters thereof.

A preferred embodiment of compounds of Formula V has the stereochemistry as indicated in Formula V':

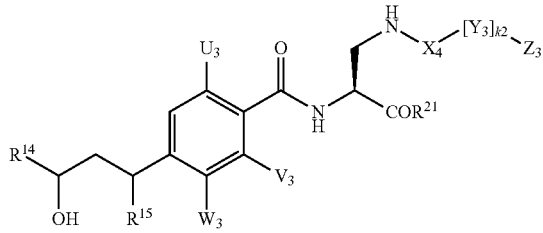

Formula V'

Another class of preferred compounds of the method are represented by Formula VI

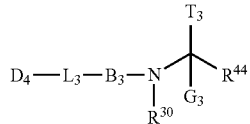

Formula VI where $D_4$ is a mono-, bi-, or tricyclic saturated, unsaturated, or aromatic ring, each ring having 5-, 6- or 7 atoms in the ring where the atoms in the ring are carbon or from one to four heteroatoms selected from the group nitrogen, oxygen, and sulfur, where any carbon or sulfur ring atom may optionally be oxidized, each ring substituted with 0-3 $R^{31}$;
$L_3$ is a bivalent linking group selected from the group
-$L^3$-$L^2$-$L^1$-,
-$L^4$-$L^3$-$L^2$-$L^1$- and
-$L^5$-$L^4$-$L^3$-$L^2$-$L^1$-, where $L^1$ is selected from oxo (—O—), S(O)$_s$, C(=O), CR$^{32}$, R$^{32'}$, CR$^{32}$ het, NR$^{30}$ and N,
$L^2$ is selected from oxo (—O—), S(O)$_s$, C(=O), C(=N—O—R$^{33}$),
CR$^{34}$R$^{34'}$, CR$^{34}$, het NR$^{30}$ and N,
$L^3$ is selected from oxo (—O—), S(O)$_s$, C(=O), C(=N—O—R$^{33}$), CR$^{35}$R$^{35'}$, CR$^{35}$, het NR$^{30}$ and N,
$L^4$ is absent or is selected from oxo (—O—), S(O)$_s$, C(=O), C(=N—O—R$^{33}$), CR$^{36}$R$^{36'}$, CR$^{36}$, NR$^{30}$ and N,
$L^5$ is absent or selected from oxo (—O—), S(O)$_s$, C(=O), CR$^{37}$R$^{37'}$, CR$^{37}$, NR$^{30}$ and N, provided that only one of $L^1$-$L^3$ may be het and that when one of $L^1$-$L^3$ is het the other $L^1$-$L^5$ may be absent,
where
$R^{32}$, $R^{32'}$, $R^{34}$, $R^{34'}$, $R^{35}$, $R^{35'}$, $R^{36}$, $R^{36'}$, $R^{37}$ and $R^{37'}$ each are independently selected from $R^{38}$, $R^{39}$ and U-Q-V—W,
optionally, $R^{24}$ and $R^{34'}$ separately or together may form a saturated, unsaturated or aromatic fused ring with $B_3$ through a substituent RP on B, the fused ring containing 5, 6 or 7 atoms in the ring and optionally containing 1-3 heteroatoms selected from the group O, S and N, where any S or N may optionally be oxidized;
optionally, $R^{35}$ and $R^{35'}$ separately or together and $R^{36}$ and $R^{36'}$ separately or together may form a saturated, unsaturated or aromatic fused ring with $D_3$ through a substituent $R^{31}$ on $D_3$, the fused ring containing 5, 6 or 7 atoms in the ring and optionally containing 1-3 heteroatoms selected from the group O, S and N, where any S or N may optionally be oxidized;
also optionally, each $R^{32}$—$R^{37}$, NR$^{30}$ or N in $L^1$-$L^5$ together with any other $R^{32}$—$R^{37}$, NR$^{30}$ or N in $L^1$-$L^5$ may form a 5, 6 or 7 member homo- or heterocycle either saturated, unsaturated or aromatic optionally containing 1-3 additional heteroatoms selected from N, O and S, where any carbon or sulfur ring atom may optionally be oxidized, each cycle substituted with 0-3 $R^{31}$; and where s is 0-2; B is selected from the group

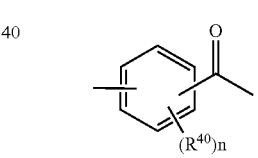

where
is a fused hetero- or homocyclic ring containing 5, 6 or 7 atoms, the ring being unsaturated, partially saturated or aromatic, the heteroatoms selected from 1-3 O, S and N,
$Y_3$ is selected from CH and NR$^{30}$; n is 0-3:
$G_3$ is selected from hydrogen and $C_1$-$C_6$alkyl, optionally G taken together with T may form a $C_3$-$C_6$cycloalkyl optionally substituted with —V—W;
$T_3$ is selected from the group
a naturally occurring α-amino-acid side chain,
and $U_4$-$Q_4$-$V_4$—$W_4$;
$U_4$ is an optionally substituted bivalent radical selected from the group $C_1$-$C_6$alkyl, $C_0$-$C_6$alkyl-Q, $C_2$-$C_6$alkenyl-Q, and $C_2$-$C_6$alkynyl-Q:
where the substituents on any alkyl, alkenyl or alkynyl are 1-3 $R^{38}$;
$Q_4$ is absent or is selected from the group —O—, —S(O)$_s$—, —SO$_2$—N(R$^{30}$)—, —N(R$^{30}$)—, —N(R$^{30}$)—C(=O)—, —N($R^{30}$)—C(=O)—N($R^{30}$)—, —N($R^{30}$)—C(=O)—O—, N($R^{30}$)—SO$_2$—, —C(=O)—, —C(=O)—O—, -het-, —C(=O)—N($R^{30}$)—, —O—C(=O)—N($R^{30}$)—, —PO(O$R^{30}$)O— and —P(O)O—;
where
is 0-2 and
het is a mono- or bicyclic 5, 6, 7, 9 or 10 member heterocyclic ring, each ring containing 1-4 heteroatoms selected from N, O and S, where the heterocyclic ring may be saturated, partially saturated, or aromatic and any N or S being optionally oxidized, the heterocyclic ring being substituted with 0-3 $R^{41}$;
$V_4$ is absent or is an optionally substituted bivalent group selected from $C_1$-$C_6$alkyl, $C_3$-$C_8$cycloalkyl, $C_0$-$C_6$alkyl-$C_6$-$C_{10}$aryl, and $C_0$-$C_6$alky-het;
where the substituents on any alkyl are 1-3 $R^{38}$ and the substituents on any aryl or het are 1-3 $R^{31}$;
$W_4$ is selected from the group
hydrogen, O$R^{33}$, S$R^{42}$, N$R^{30}R^{30}$, NH—C(=O)—O—$R^{43}$, NH—C(=O)—NR″R″, NH—C(=O)—$R^{43}$, NH—SO$_2$—$R^{37}$, NH—SO$_2$—N$R^{30}R^{30}$, NH—SO$_2$—NH—C(=O)—$R^{43}$, NH—C(=O)—NH—SO$_2$—$R^{37}$, C(=O)—NH—C(=O)—O—$R^{43}$, C(=O)—NH—C(=O)—$R^{43}$, C(=O)—NH—C(=O)—N$R^{30}R^{30'}$, C(=O)—NH—SO$_2$—$R^{37}$, C(=O)—NH—SO$_2$—N$R^{30}R^{30'}$, C(=S)—N$R^{3}$O$R^{30'}$, SO$_2$—$R^{37}$, SO$_2$—O—$R^{37}$, SO$_2$—N$R^{37}R^{37'}$, SO$_2$—NH—C(=O)—O—$R^{43}$, SO$_2$—NH—C(=O)N$R^{30}R^{30'}$, SO$_2$—NH—C(=O)$R^{43}$, O—C(=O)—N$R^{30}R^{30'}$, O—C(=O)$R^{43}$, O—C(=O)—NH—C(=O)—$R^{43}$, O—C(=O)—NH—SO$_2R^{46}$ and O—SO$_2$—$R^{37}$;
$R^{44}$ is selected from C(=O)—$R^{45}$, C(=O)H, CH$_2$(OH), and CH$_2$O—C(=O)—$C_1$-$C_6$alkyl;
$R^{38}$ is $R^{38'}$ or $R^{38''}$ substituted with 1-3 $R^{38}$; where
$R^{38'}$ is selected from the group
hydrogen, halo(F, Cl, Br, I), cyano, isocyanate, carboxy, carboxy-$C_1$-$C_{11}$alkyl, amino, amino-$C_1$-$C_8$alkyl, aminocarbonyl, carboxamido, carbamoyl, carbamoyloxy, formyl, formyloxy, azido, nitro, imidazoyl, ureido, thioureido, thiocyanato, hydroxy, $C_1$-$C_6$alkoxy, mercapto, sulfonamido, het, phenoxy, phenyl, benzamido, tosyl, morpholino, morpholinyl, piperazinyl, piperidinyl, pyrrolinyl, imidazolyl, and indolyl;
$R^{38''}$ is selected from the group
$C_0$-$C_{10}$alkyl-Q-$C_0$-$C_6$alkyl, $C_0$-$C_{10}$alkenyl-Q-$C_0$-$C_6$alkyl, $C_0$-$C_{10}$alkynyl-Q-$C_0$-$C_6$alkyl, $C_3$-$C_{11}$cycloalkyl-Q-$C_0$-$C_6$alkyl, $C_3$-$C_{10}$cycloalkenyl-Q-$C_0$-$C_6$alkyl, $C_1$-$C_6$alkyl-$C_6$-$C_{12}$ aryl-Q-$C_0$-$C_6$alkyl, $C_6$-$C_{10}$ aryl-$C_1$-$C_6$alkyl-Q-$C_0$-$C_6$alkyl, $C_0$-$C_6$alkyl-het-Q-$C_0$-$C_6$alkyl, $C_0$-$C_6$alkyl-Q-het-$C_0$-$C_6$alkyl, het-$C_0$-$C_6$alkyl-Q-$C_0$-$C_6$alkyl, $C_0$-$C_6$alkyl-Q-$C_6$-$C_{12}$aryl, and -Q-$C_1$-$C_6$alky;
$R^{43}$ is selected from hydrogen and substituted or unsubstituted $C_1$-$C_{10}$alkyl, $C_2$-$C_{10}$alkenyl, $C_2$-$C_{10}$alkynyl, $C_3$-$C_{11}$cycloalkyl, $C_3$-$C_{10}$cycloalkenyl, $C_1$-$C_6$alkyl-$C_6$-$C_{12}$aryl, $C_6$-$C_{10}$aryl-$C_1$-$C_6$alkyl, $C_1$-$C_6$alkyl-het, het-$C_1$-$C_6$ alkyl, $C_6$-$C_{12}$aryl and het, where the substituents on any alkyl, alkenyl or alkynyl are 1-3 $R^{38}$ and the substituents on any aryl or het are 1-3 $R^{31}$;
$R^{31}$ is selected from $R^{40}$ and $R^{41}$;
$R^{41}$ is selected from the group
OH, OCF$_3$, O$R^{43}$, S$R^{42}$, halo(F, Cl. Br, I), CN, isocyanate, NO$_2$, CF$_3$, $C_0$-$C_6$alkyl-N$R^{30}R^{30'}$, $C_0$-$C_6$alkyl-C(=O)—N$R^{30}R^{30'}$, $C_0$-$C_6$alkyl-C(=O)—$R^{38}$, $C_1$-$C_8$alkyl, $C_1$-$C_8$alkoxy, $C_2$-$C_8$alkenyl, $C_2$-$C_8$alkynyl, $C_3$-$C_6$cycloalkyl, $C_3$-$C_6$cycloalkenyl, $C_1$-$C_6$alkyl-phenyl, phenyl-$C_1$-$C_6$alkyl, $C_1$-$C_6$alkyloxycarbonyl, phenyl-$C_0$-$C_6$alkyloxy, $C_1$-$C_6$alkyl-het, het-$C_1$-$C_6$alkyl, SO$_2$-het, —O—$C_6$-$C_{12}$aryl, —SO$_2$—$C_6$-$C_{12}$aryl, SO$_2$—$C_1$-$C_6$alkyl and het,
where any alkyl, alkenyl or alkynyl may optionally be substituted with 1-3 groups selected from OH, halo(F, Cl, Br, I), nitro, amino and aminocarbonyl and the substituents on any aryl or het are 1-2 hydroxy, halo(F, Cl, Br, I), CF$_3$, $C_1$-$C_6$alkyl, $C_6$alkoxy, nitro and amino;
$R^{42}$ is selected from S—$C_1$-$C_6$alkyl, C(=O)—$C_1$-$C_6$alkyl, C(=O)—N$R^{30}R^{30'}$, $C_1$-$C_6$alkyl, halo(F, Cl, Br, I)—$C_1$-$C_6$alkyl, benzyl and phenyl;
$R^{30}$ is selected from the group $R^{43}$, NH—C(=O)—O—$R^{43}$, NH—C(=O)—$R^{43}$, NH—C(=O)—NH$R^{43}$, NH—SO$_2$—$R^{46}$, NH—SO$_2$—NH—C(=O)—$R^{43}$, NH—C(=O)—NH—SO$_2$—$R^{37}$, C(=O)—O—$R^{43}$, C(=O)—$R^{43}$, C(=O)—NH$R^{43}$, C(=O)—NH—C(=O)—O—$R^{43}$, C(=O)—NH—C(=O)—$R^{43}$, C(=O)—NH—SO$_2$—$R^{46}$, C(=O)—NH—SO$_2$—NH$R^{37}$, SO$_2$—$R^{37}$, SO$_2$—O—$R^{37}$, SO$_2$—N($R^{43}$)$_2$, SO$_2$—NH—C(=O)—O—$R^{43}$, SO$_2$—NH—C(=O)—O—$R^{43}$ and SO$_2$—NH—C(=O)—$R^{43}$;
$R^{30'}$ is selected from hydrogen, hydroxy and substituted or unsubstituted $C_1$-$C_{11}$alkyl, $C_1$-$C_{11}$alkoxy, $C_2$-$C_{10}$alkenyl, $C_2$-$C_{10}$alkynyl, $C_3$-$C_{11}$cycloalkyl, $C_3$-$C_{10}$cycloalkenyl, $C_1$-$C_6$alkyl-$C_6$-$C_{12}$aryl, $C_6$-$C_{10}$aryl-$C_1$-$C_6$ alkyl, $C_6$-$C_{10}$aryl-$C_0$-$C_6$alkyloxy, $C_1$-$C_6$alkyl-het, het-$C_1$-$C_6$alkyl, $C_6$-$C_{12}$aryl, het, $C_1$-$C_6$alkylcarbonyl, $C_1$-$C_8$alkoxycarbonyl, $C_3$-$C_8$cycloalkylcarbonyl, $C_3$-$C_8$cycloalkoxycarbonyl, $C_6$-$C_{11}$aryloxycarbonyl, $C_7$-$C_{11}$arylalkoxycarbonyl, heteroarylalkoxycarbonyl, heteroarylalkylcarbonyl, heteroarylcarbonyl, heteroarylalkylsulfonyl, heteroarylsulfonyl, $C_1$-$C_6$alkylsulfonyl, and $C_6$-$C_{10}$arylsulfonyl, where the substituents on any alkyl, alkenyl or alkynyl are 1-3 $R^{38}$ and the substituents on any aryl, het or heteroaryl are 1-3 $R^{31}$;
$R^{30}$ and $R^{30'}$ taken together with the common nitrogen to which they are attached may from an optionally substituted heterocycle selected from morpholinyl, piperazinyl, thiamorpholinyl, pyrrolidinyl, imidazolidinyl, indolinyl, isoindolinyl, 1,2,3,4-tetrahydro-quinolinyl, 1,2,3,4-tetrahydro-isoquinolinyl, thiazolidinyl and azabicyclononyl, where the substituents are 1-3 $R^{38}$;
$R^{33}$ is selected from hydrogen and substituted or unsubstituted $C_1$-$C_6$alkyl, $C_1$-$C_6$alkylcarbonyl, $C_2$-$C_6$alkenyl, $C_2$-$C_6$alkynyl, $C_3$-$C_8$cycloalkyl and benzoyl, where the substituents on any alkyl are 1-3 $R^{38}$ and the substituents on any aryl are 1-3 $R^{40}$;
$R^{40}$ is selected from the group OH, halo(F, Cl. Br, I), CN, isocyanate, O$R^{43}$, S$R^{42}$, SO$R^{43}$, NO$_2$, CF$_3$, $R^{43}$, N$R^{30}R^{30'}$, N$R^{30}$C(=O)—O—$R^{43}$, NRC(=O)—$R^{43}$, $C_0$-$C_6$alkyl-SO$_2$—$R^{43}$, $C_0$-$C_6$alkyl-SO$_2$—N$R^{30}R^{30'}$, C(=O)—$R^{43}$, O—C(=O)—$R^{43}$, C(=O)—O—$R^{43}$, and C(=O)—N$R^{30}R^{30'}$, where the substituents on any alkyl, alkenyl or alkynyl are 1-3 $R^{38}$ and the substituents on any aryl or het are 1-3 $R^{31}$;
$R^{46}$ is a substituted or unsubstituted group selected from $C_1$-$C_8$alkyl, $C_2$-$C_8$alkenyl, $C_2$-$C_8$alkynyl, $C_3$-$C_8$cycloalkyl, $C_3$-$C_6$cycloalkenyl, $C_0$-$C_6$alkyl-phenyl, phenyl-$C_0$-$C_6$alkyl, $C_0$-$C_6$alkyl-het and het-$C_0$-$C_6$alkyl,
where the substituents on any alkyl, alkenyl or alkynyl are 1-3 $R^{38}$ and the substituents on any aryl or het are 1-3 $R^{31}$;
$R^{45}$ is a substituted or unsubstituted group selected from hydroxy, $C_1$-$C_{11}$alkoxy, $C_3$-$C_{12}$cycloalkoxy, $C_8$-$C_{12}$aralkoxy, $C_8$-$C_{12}$arcycloalkoxy, $C_6$-$C_{10}$aryloxy, $C_3$-$C_{10}$ alkylcarbonyloxyalkyloxy, $C_3$-$C_{10}$ alkoxycarbonyloxyalkyloxy, $C_3$-$C_{10}$alkoxycarbonylalkyloxy, $C_5$-$C_{10}$cycloalkylcarbonyloxyalkyloxy, $C_5$-$C_{10}$cycloalkoxycarbonyloxyalkyloxy, $C_5$-$C_{10}$cycloalkoxycarbonylalkyloxy, $C_8$-$C_{12}$aryloxycarbonylalkyloxy, $C_8$-$C_{12}$aryloxycarbonyloxyalkyloxy, $C_8$-$C_{12}$arylcarbonyloxyalkyloxy, $C_5$-$C_{10}$alkoxyalkylcarbonyloxyalkyloxy, ($R^{30}$)($R^{30}$)N($C_1$-$C_{10}$alkoxy)-,

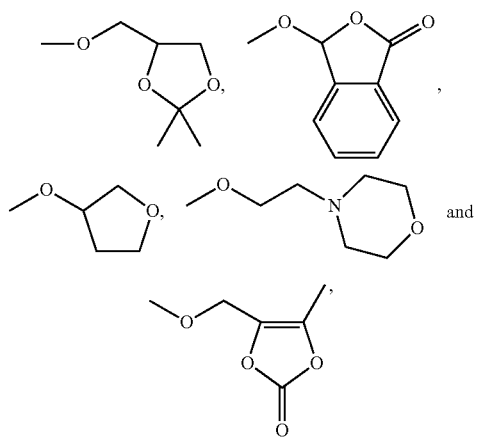

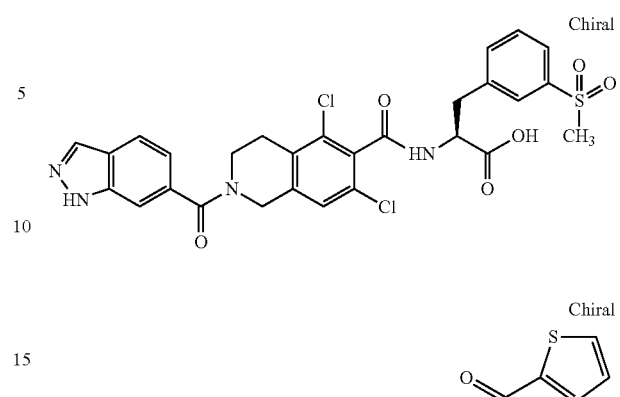

where the substituents on any alkyl, alkenyl or alkynyl are 1-3 $R^{38}$ and the substituents on any aryl or het are 1-3 $R^{31}$ and pharmaceutically acceptable salts thereof.

Compounds of Formulas I-VI also include pharmaceutically acceptable salts, and esters including pro-drug compounds of Formula I-VI, where $R^{3,4}$, $R^5$, $R^{10}$, $R^{17}$, $R^{18}$, $R^{19}$, $R^{20}$, $R^{21}$, $R^{29}$, and a carboxylic ester at $R^{44}$ may be lower alkyl or —$CH_2CH_2$—$R^{22}$ where $R^{22}$ is one of the following:

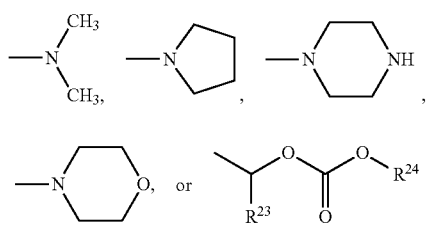

where $R^{23}$ is hydrogen or methyl and $R^{24}$ is lower alkyl or lower cycloalkyl.

A preferred embodiment of compounds of Formula VI has the stereochemistry indicated in Formula VI'.

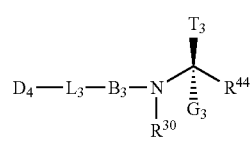

Formula VI'

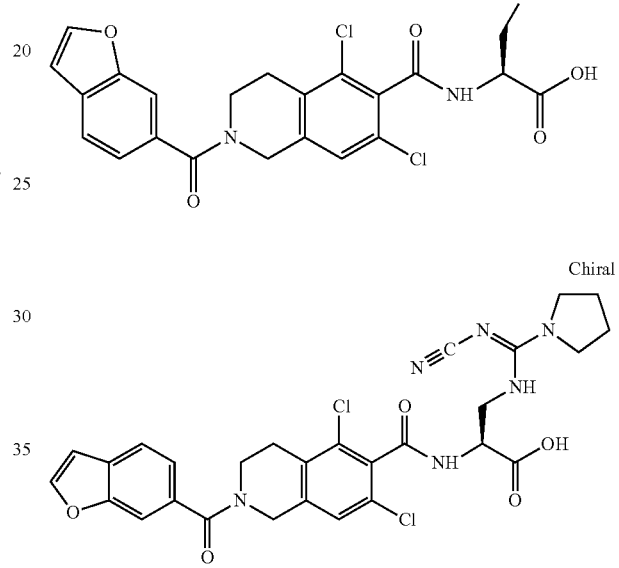

Some of the compounds described herein may comprise one or more asymmetric centers, and thus may comprise individual stereoisomers, individual diastereomers and any mixtures therein. Further, compounds of the invention may contain geometric isomers of double bonds, comprising Z and E isomers, and may be present as pure geometric isomers or mixtures thereof In some preferred embodiments, the methods of the present invention are performed with the following compounds or a pharmaceutically acceptable salt or ester thereof:

Compounds of the present invention include the following compounds or a pharmaceutically acceptable salt or ester thereof:

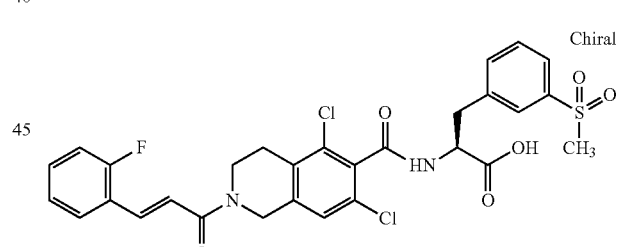

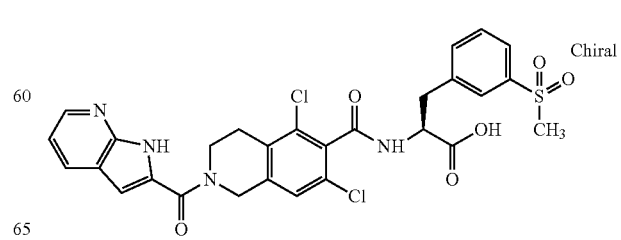

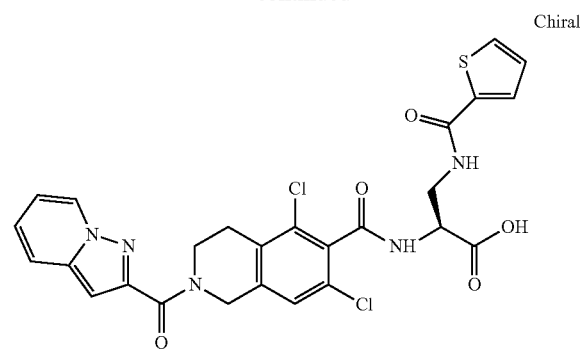
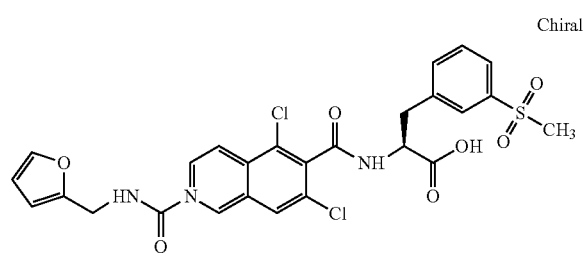
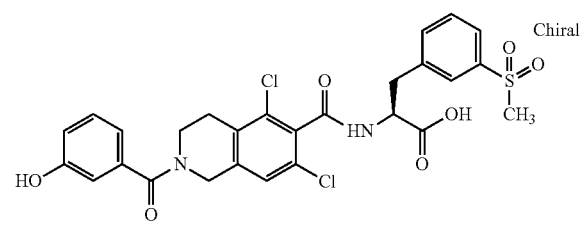
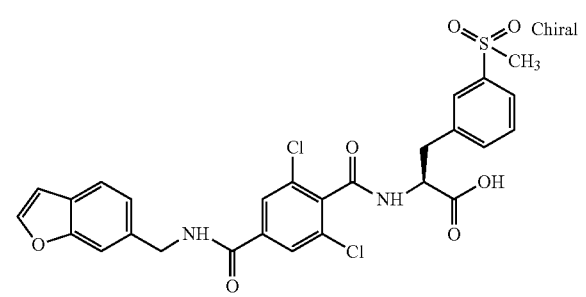
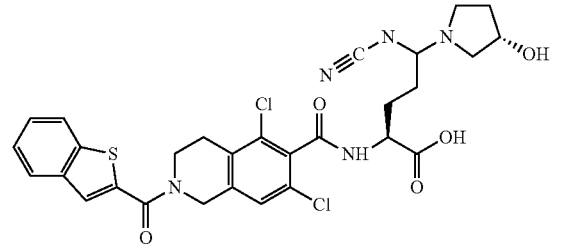
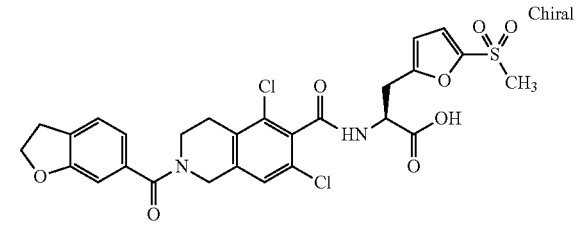
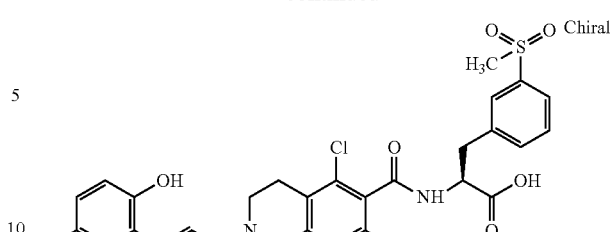
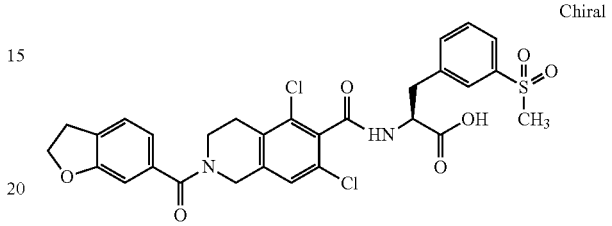
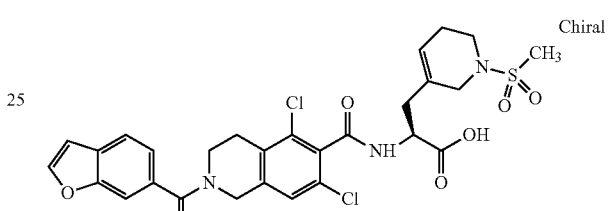
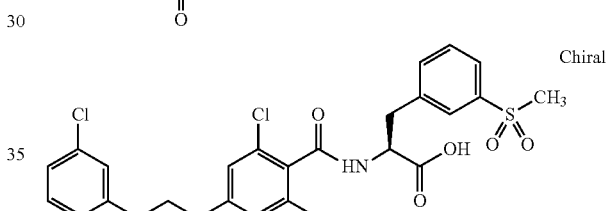
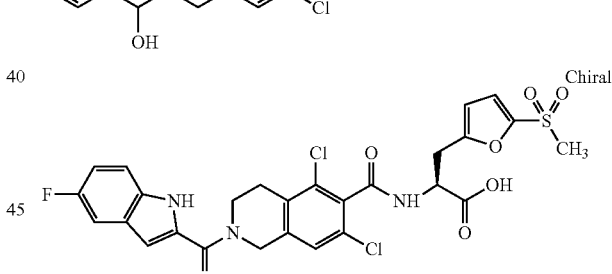
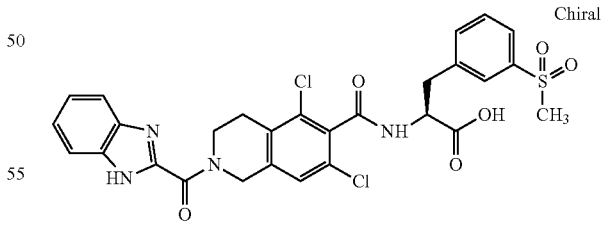
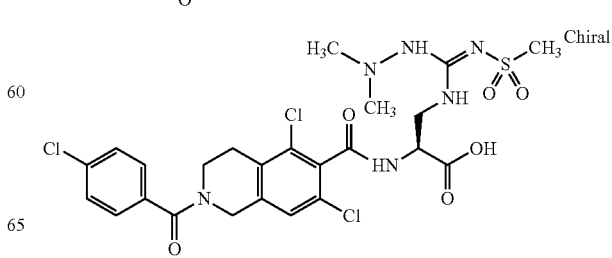

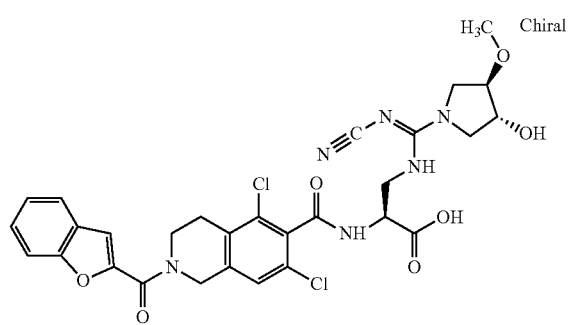
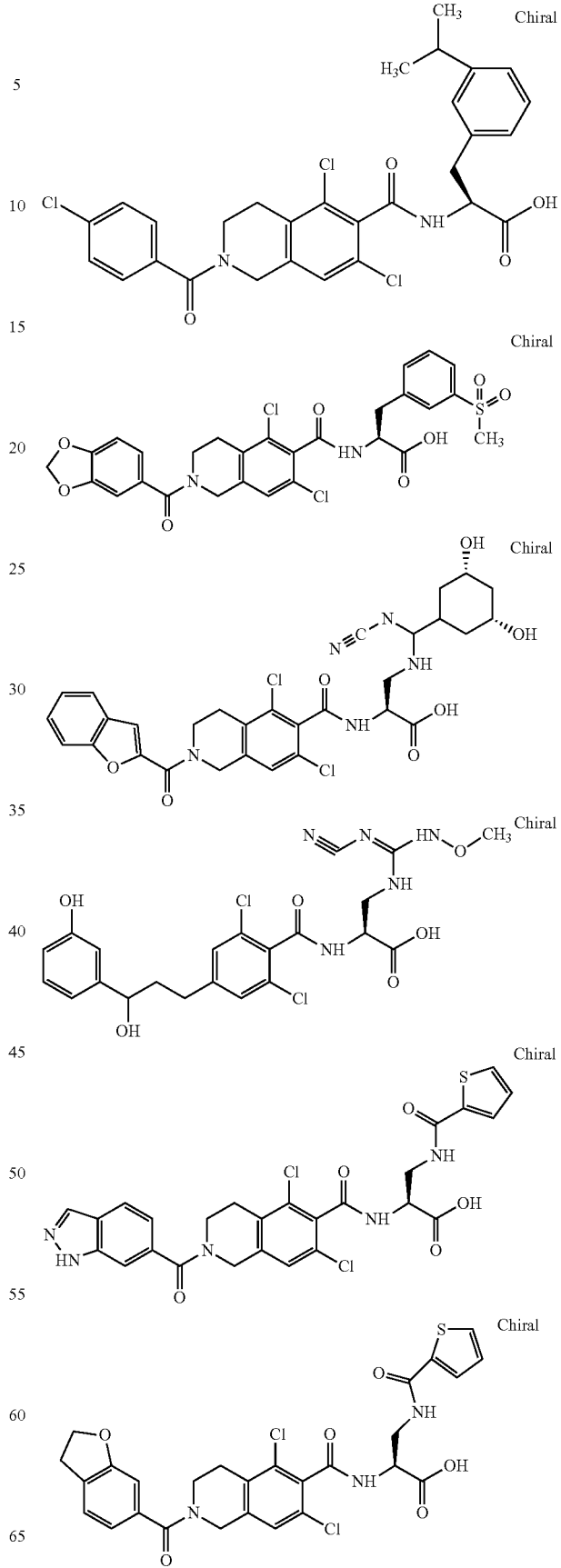

-continued
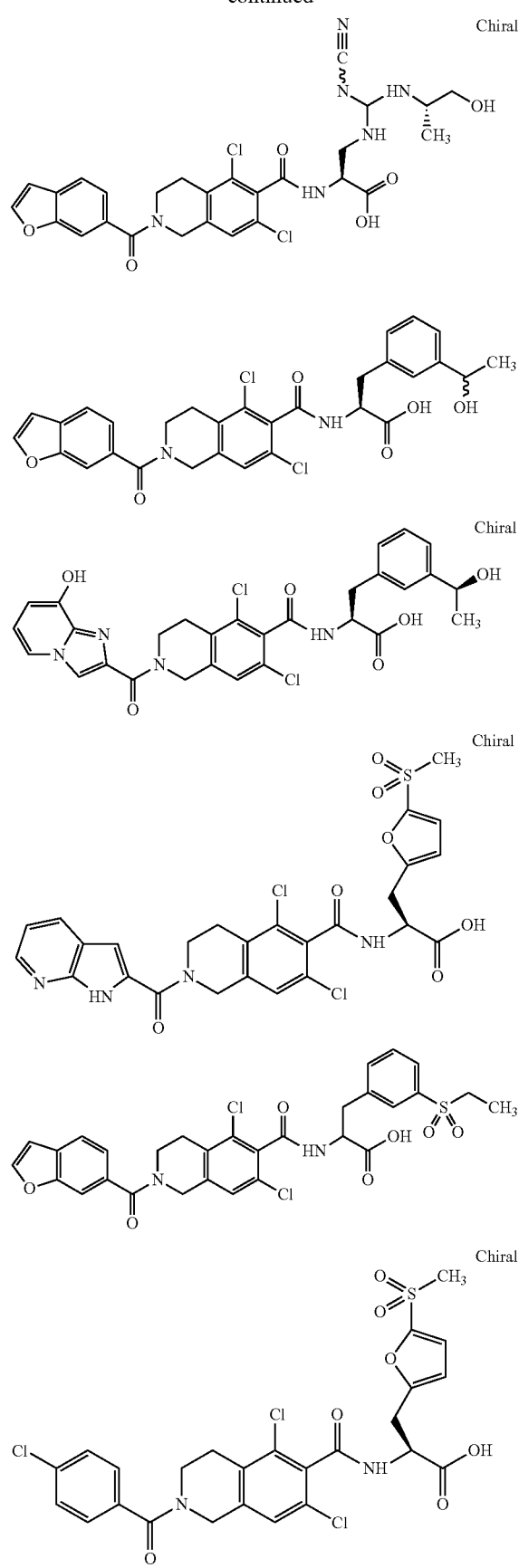
-continued
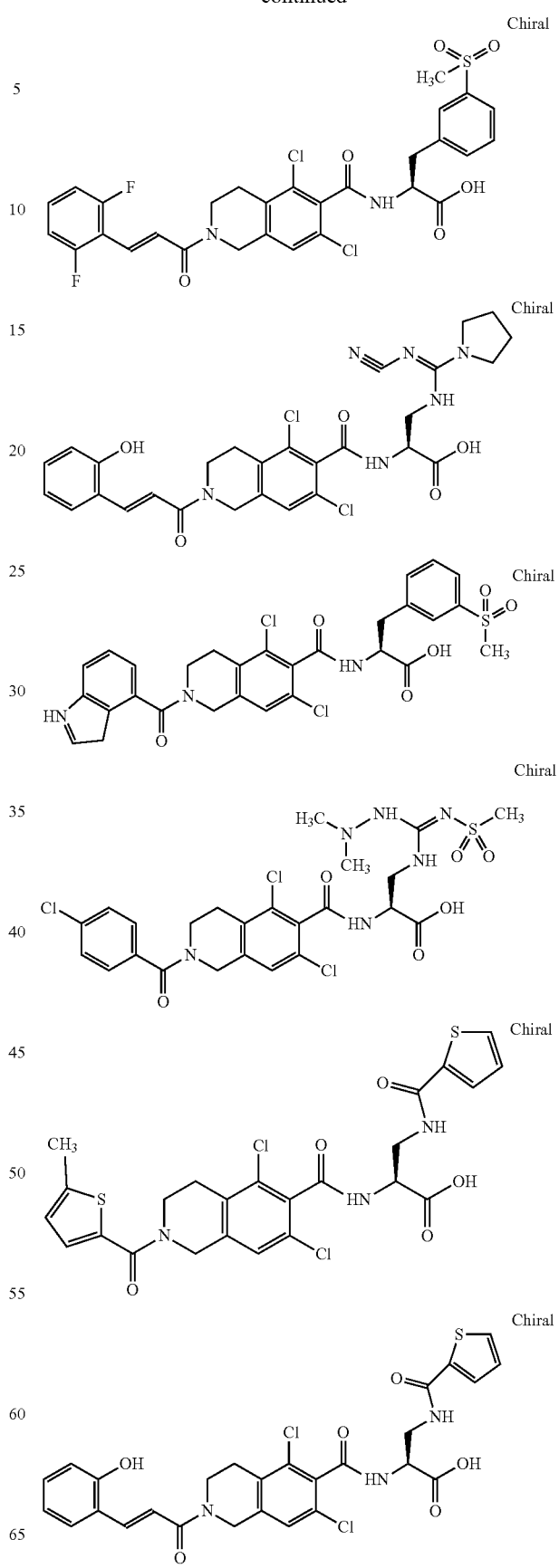

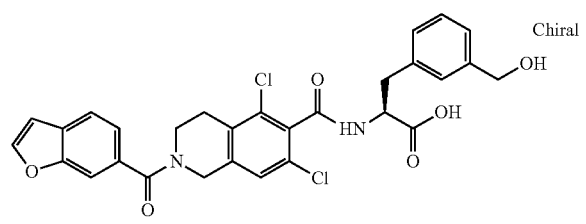
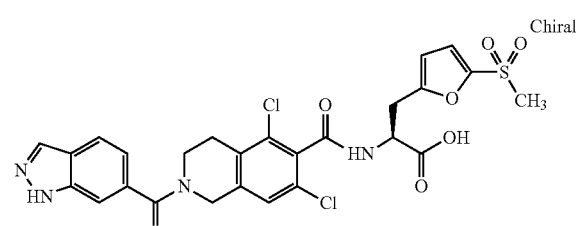
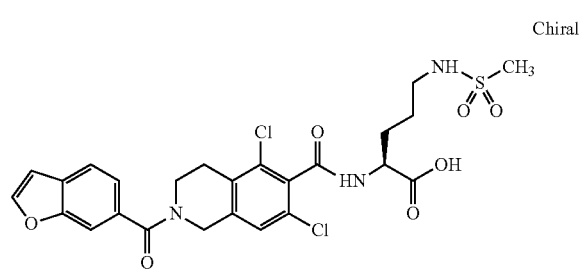
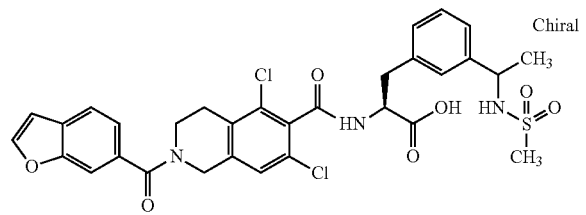
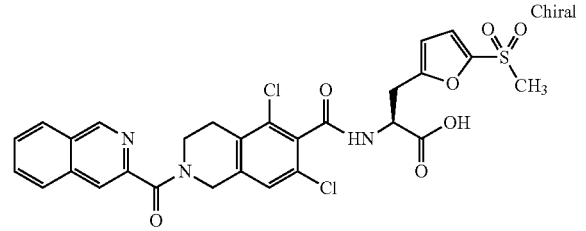
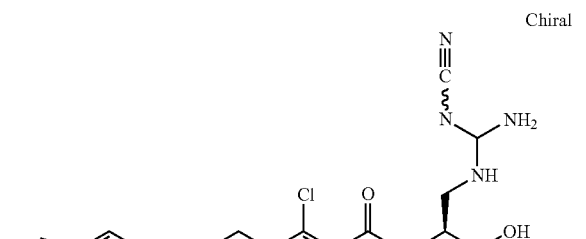
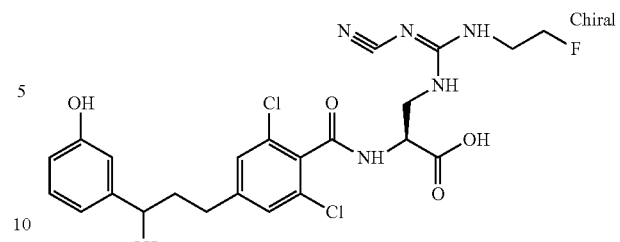
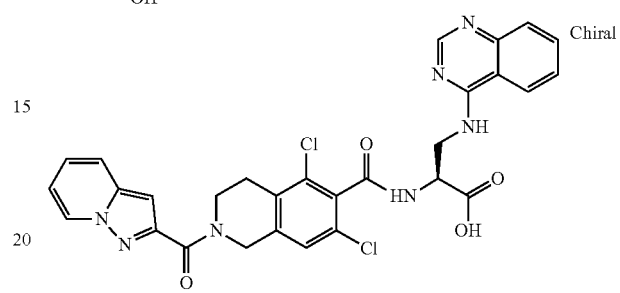
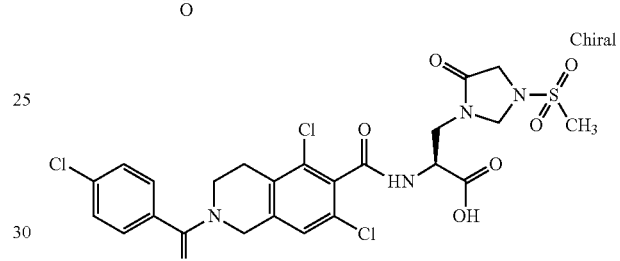
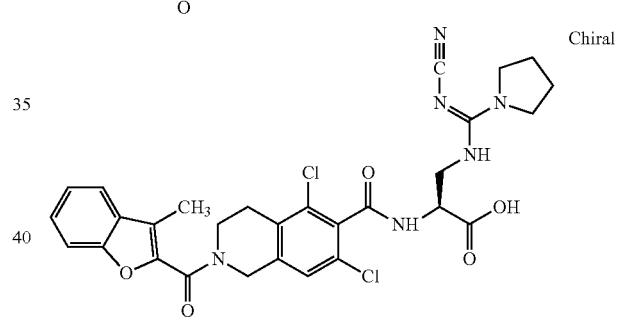
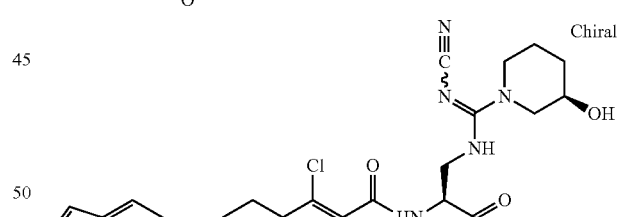
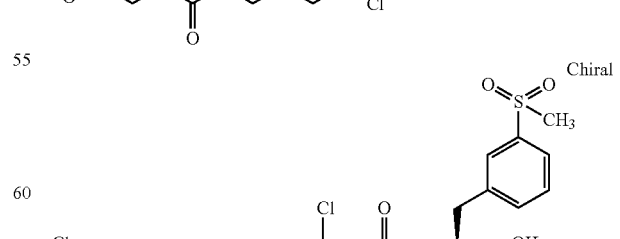

43

-continued

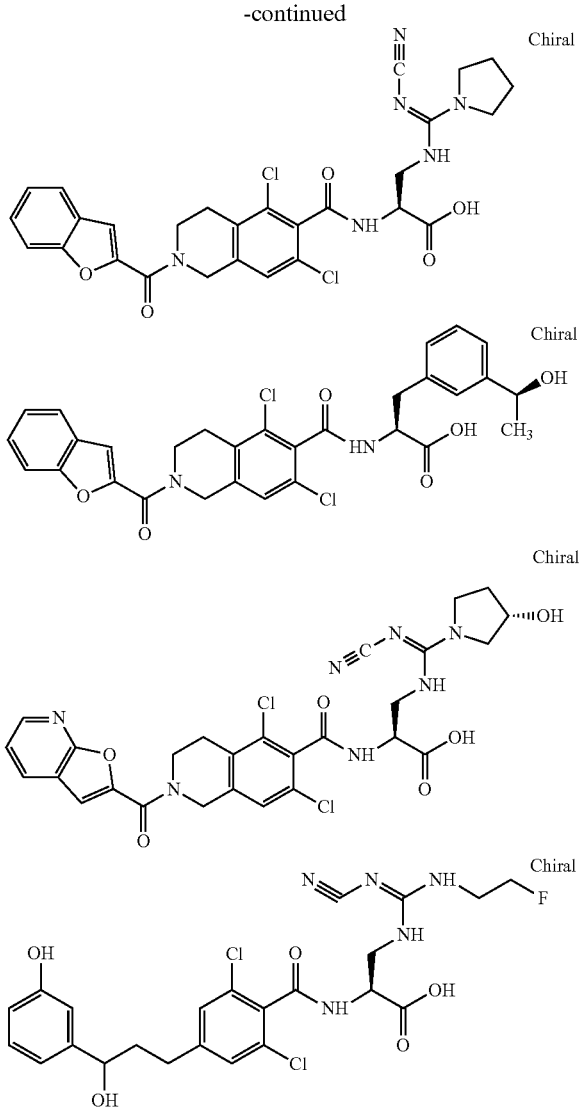

The compounds of the invention may be prepared by methods well known to those skilled in the art and may be purified in a number of ways, including by crystallization or precipitation under varied conditions to yield one or more polymorphs. Thus, the present invention encompasses the above described inventive compounds, their polymorphs, their pharmaceutically acceptable salts, their pharmaceutically acceptable solvates, and pharmaceutically acceptable compositions containing them.

The above examples of preferred embodiments are meant to illustrate some of the potential therapeutic agents, and are not meant to limit the invention in any way. The method of the invention can be practiced with antibodies, fragments of antibodies, peptides and other synthetic molecules that can be identified using the methods described above to identify a therapeutic agent that is a selective, potent and directly competitive inhibitor of the interaction between LFA-1 and ICAM-1, in order to treat dry eye disease.

Also provided herein are business methods which employ the compounds and diagnostic and therapeutic methods described herein. One business method involves the identification of LFA-1 antagonistic properties of peptides or small molecules and developing the compounds for treatment of LFA-1 mediated diseases, preferably by topical delivery. As the compounds are not administered systemically, the systemic pharmacokinetic profiles of these drugs are typically not determined and hence the candidate pool of drugs available for development is larger. In one embodiment, the LFA-1 antagonists are developed into ocular formulations and then promoted and sold for treatment of eye disorders, such as dry eye. The Hut78 assay is typically used to determine LFA-1 antagonistic properties. In addition to LFA-1 antagonistic properties, leukocyte antagonistic properties can be determined.

III. Administration

The method of the present invention may draw upon many suitable modes of administration to deliver the LFA-1 antagonist of the methods described herein. Such delivery to affected regions of the body may be achieved either via local or systemic administration. Suitable formulations and additional carriers are described in Remington "The Science and Practice of Pharmacy" (20$^{th}$ Ed., Lippincott Williams & Wilkins, Baltimore Md.), the teachings of which are incorporated by reference in their entirety herein.

In some embodiments, the invention provides a pharmaceutical composition for administration to a subject containing: (i) an effective amount of a therapeutic agent; and (ii) a pharmaceutical excipient suitable for oral administration. In some embodiments, the composition further contains: (iii) an effective amount of a second therapeutic agent.

In order to reduce inflammation in eye disorders, the pharmaceutical composition of the invention is preferably delivered to the ocular surface, interconnecting innervation, conjuncitva, lacrimal glands, or meibomian glands. It is envisioned that effective treatment can encompass administering therapeutic agents of the present invention via oral administration, topical administration, via injection, intranasally, rectally, transdermally, via an impregnated or coated device such as an ocular insert or implant, or iontophoretically, amongst other routes of administration.

For administration via injection, the pharmaceutical composition can be injected intramuscularly, intra-arterially, subcutaneously, or intravenously. A pump mechanism may be employed to administer the pharmaceutical composition over a preselected period. For some embodiments of the invention it is desirable to deliver drug locally, thus injections may be made periocularly, intraocularly, subconjunctively, retrobulbarly, or intercamerally. For some embodiments of the invention, systemic delivery is preferred.

For systemic administration, the compounds of the invention can be formulated for and administered orally. For administration that may result in either regional or systemic distribution of the therapeutic agents, the composition of the invention may be administered intranasally, transdermally, or via some forms of oral administration, e.g. with use of a mouthwash or lozenge incorporating a compound of the invention that is poorly absorbed from the G.I. For administration that may result in regional or local delivery of the composition of the invention, iontophoretic or topical administration may be used.

Additionally, the pharmaceutical compositions of the present invention may be administered to the ocular surface via a pump-catheter system, or released from within a continuous or selective release device such as, e.g., membranes such as, but not limited to, those employed in the Ocusert™ System (Alza Corp, Palo Alto, Calif.). The pharmaceutical compositions can be incorporated within, carried by or attached to contact lenses which are then worn by the subject. The pharmaceutical compositions can be sprayed onto ocular surface.

The pharmaceutical compositions of the invention may be administered in combination with other therapies for the treatment of the disorder or underlying disease. For example, the LFA-1 antagonist of the invention is administered at the same time, or separately during the treatment period for which a subject receives immunosuppressive therapies, such as azathioprine, cyclophosphoramide, methotrextate, antimalarial drugs, mycophenolan mofetile, daclizumab, intravenous immunoglobin therapy, and the like. In another example, the LFA-1 antagonist of the invention is administered at the same time or separately during the treatment period for which a subject receives other anti-inflammatory treatments, such as cyclosporin A, corticosteroids, NSAIDS, asprin, doxycycline, and the like. In a further example, the LFA-1 antagonist of the invention is administered at the same time or separately during the treatment period for which a subject receives hormone therapy, and the like. In yet a further example, the LFA-1 antagonist of the invention is administered at the same time or separately during the treatment period for which a subject receives anti-allergy therapy, palliative care for dry eye including artificial tears or artificial saliva, muscarinic M3 receptor agonists to increase aqueous secretions, autologous serum, sodium hyaluronate drops, and the like. These examples are illustrative only and are not meant to limit the invention. In some embodiments, the LFA-1 antagonist is administered in a single dose. A single dose of a LFA-1 antagonist may also be used when it is co-administered with another substance (e.g., an analgesic) for treatment of an acute condition. In some embodiments, the LFA-1 antagonist (by itself or in combination with other drugs) is administered in multiple doses. Dosing may be about once, twice, three times, four times, five times, six times, seven times, eight times, nine times, ten times or more than ten times per day. Dosing may be about once a month, once every two weeks, once a week, or once every other day. In one embodiment the drug is an analgesic. In another embodiment the LFA-1 antagonist and another therapeutic substance are administered together about once per day to about 10 times per day. In another embodiment the administration of the LFA-1 antagonist and another therapeutic substance continues for less than about 7 days. In yet another embodiment the co-administration continues for more than about 6, 10, 14, 28 days, two months, six months, or one year. In some cases, co-administered dosing is maintained as long as necessary, e.g., dosing for chronic inflammation. Administration of the compositions of the invention may continue as long as necessary. In some embodiments, a composition of the invention is administered for more than 1, 2, 3, 4, 5, 6, 7, 14, or 28 days. In some embodiments, a composition of the invention is administered for less than 28, 14, 7, 6, 5, 4, 3, 2, or 1 day. In some embodiments, a composition of the invention is administered chronically on an ongoing basis, e.g., for the treatment of chronic pain.

Dosing for the LFA-1 antagonist in the method of the invention may be found by routine experimentation. The daily dose can range from about $1\times10^{-7}$ g to 5000 mg. Daily dose range may depend on the form of LFA-1 antagonist e.g., the esters or salts used, and/or route of administration, as described herein. For example, for systemic administration, typical daily dose ranges are, e.g. about 1-5000 mg, or about 1-3000 mg, or about 1-2000 mg, or about 1-1000 mg, or about 1-500 mg, or about 1-100 mg, or about 10-5000 mg, or about 10-3000 mg, or about 10-2000 mg, or about 10-1000 mg, or about 10-500 mg, or about 10-200 mg, or about 10-100 mg, or about 20-2000 mg or about 20-1500 mg or about 20-1000 mg or about 20-500 mg, or about 20-100 mg, or about 50-5000 mg, or about 50-4000 mg, or about 50-3000 mg, or about 50-2000 mg, or about 50-1000 mg, or about 50-500 mg, or about 50-100 mg, about 100-5000 mg, or about 100-4000 mg, or about 100-3000 mg, or about 100-2000 mg, or about 100-1000 mg, or about 100-500 mg. In some embodiments, the daily dose of LFA-1 antagonist is about 100, 200, 300, 400, 500, 600, 700, 800, 900, or 1000 mg. In some embodiments, the daily dose of the LFA-1 antagonist is 10 mg. In some embodiments, the daily dose of the LFA-1 antagonist is 100 mg. In some embodiments, the daily dose of LFA-1 antagonist is 500 mg. In some embodiments, the daily dose of LFA-1 antagonist is 1000 mg.

For topical delivery to the ocular surface, the typical daily dose ranges are, e.g. about $1\times10^{-7}$ g to 5.0 g, or about $1\times10^{-7}$ g to 2.5 g, or about $1\times10^{-7}$ g to 1.00 g, or about $1\times10^{-7}$ g to 0.5 g, or about $1\times10^{-7}$ g to 0.25 g, or about $1\times10^{-7}$ g to 0.1 g, or about $1\times10^{-7}$ g to 0.05 g, or about $1\times10^{-7}$ g to 0.025 g, or about $1\times10^{-7}$ g to $1\times10^{-2}$ g, or about $1\times10^{-7}$ g to $5\times10^{-3}$ g, or about $1\times10^{-7}$ g to $2.5\times10^{-3}$ g, or about $1\times10^{-7}$ g to $1\times10^{-3}$ g, or about $1\times10^{-7}$ g to $5\times10^{4}$ g, or about $1\times10^{-6}$ g to 5.0 g, or about $1\times10^{-6}$ g to 2.5 g, or about $1\times10^{-6}$ g to 1 g, or about $1\times10^{-6}$ g to 0.5 g, or about $1\times10^{-6}$ g to 0.25 g, or about $1\times10^{-6}$ g to 0.1 g, or about $1\times10^{-6}$ g to $5\times10^{-2}$ g, or about $1\times10^{-6}$ g to $5\times10^{-2}$ g, or about $1\times10^{-6}$ g to $2.5\times10^{-2}$ g, or about $1\times10^{-6}$ g to $1\times10^{-2}$ g, or about $1\times10^{-6}$ g to $5\times10^{-3}$ g, or about $1\times10^{-6}$ g to $2.5\times10^{-3}$ g, or about $1\times10^{-6}$ g to $1\times10^{-3}$ g, or about $1\times10^{-6}$ g to $5\times10^{4}$ g, or about $1\times10^{-5}$ g to 5 g, or about $1\times10^{-5}$ g to 2.5 g, or about $1\times10^{-5}$ g to 1 g, or about $1\times10^{-5}$ g to 0.5 g, or about $1\times10^{-5}$ g to 0.25 g, or about $1\times10^{-5}$ g to 0.1 g, or about $1\times10^{-5}$ g to 0.05 g, or about $1\times10^{-5}$ g to $2.5\times10^{-2}$ g, or about $1\times10^{-5}$ g to $1\times10^{-2}$ g, or about $1\times10^{-5}$ g to $5\times10^{-3}$ g, or about $1\times10^{-5}$ g to $2.5\times10^{-3}$ g, or about $1\times10^{-5}$ g to $1\times10^{-3}$ g, or about $1\times10^{-5}$ g to $5\times10^{4}$ g. In some embodiments, the daily dose of LFA-1 antagonist is about $1\times10^{-7}$, $1\times10^{-6}$, $1\times10^{-5}$, $1\times10^{4}$, $1\times10^{-3}$ g, $1\times10^{-2}$ g, $1\times10^{1}$ g, or 1 g. In some embodiments, the daily dose of the LFA-1 antagonist is $1\times10^{-7}$ g. In some embodiments, the daily dose of the LFA-1 antagonist is $1\times10^{-5}$ g. In some embodiments, the daily dose of LFA-1 antagonist is $1\times10^{-3}$ g. In some embodiments, the daily dose of LFA-1 antagonist is $1\times10^{-2}$ g. In some embodiments the individual dose ranges from about $1\times10^{-7}$ g to 5.0 g, or about $1\times10^{-7}$ g to 2.5 g, or about $1\times10^{-7}$ g to 1.00 g, or about $1\times10^{-7}$ g to 0.5 g, or about $1\times10^{-7}$ g to 0.25 g, or about $1\times10^{-7}$ g to 0.1 g, or about $1\times10^{-7}$ g to 0.05 g, or about $1\times10^{-7}$ g to 0.025 g, or about $1\times10^{-7}$ g to $1\times10^{-2}$ g, or about $1\times10^{-7}$ g to $5\times10^{-3}$ g, or about $1\times10^{-7}$ g to $2.5\times10^{-3}$ g, or about $1\times10^{-7}$ g to $1\times10^{-3}$ g, or about $1\times10^{-7}$ g to $5\times10^{4}$ g, or about $1\times10^{-6}$ g to 5.0 g, or about $1\times10^{-6}$ g to 2.5 g, or about $1\times10^{-6}$ g to 1 g, or about $1\times10^{-6}$ g to 0.5 g, or about $1\times10^{-6}$ g to 0.25 g, or about $1\times10^{-6}$ g to 0.1 g, or about $1\times10^{-6}$ g to $5\times10^{-2}$ g, or about $1\times10^{-6}$ g to $5\times10^{-2}$ g, or about $1\times10^{-6}$ g to $2.5\times10^{-2}$ g, or about $1\times10^{-6}$ g to $1\times10^{-2}$ g, or about $1\times10^{-6}$ g to $5\times10^{-3}$ g, or about $1\times10^{-6}$ g to $2.5\times10^{-3}$ g, or about $1\times10^{-6}$ g to $1\times10^{-3}$ g, or about $1\times10^{-6}$ g to $5\times10^{4}$ g, or about $1\times10^{-5}$ g to 5 g, or about $1\times10^{-5}$ g to 2.5 g, or about $1\times10^{-5}$ g to 1 g, or about $1\times10^{-5}$ g to 0.5 g, or about $1\times10^{-5}$ g to 0.25 g, or about $1\times10^{-5}$ g to 0.1 g, or about $1\times10^{-5}$ g to 0.05 g, or about $1\times10^{-5}$ g to $2.5\times10^{-2}$ g, or about $1\times10^{-5}$ g to $1\times10^{-2}$ g, or about $1\times10^{-5}$ g to $5\times10^{-3}$ g, or about $1\times10^{-5}$ g to $2.5\times10^{-3}$ g, or about $1\times10^{-5}$ g to $1\times10^{-3}$ g, or about $1\times10^{-5}$ g to $5\times10^{4}$ g. In some embodiments, the individual doses as described above, is repeated 1, 2, 3, 4, 5, 6, 7, 8, 9, or 10 times per day.

For other forms of administration, the daily dosages may range about the range described for systemic administration or may range about the range described for topical administration.

IV. Formulations

The compounds of the invention may be formulated as a sterile solution or suspension, in suitable vehicles, well known in the art. Suitable formulations and additional carriers are described in Remington "The Science and Practice of Pharmacy" (20$^{th}$ Ed., Lippincott Williams & Wilkins, Baltimore Md.), the teachings of which are incorporated by reference in their entirety herein.

For injectable formulations, the vehicle may be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles.

The concentration of drug may be adjusted, the pH of the solution buffered and the isotonicity adjusted to be compatible with intravenous injection, as is well known in the art.

Oral formulations can be tablets, capsules, troches, pills, wafers, chewing gums, lozenges, aqueous solutions or suspensions, oily suspensions, syrups, elixirs, or dispersible powders or granules, and the like and may be made in any way known in the art. Oral formulations may also contain sweetening, flavoring, coloring and preservative agents. Pharmaceutically acceptable excipients for tablet forms may comprise nontoxic ingredients such as inert diluents, such as calcium carbonate, sodium carbonate, lactose, calcium phosphate, or sodium phosphate, and the like.

In the case of tablets for oral use, carriers which are commonly used include lactose and corn starch, and lubricating agents such as magnesium stearate are commonly added. For oral administration in capsule form, useful carriers include lactose and corn starch. Further nonlimiting examples of carriers and excipients include milk, sugar, certain types of clay, gelatin, stearic acid or salts thereof, calcium stearate, talc, vegetable fats or oils, gums and glycols.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, preferred ionic surfactants include, by way of example: lecithins, lysolecithin, phospholipids, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

Surfactants may be used in any formulation of the invention where its use is not otherwise contradicted. In some embodiments of the invention, the use of no surfactants or limited classes of surfactants are preferred.

When formulating compounds of the invention for oral administration, it may be desirable to utilize gastroretentive formulations to enhance absorption from the gastrointestinal (GI) tract. A formulation which is retained in the stomach for several hours may release compounds of the invention slowly and provide a sustained release that may be preferred in some embodiments of the invention. Disclosure of such gastroretentive formulations are found in Klausner, E. A.; Lavy, E.; Barta, M.; Cserepes, E.; Friedman, M.; Hoffman, A. 2003 "Novel gastroretentive dosage forms: evaluation of gastroretentivity and its effect on levodopa in humans." Pharm. Res. 20, 1466-73, Hoffman, A.; Stepensky, D.; Lavy, E.; Eyal, S. Klausner, E.; Friedman, M. 2004 "Pharmacokinetic and pharmacodynamic aspects of gastroretentive dosage forms" Int. J. Pharm. 11, 141-53, Streubel, A.; Siepmann, J.; Bodmeier, R.; 2006 "Gastroretentive drug delivery systems" Expert Opin. Drug Deliver. 3, 217-3, and Chavanpatil, M. D.; Jain, P.; Chaudhari, S.; Shear, R.; Vavia, P. R. "Novel sustained release, swellable and bioadhesive gastroretentive drug delivery system for olfoxacin" Int. J. Pharm. 2006 epub March 24. Expandable, floating and bioadhesive techniques may be utilized to maximize absorption of the compounds of the invention.

Intranasal administration may utilize an aerosol suspension of respirable particles comprised of the compounds of the invention, which the subject inhales. The compound of the invention are absorbed into the bloodstream via pulmonary absorption or contact the lacrimal tissues via nasolacrimal ducts, and subsequently be delivered to the lacrimal tissues in a pharmaceutically effective amount. The respirable particles may be solid or liquid, with suitably sized particles, as is known in the art to be effective for absorption. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

For transdermal administration, any suitable formulation known in the art may be utilized, either as a solution, suspension, gel, powder, cream, oil, solids, dimethylsulfoxide (DMSO)-based solutions or liposomal formulation for use in a patch or other delivery system known in the art. The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For topical administration, all the formulations for topical ocular administration used in the field of ophthalmology (e.g., eye drops, inserts, eye packs, impregnated contact lenses, pump delivery systems, dimethylsulfoxide (DMSO)-based solutions suspensions, liposomes, and eye ointment) and all the formulations for external use in the fields of dermatology and otolaryngology (e.g., ointment, cream, gel, powder, salve, lotion, crystalline forms, foam, and spray) may be utilized as is known in the art. Additionally all suitable formulations for topical administration to skin and mucus membranes of the nasal passages may be utilized to deliver the compounds of the invention. The pharmaceutical compositions of the present invention may be a liposomal formulation for topical or oral administration, any of which are known in the art to be suitable for the purpose of this invention.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

It is envisioned additionally, that the compounds of the invention may be attached releasably to biocompatible polymers for use in sustained release formulations on, in or attached to inserts for topical or systemic administration. The controlled release from a biocompatible polymer may be utilized with a water soluble polymer to form a instillable formulation, as well.

Eye drops may be prepared by dissolving the active ingredient in a sterile aqueous solution such as physiological saline, buffering solution, etc., or by combining powder compositions to be dissolved before use. Other vehicles may be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The solubility of the components of the present compositions may be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Such co-solvents may be employed at a level of from about 0.01% to 2% by weight.

The composition of the invention can be formulated as a sterile unit dose type containing no preservatives. The compositions of the invention may be packaged in multidose form. Preservatives may be preferred to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, such preservatives may be employed at a level of from 0.004% to 0.02%. In the compositions of the present application the preservative, preferably benzalkonium chloride, may be employed at a level of from 0.001% to less than 0.01%, e.g. from 0.001% to 0.008%, preferably about 0.005% by weight. It has been found that a concentration of benzalkonium chloride of 0.005% may be sufficient to preserve the compositions of the present invention from microbial attack.

The amount of administration and the number of administrations of the active ingredient used in the present invention vary according to sex, age and body weight of patient, symptoms to be treated, desirable therapeutic effects, administration routes and period of treatment. For eye drops for an adult, the formulations containing the compounds of the invention may range in concentration from about 0.0001 to 10.0 W/V %, about 0.005 to 10.0 W/V %, about 0.01 to 10.0 W/V %, about 0.05 to 10.0 W/V %, about 0.1 to 10.0 W/V %, about 0.5 to 10.0 W/V %, about 1.0 to 10.0 W/V %, about 20 to 10.0 W/V %, about 3.0 to 10.0 W/V %, about 4.0 to 10.0 W/V %, or about 5.0 to 10.0 W/V %. One embodiment of the invention has a formulation of about 1.0 to 10.0 W/V % of the compounds of the invention. One embodiment of the invention has a formulation of about 0.01 to 10.0 W/V % of the compounds of the invention. One embodiment of the invention has a formulation of about 5.0 to 10.0 W/V % of the compounds of the invention. The administration may be administered several times a day per eye, preferably one to ten times, more preferably one to four times, most preferably once a day. The size of the drop administered may be in the range of about 10-100 µl, about 10-90 µl, about 10-80 µl, about 10-70 µl, about 10-60 µl, about 10-50 µl, about 10-40 µl, about 10-30 µl, about 20-100 µl, about 20-90 µl, about 20-80 µl, about 20-70 µl, about 20-60 µl, about 20-50 µl, about 20-40 µl, or about 20-30 µl. One embodiment of the invention administers a drop in the range of 10-30 µl. One embodiment of the invention administers a drop in the range of 10-100 µl. One embodiment of the invention administers a drop in the range of 20-50 µl. One embodiment of the invention administers a drop in the range of 10-60 µl.

The formulations of the invention may be administered several drops per time, one to four drops, preferably one to three drops, more preferably one to two drops, and most preferably one drop per day.

In formulations for ointment, cream, lotion or spray, the concentration of the compounds of the invention in the formulations may range about 0.0001 10.0 W/V %, about 0.005 to 10.0 W/V %, about 0.01 to 10.0 W/V %, about 0.05 to 10.0 W/V %, about 0.1 to 10.0 W/V %, about 0.5 to 10.0 W/V %, about 1.0 to 10.0 W/V %, about 20 to 10.0 W/V %, about 3.0 to 10.0 W/V %, about 4.0 to 10.0 W/V %, or about 5.0 to 10.0 W/V %. One embodiment of the invention has a formulation of about 1.0 to 10.0 W/V % of the compounds of the invention. One embodiment of the invention has a formulation of about 0.01 to 10.0 W/V % of the compounds of the invention. One embodiment of the invention has a formulation of about 5.0 to 10.0 W/V % of the compounds of the invention. These formulations may be applied or sprayed several times a day, preferably one to six times, more preferably one to four times, and most preferably once a day. The compounding ratio of each ingredient may be suitably increased or decreased based on the degree of inflammations or infections.

The formulations of the invention can further include other pharmacological active ingredients as far as they do not contradict the purpose of the present invention. In a combination of plural active ingredients, their respective contents may be suitably increased or decreased in consideration of their effects and safety.

V. Kits

The invention also provides kits. The kits include a compound of the invention in suitable packaging, and written material that can include instructions for use, discussion of clinical studies, listing of side effects, and the like. The kit may further contain another therapeutic agent that is co-administered with the LFA-1 antagonist of the invention. In some embodiments, the therapeutic agent and the LFA-1 antagonist of the invention are provided as separate compositions in separate containers within the kit. In some embodiments, the therapeutic agent and the LFA-1 antagonist of the invention are provided as a single composition within a container in the kit. Suitable packaging and additional articles for use (e.g., measuring cup for liquid preparations, foil wrapping to minimize exposure to air, dispensers, and the like) are known in the art and may be included in the kit.

VI. Method to Identify New Compounds Useful in the Method of Treatment

A. Background of the Assay Method

1. Dependence of Ligand Affinities on Divalent Cations

Figure 4:
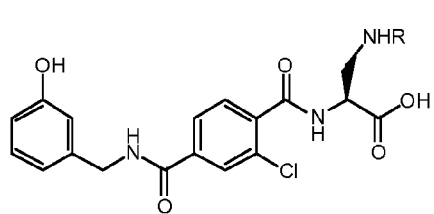
FIG. 4 depicts small molecule antagonists useful in the methods of identification.
Figure 4:
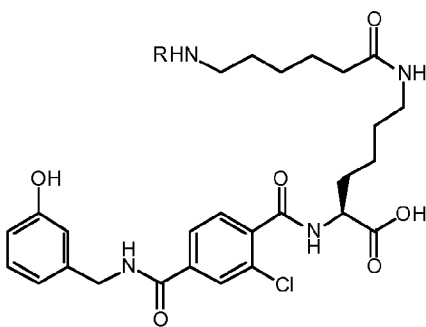
Figure 4:
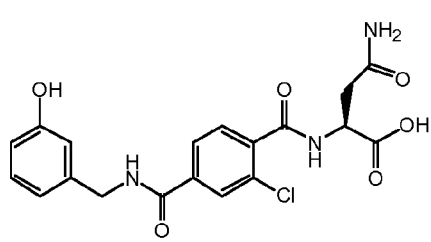
Figure 4:
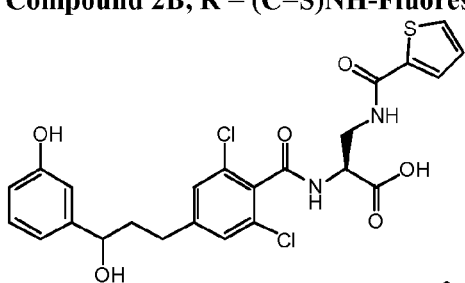
Figure 4:
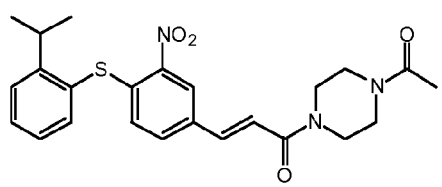
Figure 4:
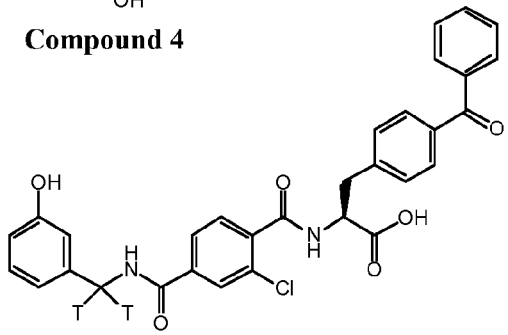

Divalent cations play a critical role in integrin/ligand binding and their presence is essential in experimental investigations of these interactions. See Hynes, R. O. 1992. Integrins: Versatility, modulation, and signaling in cell adhesion, *Cell*, 69: 11-25; Humphries, M. J. 1996. Integrin activation: the link between ligand binding and signal transduction, *Curr. Op. Cell Biol.*, 8: 632-640. The affinities of ICAM-1-Ig and compounds 1, 3, and 4 (structures shown in FIG. 4) for LFA-1 under two sets of commonly used divalent cation conditions were measured using fluorescence polarization. The affinity of compound 1 for LFA-1 was first measured in a direct binding assay, and then the affinities of ICAM-1-Ig and compounds 3 and 4 for LFA-1 were measured in competition with compound 1 for LFA-1 (FIG. 4, and Table 1 in FIG. 5). The affinity of the A-286982, which binds to the IDAS, was not measured as it does not compete with compound 1 for binding to LFA-1 (see below). Similar changes in the affinities of compounds 1, 3 and 4 for LFA-1 were measured under the different cation conditions as for ICAM-1-Ig. The small molecule affinities increase at least ten-fold in the presence of $MnCl_2$ over those measured in $CaCl_2$ and $MgCl_2$. These small molecules do not bind to LFA-1 in the absence of divalent cations (data not shown). Similarly, the binding affinities of the soluble protein, ICAM-1-Ig, for LFA-1 in solution, as measured by the same method, in the presence of $MnCl_2$, is at least four-fold better than the affinity in the presence of $CaCl_2$ and $MgCl_2$. Thus, unlike the classes of LFA-1 antagonists including A-286982 that are known to bind to the IDAS region of the I domain (Liu, G., Huth, J. R., Olejniczak, E. T., Mendoza, R., DeVries, P., Leitza, S., Reilly, E. B., Okasinski, G. F., Fesik, S. W., and von Geldern, T. W. 2001. Novel p-arylthio cinnamides as antagonists of leukocyte function-associated antigen-1/intracellular adhesion molecule-1 interaction. 2. Mechanism of inhibition and structure-based improvement of pharmaceutical properties, J. Med. Chem., 44: 1202-1210., Huth, J. R., Olejniczak, E. T., Mendoza, R., Liang, H., Harris, E. A. S., Lupher, M. L. Jr., Wilson, A. E., Fesik, S. W., and Staunton, D. E. 2000. NMR and mutagenesis evidence for an I domain allosteric site that regulates lymphocyte function-associated antigen 1 ligand binding, *Proc. Natl. Acad. Sci. U.S.A.*, 97: 5231-5236.) and are reported to bind to LFA-1 in a cation-independent manner (Welzenbach, K., Hommel, U., and Weitz-Schmidt, G. 2002. Small molecule inhibitors induce conformational changes in the I domain and the I-like domain of Lymphocyte Function-Associated Antigen-1, J. Biol. Chem., 277: 10590-10598), both ICAM-1-Ig and the class of LFA-1 antagonists represented by compounds 1-4 share a divalent cation sensitivity for LFA-1 binding (Table 1). Consequently, in order to identify antagonists of LFA-1/ICAM-1 which bind in a similar manner to that of ICAM-1-Ig and compounds 1-4, all binding assays reported herein were performed under similar conditions, in the presence of $MnCl_2$, which is known to maximize the binding of both ICAM-1 and these cation-sensitive antagonists.

2. Crosslinking of Compound 5 to the αL Subunit of LFA-1

Figure 6:
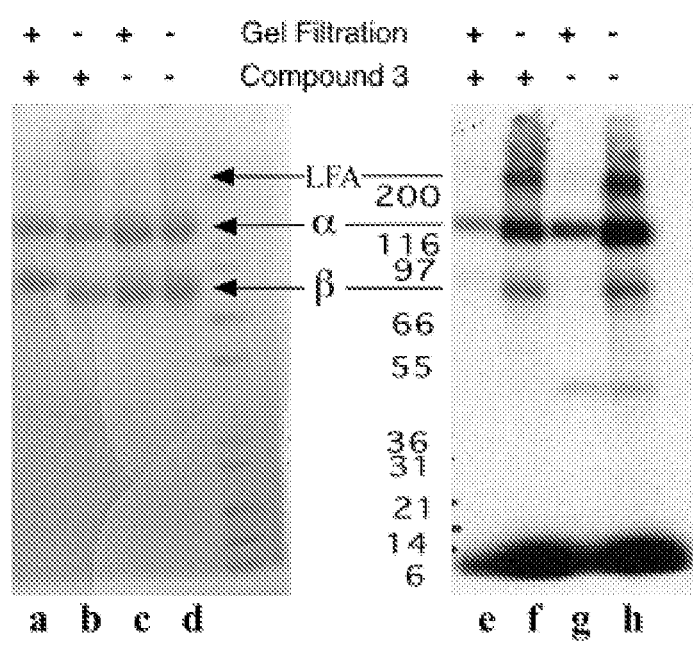
FIG. 6 depicts SDS-PAGE analysis of compound 5 crosslinked LFA-1.

To identify the binding site of small molecule antagonists, compound 5, a tritium-labeled, photoactivatable analogue of compound 3 was bound to LFA-1 and then photocrosslinked. To maximize specific, high affinity crosslinking, it was necessary to gel filter the samples to remove unbound or weakly bound compound 5 prior to irradiation (FIG. 6, lanes e vs. f and g vs. h). In the absence of gel filtration, there was significant crosslinking of compound 5 to LFA-1 α subunit, β subunit, and heterodimer (the band at approximately 200,000), whereas nonspecific crosslinking was not observed in the gel filtered samples (data not shown). Under gel filtration conditions, compound 5 specifically crosslinked only to the αL subunit (FIG. 6, lanes c and g). Moreover, the presence of compound 3 during the incubation substantially reduced the incorporation of tritium into the αL subunit (FIG. 6, lane e vs. g). Similarly, in the presence of compound 3, there was a slight reduction of tritium incorporation into the αL subunit, β2 subunit and heterodimer in the absence of gel filtration (FIG. 6, lane f vs. h). No crosslinking of compound 5 occurred when gel filtered samples of the isolated, structurally intact αL or β2 subunits were used (data not shown). Thus, the high affinity binding site necessary to crosslink after gel filtration is provided by the intact LFA-1 heterodimer. The absence of a high affinity site in the isolated αL subunit is consistent with a previous study demonstrating lack of interaction of XVA143 with the isolated I domain (Welzenbach et al. 2002).

The site of crosslinking was further defined by fragmenting the affinity-labeled αL subunit with hydroxylamine, electrophoretically separating the fragments, and then performing N-terminal sequencing on the radiolabeled fragments to determine their locations within the protein sequence. Two sequences were identified, the first starting with residue 1 (sequence found: YNLDVRGARSFS) and the second with residue 30 (sequence found: GVIVGAPGEGNST) (Larson, R. S., Corbi, A. L., Berman, L., and Springer, T. 1989. Primary structure of the leukocyte function-associated molecule-1 alpha subunit: an integrin with an embedded domain defining a protein superfamily, J. Cell Biol., 108: 703-712). Both peptides were approximately 500 amino acids long as judged by their sizes on SDS-PAGE (50-60 kDa); this fragment size is consistent with the next two predicted cleavage sites (N-G) for hydroxylamine, N507 and N530 (Larson et al. 1989, Bornstein, P. 1969. The nature of a hydroxylamine-sensitive bond in collagen, Biochem. Biophys. Res. Comm., 36: 957-964). No label was incorporated into the C-terminal half of the subunit. Attempts to refine the crosslinking site further were not successful. No definable labeled peptides were recoverable after limited digestion of the labeled αL subunit with either cyanogen bromide or Lys-C.

3. Lack of Binding of Compound 2B to LFA-1 Lacking the I Domain

Figure 7:
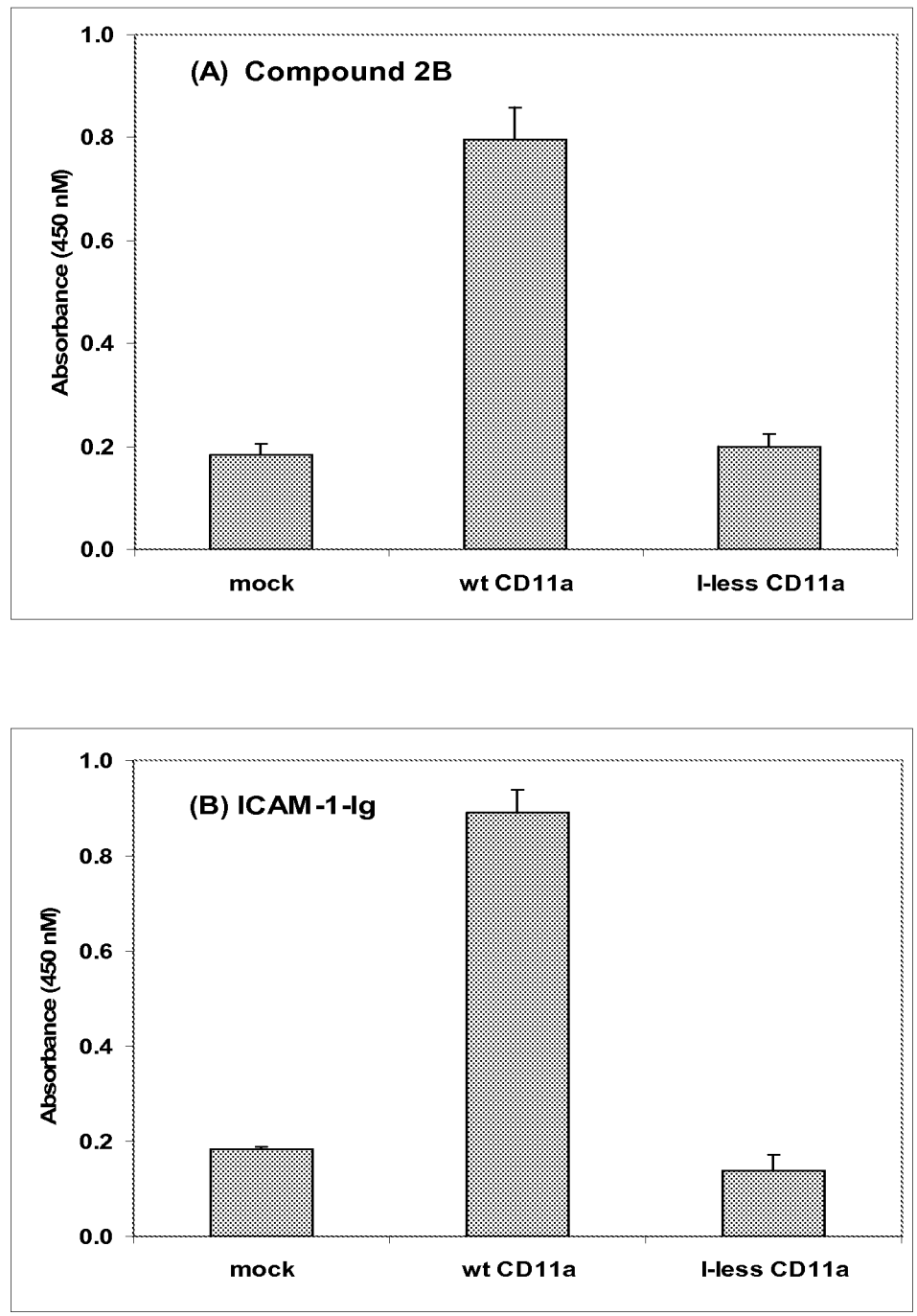
FIG. 7 depicts binding of compound 2B and ICAM-1-Ig to 293 cells expressing wild type LFA-1 or LFA-1 lacking the I domain.

The role of the I domain in the binding of compound 2B and related analogs to LFA-1 was demonstrated by preparing a construct of the αL subunit lacking the I domain. The β2 construct alone (mock) or together with the construct lacking the I domain or wild type αL was transfected into 293 cells, and the binding of compound 2B to the transfected cells was examined (FIG. 7). Compound 2B showed substantial binding to the wild type αL transfected cells but demonstrated no significant binding to the cells transfected with αL lacking the I domain relative to binding to mock (β2) transfected cells. Transfectants were also tested for their ability to adhere to ICAM-1-Ig, and as expected, the LFA-1 transfected cells lacking the I domain and mock transfectants showed indistinguishable background levels of binding, while the wild type αL transfected cells showed robust adhesion (FIG. 7B) (Yalamanchili, P., Lu, C., Oxvig, C., and Springer T. A. 2000. Folding and function of I domain-deleted Mac-1 and lymphocyte function-associated antigen-1, *J. Biol. Chem.*, 275: 21877-21882). Evaluation of the binding of a panel of LFA-1 antibodies to the transfected cells indicated that, apart from loss of binding by antibodies that mapped to the I domain, the LFA-1 heterodimer appeared to be intact in the transfected cells lacking the αL I domain (data not shown).

The data support the conclusion that compound 3 and related molecules bind to a high affinity site on LFA-1 that overlaps with the ICAM-1 binding site which has previously been shown to include the MIDAS motif of the I domain in the αL subunit of LFA-1 (Shimaoka, M., Xiao, T., Liu, J.-H., Yang, Y., Dong, Y., Jun, C-D., McCormack, A. Zhang, R., Joachimiak, A., Takagi, J., Wang, J.-H., and Springer, T. A. 2003a. Structures of the alpha L I domain and its complex with ICAM-1 reveal a shape-shifting pathway for integrin regulation, *Cell*, 112: 99-111.).

Corroborating evidence for the close proximity of the ICAM-1 and small molecule antagonist binding sites on LFA-1 can be seen in the common effect of the deletion of the I domain on the binding of both ICAM-1-Ig and compound 2B. Both compound 2B and ICAM-1 were unable to bind to LFA-1 lacking the I domain, the domain in which the ICAM-1 binding site is located. Moreover, the ability of A-286982 to allosterically modify the binding of both ICAM-1-Ig and compound 2B is consistent with a close proximity of their binding sites to the A-286982 binding site in the IDAS motif in the I domain of the LFA-1 α subunit (Liu, G. 2001b. Small molecule antagonists of the LFA-1/ICAM-1 interaction as potential therapeutic agents, *Expert Opin. Ther. Patents*, 11: 1383-1393, Liu et al. 2001). The selective photochemical crosslinking of compound 5 to the α chain of LFA-1 localizes its binding site to within residues 30-507 of this subunit. All of the findings noted above are consistent with a single high affinity small molecule binding site located in the I domain of the α chain of LFA-1.

Close examination of the photochemical crosslinking study performed with a relatively high concentration of compound 5 (4.1 µM, FIG. 6) affords direct evidence for an additional low affinity small molecule binding site on LFA-1. Dramatically different protein and crosslinking patterns are observed in the presence and absence of gel filtration. When samples are gel filtered to remove unbound and weakly bound molecules prior to irradiation, only high affinity labeling of the α subunit is observed. However, in the absence of the gel filtration step, irradiation of the complex of compound 5 with LFA-1 results in high intensity crosslinking to the α subunit and lower intensity crosslinking to a low affinity binding site in the β subunit whose complex with compound 5 is too weak to survive gel filtration. Under both conditions, the observed crosslinking is partially inhibited by a large excess (290 µM) of compound 3 (FIG. 6, lanes e and g, f and h), demonstrating the specific nature of the binding to both sites. Attempts to crosslink compound 5 to either of the isolated α or β subunits failed to afford high affinity complexes capable of surviving the gel filtration process. Consequently, it appears that the high affinity competitive binding of the class of compounds represented by compound 3 requires the presence of an intact full length LFA-1 heterodimer. Attempts to capture this binding site in constructs of either of the LFA-1 subunits or the isolated I domain results in diminished affinity of LFA-1 for ICAM-1 and small molecule analogs of compound 3 (e.g. XVA143) (Shimaoka, M., Lu, C., Palframan, R. T., von Andrian, U. H., McCormack, A., Takagi, J., and Springer, T. A. 2001. Reversibly locking a protein fold in an active conformation with a disulfide bond: integrin alphaL I domains with high affinity and antagonist activity in vivo, *Proc. Natl. Acad. Sci, U.S.A.*, 98: 6009-6014., Welzenbach et al. 2002). It is particularly interesting to note the presence of a minor LFA-1 heterodimer band that appears in the absence of gel filtration (FIG. 6, band at >200,000 daltons.) The intensity of the LFA-1 band as judged by both Coomassie blue staining and autoradiography is consistent with low affinity binding to a second site on the β chain that stabilizes the heterodimer.

It appears, from published gel stabilization studies (Shimaoka, M., Salas, A., Yang, W., Weitz-Schmidt, G. and Springer, T. 2003b. Small molecule integrin antagonists that bind to the β$_2$ subunit I-like domain and activate signals in one direction and block them in another, *Immunity*, 19: 391-402, Salas, A., Shimaoka, M., Kogan, A. N., Harwood, C., von Andrian, U. H., and Springer, T. A., 2004. Rolling adhesion through an extended conformation of integrin α$_L$β$_2$ and relation to α I and β I-like domain interaction, Immunity, 20: 393-406, Yang, W., Shimaoka, M., Salas, A., Takagi, J., and Springer, T. A. 2004. Intersubunit signal transmission in integrins by a receptor-like interaction with a pull spring. *PNAS*, 101: 2906-2911), that the binding site responsible for the stabilization of LFA-1 to SDS-PAGE resides in the I-like domain of the β subunit. The data presented herein shows that this β subunit binding site is not related to the high affinity binding site in the α subunit which is responsible for the direct competitive inhibition of ICAM-1 binding. However, the β subunit binding site responsible for LFA-1 stabilization by compound 3 may be the same as the low affinity β subunit crosslinking site we have observed.

Overall, the crosslinking and binding experiment results presented herein indicate that there are two distinct binding sites for the class of LFA-1 small molecule antagonist probes used herein. The first is a high affinity binding site in the αL subunit of LFA-1 through which the small molecule and LFA-1 form a complex which is stable enough (e.g. $K_d$<25 nM) to survive the gel filtration process. It is this small molecule binding site that has been characterized in the binding experiments reported here as overlapping the ICAM-1 binding site and that correlates with: the potent inhibition of LFA-1/ICAM-1 binding by compounds 3 and 4 (compound 4 $IC_{50}$=1.4 nM); their potent inhibition of LFA-1 induced lymphocyte proliferation (compound 4 $IC_{50}$=3 nM) in vitro; and their inhibition of the immune system's response in vivo (Gadek et al. 2002). The second site is a lower affinity binding site (e.g. $K_d$>1 µM) in the β subunit which is involved with stabilization of the LFA-1 heterodimer under SDS-PAGE. This site is more dynamic by nature (i.e. faster off rate) and does not survive the gel filtration/photolysis process. The characteristics of this second low affinity site are consistent with those of the recently described α/β I-like allosteric antagonist binding site in the I-like domain of the β subunit (Welzenbach et al. 2002, Shimaoka et al. 2003b, Salas et al. 2004, Yang et al. 2004). The low affinity binding of the ICAM-1 mimetics described herein to the β subunit of LFA-1, presumably to the I-like domain, is likely due to the sequence homology between the I and I-like domains, particularly with regard to similarities in MIDAS motifs and their affinities for the carboxylic acid moiety common to this class of antagonists. Given that the β2 family of integrins, including MAC-1, share this subunit, the affinity of compounds for the I-like domain in the β2 subunit must be attenuated in order to select antagonists which are specific to LFA-1 (Keating, S., Marsters, J., Beresini, M., Ladner, C., Zioncheck, K., Clark, K., Arellano, F., and Bodary, S. 2000. Putting the pieces together: Contribution of fluorescence polarization assays to small molecule lead optimization, *SPIE Proceedings,* 3913: 128-137).

The experiments described above substantiate the high affinity binding of compounds 3 and 4 to LFA-1 in a manner that is similar to that of ICAM-1, at a site overlapping the ICAM-1 binding site involving the MIDAS motif within the I domain of the LFA-1 α subunit (Shimaoka, M., Xiao, T., Liu, J.-H., Yang, Y., Dong, Y., Jun, C-D., McCormack, A. Zhang, R., Joachimiak, A., Takagi, J., Wang, J.-H., and Springer, T. A. 2003a. Structures of the alpha L I domain and its complex with ICAM-1 reveal a shape-shifting pathway for integrin regulation, *Cell,* 112: 99-111.). This is consistent with their proposed mimicry of the ICAM-1 epitope (Gadek et al. 2002), and inconsistent with any conclusion that they function as α/β I-like allosteric antagonists of LFA-1/ICAM-1 (Shimaoka et al. 2003b, Shimaoka, M., and Springer, T. A. 2004. Therapeutic antagonists and the conformational regulation of the β2 integrins, *Curr. Topics Med. Chem.,* 4: 1485-1495). The binding of these ICAM-1 mimetics to the β2 integrin subunit, albeit with lower affinity, raises the question of whether ICAM-1 itself binds to a second site in the I-like domain (Welzenbach et al. 2002, Shimaoka et al. 2003b, Salas et al. 2004, Yang et al. 2004, Shimaoka and Springer 2004) as part of a feedback mechanism. The requirements for divalent cations, to ensure the formation of the active conformation of LFA-1, and physical corroboration that probe molecules 1-5, known modulators of LFA-1, compete directly with ICAM-1, are experimental details used in the present invention to form a method of identifying new antagonists which are direct competitive antagonists of LFA-1. The method is useful to identify new antagonists of LFA-1, to be used in the method of the invention to treat dry eye disease.

It has been shown, supra, that small molecules can bind with high affinity to the α-L subunit, which is unique to LFA-1. Consequently these compounds can be selective for LFA-1 (αLβ2) over Mac-1 (αMβ2). One preferred embodiment of the invention is to identify and utilize selective inhibitors of LFA-1, which may confer advantages in therapeutic safety.

B. Assay Methodology

Competitive Binding Experiments

1. Antagonist Competition in the LFA-1/ICAM-1 and LFA-1/Small Molecule ELISA

Compounds 2A and 3, A-286982, and sICAM-1 were used to demonstrate the method. In order to illustrate inhibition of binding of ICAM-1-Ig to LFA-1, these antagonists were titrated into the LFA-1/ICAM-1 ELISA. The experiment was performed by the addition of ⅕ serial dilutions of compound 3 (-λ-), compound 2A (-σ-), A-286982 (-♦-) and sICAM-1 (-τ-) were incubated with either ICAM-1-Ig (A) or compound 2B (B) on plates containing captured LFA-1. The data shown are the average of two plates from a single experiment and are representative of several independent measurements. The solid lines are the fits of the data. The $IC_{50}$ values (nM) are provided in the legends.

Figure 8:
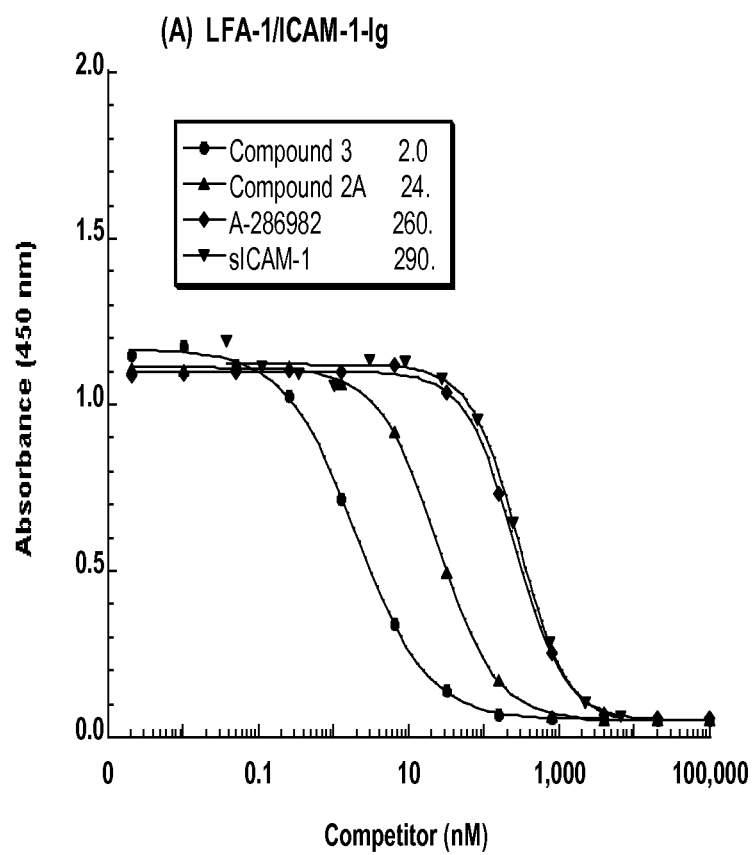
FIG. 8 depicts antagonist competition by compounds 2A, 3, A-286982 and sICAM-1 in the LFA-1/ICAM-1 and LFA-1/small molecule ELISAs.

Typical competition curves for these inhibitors in the ELISA are shown in FIG. 8A. Compound 3 potently inhibited the binding of ICAM-1-Ig to LFA-1 with a 2 nM $IC_{50}$. Compound 2A, an analogue of compound 3, inhibited binding but with an approximately 10-fold higher $IC_{50}$ value. A-286982 and sICAM-1 inhibited ICAM-1-Ig binding to LFA-1 but with $IC_{50}$ values that were more than 100-fold that of compound 3.

The ability of these same compounds to inhibit the binding of a FITC labeled small molecule antagonist, compound 2B, to LFA-1 was also demonstrated (FIG. 8B). The potencies of compounds 2A and 3 and soluble ICAM-1 as inhibitors of compound 2B binding paralleled their potencies as inhibitors of ICAM-1-Ig binding. Compound 3, compound 2A and sICAM-1 inhibited the binding of compound 2B to LFA-1 with $IC_{50}$ values of 3, 56, and 1200 nM, respectively. A-286982 did not inhibit but rather enhanced the binding of compound 2B to LFA-1 as indicated by the transient increase in the absorbance values, reaching a maximal effect at approximately 4 μM before decreasing.

Figure 9:
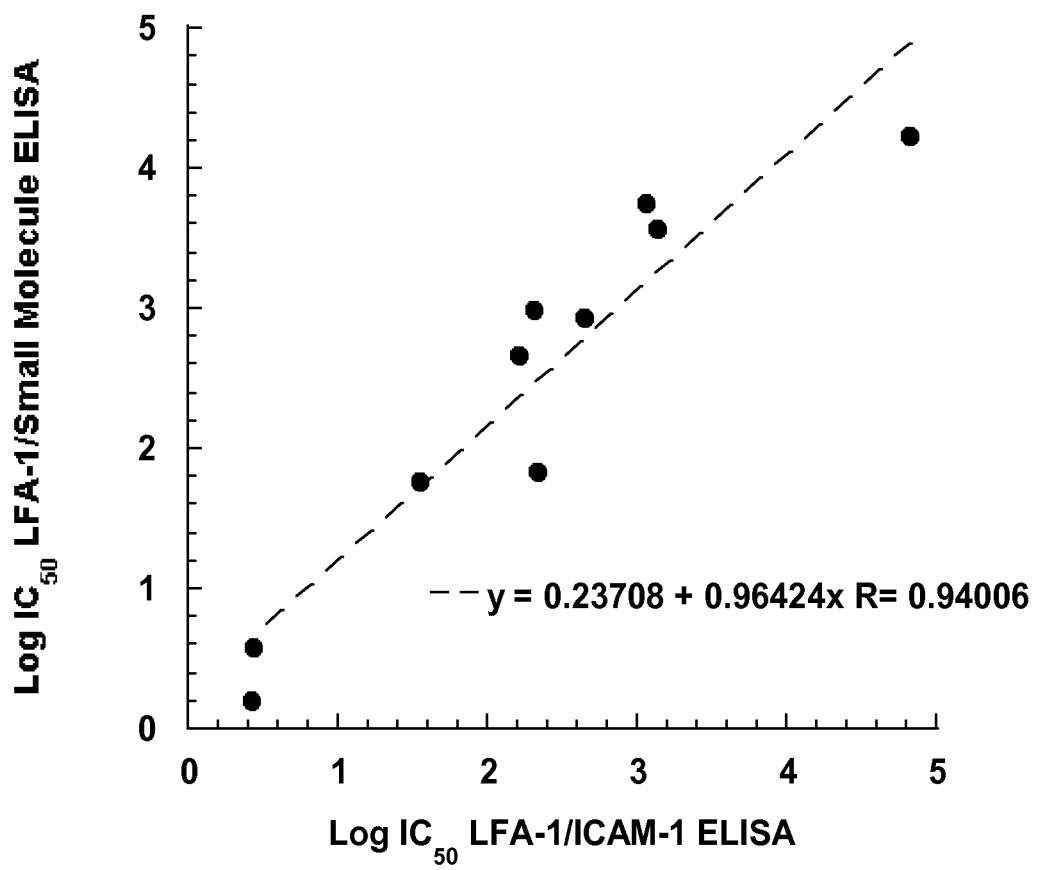
FIG. 9 depicts correlation of IC50 values from antagonist competition in the LFA-1/ICAM-1 and LFA-1/small molecule ELISAs.

The evaluation of $IC_{50}$ values in the LFA-1/small molecule and LFA-1/ICAM-1 ELISAs was extended to a larger set of compounds including a group of kistrin-derived peptides and small molecules representing the evolution of this class of LFA-1 small molecule antagonists (Gadek et al. 2002). As shown in FIG. 9 (Correlation of $IC_{50}$ values from antagonist competition in the LFA-1: ICAM-1 and LFA-1: small molecules ELISAs. The $IC_{50}$ values of a diverse group of compounds (4 peptides, 5 small molecules and sICAM-1) in competition with compound 2B are plotted against the $IC_{50}$ values determined in competition with ICAM-1-Ig for binding to LFA-1. The slope of the plot is 0.964, y-intercept, 0.237 and R=0.940. Each data point is the average of $IC_{50}$ values from two plates), there is a good correlation (R=0.94) between the $IC_{50}$ values for competition in each of the two ligand binding assays for this diverse set of compounds, including sICAM-1, compounds 2A and 3, across five log units of potency. The common trend in potencies between the two antagonist competition ELISAs with ICAM-1-Ig and compound 2B as ligands reveals that each compound disrupts the binding of both ICAM-1 and small molecule ligands in a mechanistically similar fashion. This parallel in potency of inhibition demonstrates that ICAM-1-Ig and compound 2B are binding to the same site on LFA-1 (Wong, A., Hwang, S. M., Johanson, K., Samanen, J., Bennett, D., Landvatter, S. W., Chen, W., Heys, J. R., Ali, F. E., Ku, T. W., Bondinell, W., Nichols, A. J., Powers, D. A., and Stadel, J. M. 1998. Binding of [3H]-SK&F 107260 and [3H]-SB 214857 to purified integrin alphaIIbbeta3: evidence for a common binding site for cyclic arginyl-glycinyl-aspartic acid peptides and nonpeptides, *J. Pharmacol. Exp. Therapeutics,* 285: 228-235).

Figure 10:
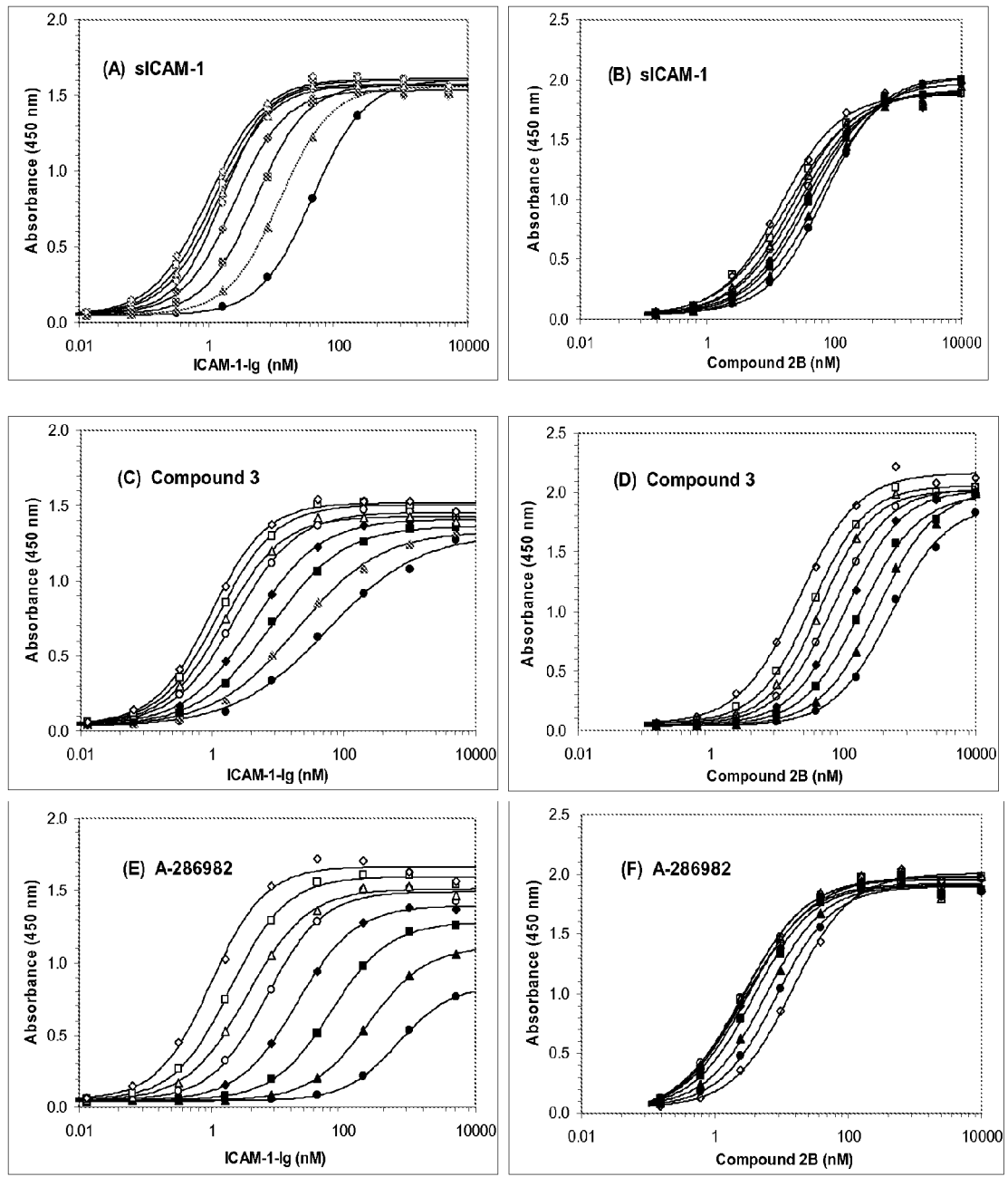
FIG. 10 depicts effect of antagonists on ligand binding in the LFA-1/ICAM-1 and LFA-1/small molecule ELISAs.

2. Antagonist Modulation of Ligand Binding in LFA-1/ICAM-1 and LFA-1/Small Molecule ELISAs An antagonist, which inhibits through direct competition with the ligand of interest, exhibits a non-saturable rightward shift of the ligand binding curves to higher apparent $EC_{50}$ values with increasing antagonist concentration and no reduction in the maximal binding of the ligand (Lutz, M., and Kenakin, T. 1999. *Quantitative Molecular Pharmacology and Informatics in Drug Discovery,* John Wiley & Sons, Ltd., New York, Pratt, W. B., and Taylor, P. 1990. *Principles of Drug Action: The Basis of Pharmacology,* Churchill Livingstone, New York Matthews, J. C. 1993. *Fundamentals of Receptor, Enzyme, and Transport Kinetics*, CRC Press, Boca Raton, Kenakin, T. 1997. *Pharmacologic Analysis of Drug-Receptor Interaction*, Lippincott-Raven, Philadelphia) Inhibition will be surmountable but will require increasing amounts of ligand in the presence of increasing concentrations of a direct competitive inhibitor (Gaddum, J. H., Hameed, K. A., Hathway, D. E., and Stephens, F. F. 1955. Quantitative studies of antagonists for 5-hydroxytryptamine, *Q. J. Exp. Physiol.*, 40: 49-74). The effects of directly competitive compound 3, A-286982 and sICAM-1 on the binding curves of ICAM-1-Ig and compound 2B to LFA-1 are shown in FIG. 10 as examples of antagonists displaying direct competition. Titration of ICAM-1-Ig (A, C, E) or compound 2B (B, D, F) in the absence (-◇-) or presence of antagonist in the LFA-1/ICAM-1 and LFA-1/small molecule ELISAs. The antagonists were added in two-fold dilutions starting at 2.4 (A) and 2.7 (B) μM sICAM-1, 0.040 (C) and 0.10 (D) μM compound 3 and 20 (E) and 50 (F) μM A-286982. The order of antagonist concentrations was, -□- (lowest added antagonist concentration), -Δ-, -μ-, -◆-, -■-, -σ- to -λ- (highest antagonist concentration). The fits of the data are shown as the solid lines. The data shown are from one plate and are representative of a minimum of two experiments. (Note that A-286982 (F) resulted in increased binding of compound 2B to LFA-1.) In contrast, an allosteric inhibitor may alter the ligand binding curves by causing a reduction in maximal binding or saturation in the rightward shifts of the curves (Lutz and Kenakin 1999, Matthews 1993). As shown in FIG. 10A, the presence of increasing concentrations of sICAM-1 clearly shifted the ICAM-1-Ig binding curves rightward to higher $EC_{50}$ values. Additionally, the same maximal extent of binding of ICAM-1-Ig to LFA-1 was observed in the presence and absence of sICAM-1 as expected when two molecular forms of the same natural ligand are competing directly for binding to one site on a receptor (Lutz and Kenakin 1999, Pratt, W. B., and Taylor, P. 1990. *Principles of Drug Action: The Basis of Pharmacology, Churchill Livingstone*, New York, Matthews 1993, Kenakin, T. 1997. *Pharmacologic Analysis of Drug-Receptor Interaction*, Lippincott-Raven, Philadelphia). Similarly, increasing concentrations of compound 3 also shifted the binding of ICAM-1-Ig to higher $EC_{50}$ values with minimal variation in maximal ICAM-1-Ig binding (FIG. 10C). Although the rightward shifts in the ligand binding curves in the presence of a competitive antagonist are typically parallel, this is not always the case (Coultrap, S. J., Sun, H., Tenner, T. E. Jr., and Machu, T. K. 1999. Competitive antagonism of the mouse 5-hydroxytryptamine-3 receptor by bisindolylmaleimide I, a "selective" protein kinase C inhibitor, *Journal of Pharmacology and Experimental Therapeutics*. 290: 76-82). The nonparallel slopes for the LFA-1/ICAM-1-Ig binding curves in the presence and absence of compound 3 may be due to an inability to attain complete equilibrium under the heterogeneous ligand binding ELISA conditions with this compound. In the LFA-1/compound 2B format of the ligand binding ELISA, increasing concentrations of compound 3 also clearly shifted the compound 2B binding curves to higher $EC_{50}$ values with no reduction in maximal binding (FIG. 10D). Increasing concentrations of sICAM-1 also showed a similar effect (FIG. 10B), although the extent of the shift in the curves was limited by the maximum achievable concentration of sICAM-1 at 2.7 μM. Thus, the effects of both sICAM-1 and compound 3 on ICAM-1-Ig and compound 2B binding to LFA-1 are characteristic of direct competition as described above.

The effect of A-286982 on ICAM-1-Ig and compound 2B binding to the receptor was clearly different (FIGS. 10E and 10F). In the LFA-1/ICAM-1 ELISA, the ICAM-1-Ig curves were shifted rightward to higher $EC_{50}$ values; however, the maximum binding of ICAM-1-Ig to LFA-1 decreased considerably with increasing concentrations of A-286982. The reduction in maximal binding and rightward shift of the ligand binding curves with increasing A-286982 concentration are reflective of allosteric inhibition as described above. A-286982 causes reductions in both ligand affinity and binding capacity (Lutz, M., and Kenakin, T. 1999. *Quantitative Molecular Pharmacology and Informatics in Drug Discovery*, John Wiley & Sons, Ltd., New York, Matthews 1993); this demonstrates that A-286982 is an insurmountable antagonist of ICAM-1-Ig binding. In contrast, in the LFA/small molecule ELISA, the presence of A-286982 at micromolar concentrations shifted the compound 2B binding curves to lower $EC_{50}$ values and appeared to enhance the binding of compound 2B to LFA-1 (FIG. 10F). The contrasting effects of A-286982 on compound 2B and ICAM-1-Ig binding may be due to the known allosteric effect of the compound binding to the IDAS site on LFA-1. The A-286982 binding data serve as an illustration for allosteric inhibition for small molecule and protein ligand binding to LFA-1 in the binding experiments demonstrated in this method.

Figure 11:
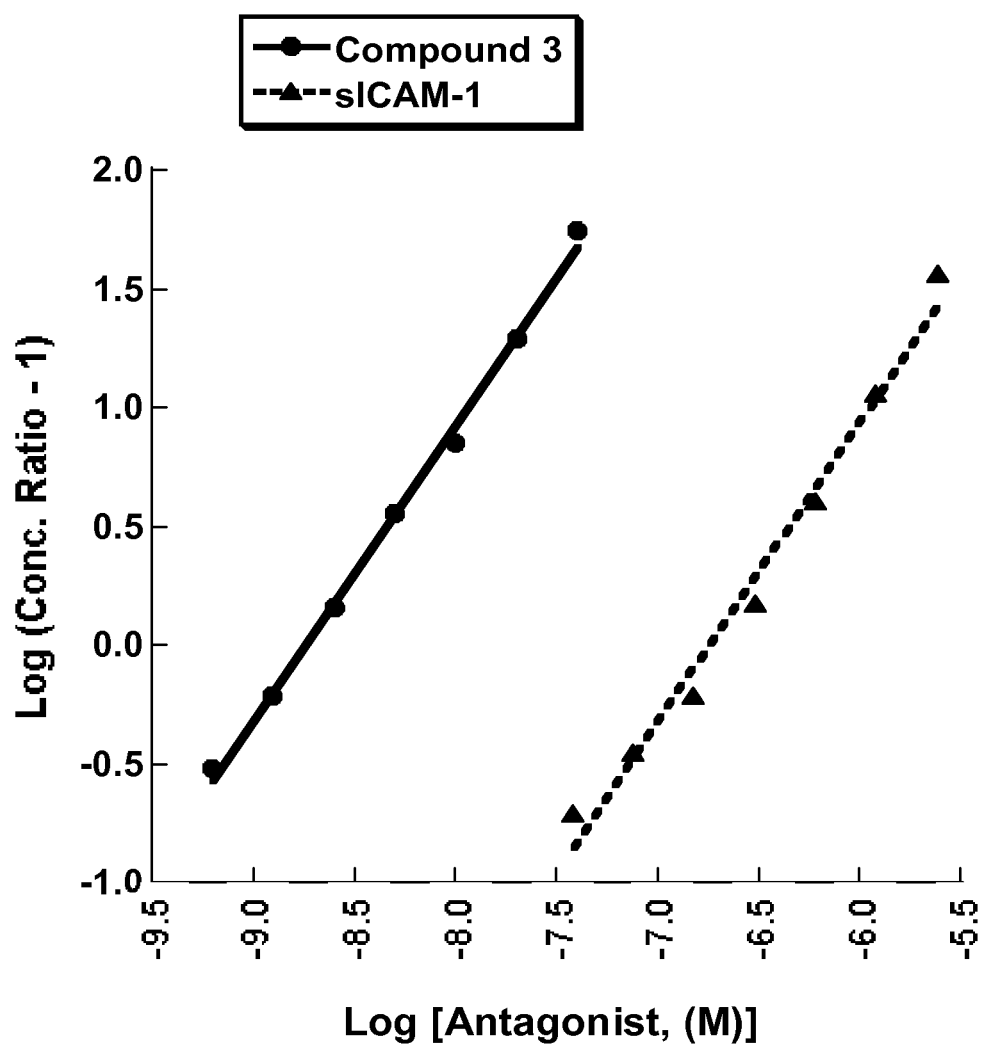
FIG. 11 depicts Schild regressions of sICAM-1 and compound 3 antagonism.

Schild analysis can be also used to investigate whether a compound inhibits ligand binding through direct competition for a single binding site (Lutz and Kenakin 1999, Pratt and Taylor 1990, Matthews 1993, Kenakin 1997, Coultrap 1999). This model is based upon the assumptions that equiactive responses in an assay are the result of equivalent occupancy of receptor by ligand and that maximal binding is unchanged by the presence of antagonist. In a Schild analysis, the dose ratio is the ratio of the $EC_{50}$ values in the presence and absence of antagonist and is a measure of the ligand concentrations leading to equiactive responses. This dose ratio was determined for each concentration of antagonist and the Schild regressions were plotted as shown in FIG. 11. A linear response with a slope of 11n a Schild regression indicates that inhibition by an antagonist is directly competitive and reversible (Lutz and Kenakin 1999, Kenakin 1997). The Schild analysis would yield a nonlinear relationship and/or a slope that deviates significantly from 1 in the case of an allosteric inhibitor that does not result in a reduction of maximal binding (Lutz and Kenakin 1999, Kenakin 1997). The Schild regressions for both sICAM-1 and compound 3 are shown in FIG. 11 with comparable slopes of 1.26 and 1.24, respectively. Schild regressions of s-ICAM-1 (-σ-) and compound 3 (-λ-) antagonism in the LFA-1/ICAM-1 ligand binding ELISA are plotted from the data in FIG. 5(A) and (C), respectively. The slope of the plot for compound 3 is 1.24 with a y-intercept of 10.9 and R=0.99832. The slope of the sICAM-1 plot is 1.26, y-intercept, 8.51 and R=0.99131. Although the Schild analysis requires a linear regression with a slope close to 1 to demonstrate direct competitive inhibition, there is no guidance in the extensive literature as to what range of Schild values are acceptable. Slopes of 1.24 and 1.26 fall within the bounds of many published Schild values used to support competitive binding conclusions, and therefore, these slope values are not considered significantly different than 1. The linearity of the regression plots and the similarity in slopes of the relationships are consistent with binding of ligand (ICAM-1-Ig) and both antagonists (sICAM-1 and compound 3) to the same site in a similar manner.

The binding experiments described above and the analyses discussed are used to form a method for identifying directly competitive inhibitors of LFA-1. Potentially directly competitive therapeutic agents can be investigated using one or more of the experiment types described herein to ascertain whether the agent of interest does compete with known natural and synthetic ligands to compete for binding at the same LFA-1 site at which ICAM-1 binds. The directly competitive antagonist therapeutic agents thus identified are used in the method of the invention to treat a subject in need of treatment for inflammatory disorders mediated by LFA-1 and its interaction with ICAM-1.

VII. Method of Identifying Compounds Useful in Treating Human Disease

A refined searching method is described herein using the pattern of the inhibition of cell growth by siRNA (small interfering RNA sequences) directed against a cellular target involved in cell growth and human disease to identify compounds with a similar pattern of cell growth inhibition in a group of cultured cell lines. The use of siRNA data is desirable because siRNA silences the target's gene and is directly linked to the inhibition of cell growth by that target. Therefore siRNA data is useful to correlate the inhibition of a target's function and the inhibition of cell growth. Compounds identified in this manner are useful in the treatment of human diseases.

Figure 12:
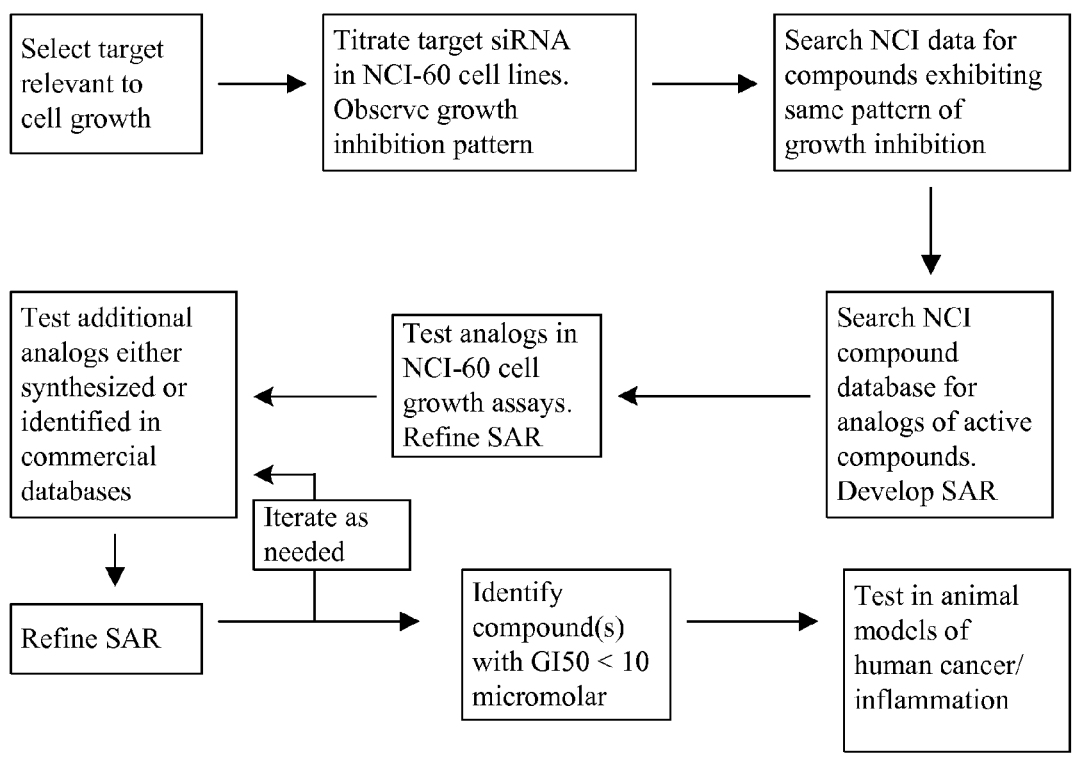
FIG. 12 depicts flow diagram of the discovery of potent inhibitors of cell growth for the treatment of human cancer and inflammation.

FIG. 12 is a flow chart for the identification of compounds for the treatment of human diseases using siRNA growth inhibition data.

The method includes choosing a cellular target (for example, a protein or other biopolymer whose formation is controlled by the transcription and/or translation of a gene) involved in the growth of cells containing said target whose inhibition would be useful in the control of cell growth is selected. This selection can be from lists of such targets in the public domain including the scientific literature and includes enzymes, receptors and proteins involved in protein-protein interactions. One such useful target is the association of beta-catenin with proteins of the TCF family such as TCF-4. These proteins are in the Wnt pathway and are involved in the growth and proliferation of a number of human tumors including common cancer. A compound which binds to beta-catenin and blocks its association with TCF-4 is useful in preventing selected gene transcription and the growth of tumors in human cancers, particularly colon cancer. Small interfering RNA (siRNA) sequences unique to the target are purchased from commercial suppliers such as Dharmacon, Boulder Colo. Cell lines from the National Cancer Institute's panel of 60 cell lines relevant to cancer (for example the Colon and Breast derived NCI cell lines) and/or inflammation (for example the NCI leukemia cell lines) can be grown in the presence of increasing amounts of the siRNA directed against the target until the growth of the cells is inhibited. Alternatively, a single concentration of siRNA can be used against all of the cell lines and the relative inhibition of cell growth can be measured. Cell lines whose growth is dependent on the presence of the target will be inhibited, while other cell lines may be less dependent and consequently their growth will be less inhibited. Thus the inhibition of the panel of the NCI's 60 cell lines will produce a pattern of growth inhibition for each siRNA and target tested. The use of cell lines not currently in the NCI-60 cell line panel are also envisioned as part of this method. It is envisioned additionally that reagents, e.g. Lipofectin™, Lipofectamine™, and the like, can modulate the delivery of siRNA to cells. The NCI's existing data for dose titration effects of compounds on the growth of the same 60 cell lines can be searched using the NCI's COMPARE program or to identify compounds which have a similar pattern of activity (for example, the concentration of compound which inhibits the growth of cells by 50% compared to its uninhibited growth, the GI50 value for a compound). The similarity can be quantified by statistical or other methods including the Pearson correlation used in the NCI COMPARE program. Search algorithms other than NCI COMPARE can be used to define compound and siRNA similarities. Data from the NCI can be analyzed online via the world wide web, or it can be downloaded to a computer or network of computers and analyzed offline. Additional databases including public and proprietary databases linking compound structure to their inhibition of cell growth are also useful for the purposes of this invention. For each target, the structures of compounds whose cell growth activity pattern is similar to the pattern of growth inhibition produced by the siRNA experiment will contain common substructural features (for example phenyl groups, carboxylic acid groups, hydrogen bond donor group, etc.) which can define a structure activity relationship (SAR). Such SAR relationships are commonly used by medicinal chemists skilled in the art of drug discovery to link the activity of compounds against a target to a common structural motif. The development and refinement of an SAR is useful in identifying and designing structurally analogous compounds with a probability or likelihood of showing similar or improved cellular activities. SAR are developed and refined by comparing activities of structurally related compounds. Useful compounds can be synthesized or identified in computer searches of the NCI database or other databases of commercially available compounds or computer generated libraries of compounds with interesting and diverse structural features and computed properties (such as 'druglikeness'). Compounds from commercial or synthetic sources can be tested in the cell growth assays for improved potency in the inhibition of cell growth and the data (both for improvements and declines in potency) can be used to refine the SAR for inhibition of cell growth mediated by a target. Iterative cycles of data acquisition, SAR refinement, compound procurement, compound testing/data acquisition can identify a compound with a potency below 10 micromolar in the inhibition of cell growth. Such a compound can be useful in drug discovery because it is often possible to achieve circulating levels in excess of 10 micromolar in an animal used as a model of human disease (e.g., a mouse xenograft model of human cancer, as a non-limiting example). Further testing in animal models relevant to the target for improved potency, efficacy and duration of action can identify a candidate molecule for the clinical treatment of human diseases including cancer and inflammatory diseases of aberrant cell growth. Alternatively, the identification of compounds which fit an activity pattern opposite of the inhibition of cell growth by siRNA can be stimulants of cell growth useful in diseases and conditions of slow cell growth. Enhanced cell growth could be useful in wound healing and other clinical settings. The method described herein may also utilize the transfection of a gene for a known protein regulator of the target to aid in identifying a pattern of inhibition sufficiently distinctive to be able to identify molecules with a similar pattern of activity.

This method is useful in the identification of potent compounds with significant potencies below 10 micromolar in the inhibition of cell growth. These compounds can be used in animal models of human cancer and inflammation. More preferred are compounds whose inhibition of cell growth (GI50) is below 1 micromolar. Even more preferred are compounds whose growth inhibition (GI50) is less than 100 nM. Most preferred are compounds with GI50 values below 10 nM. The methods of this invention can also be used to identify useful inhibitors of LFA-1, the B-cell receptor BR3, Grb2 (a protein downstream of growth factor receptors in signaling cascades) and other protein targets inside and outside of cells. It is particularly useful against targets in the Wnt pathway including beta-catenin for the treatment of human colon cancer. It is also useful against additional disease related targets in lymphoma, leukemia, colon cancer, melanoma, breast cancer, brain cancer, lung cancer, kidney cancer and other human cancers. The method is useful in identifying compounds useful in the treatment of human inflammatory diseases mediated by the growth and proliferation of inflammatory cells. These include but are not limited to Psoriasis, Eczema, Asthma, rheumatoid arthritis and Dry Eye. Compounds which are identified in the above manner and active in animal models of human disease are useful as treatments of human diseases including cancer and inflammatory diseases. Targets involved in diseases other than cancer and inflammation which involve aberrant cell proliferation can also be used in this method.

Additionally, a method is envisioned to use siRNA cellular activity data for target or selection of targets by searching public and/or proprietary databases of compound cellular activity for a pattern of similar cellular activity in response to a compound or collection of compounds as a method to identify compounds useful in the identification of a human pharmaceutical.

VIII. Examples

A. Materials

Full length recombinant human membrane-bound LFA-1 and recombinant human 5-domain ICAM-1-Ig fusion (ICAM-1-Ig) were produced in human 293 cells and purified as described (Fisher et al. 1997, Keating et al. 2000). sICAM-1 (a truncated form of native ICAM-1 without the transmembrane and cytoplasmic domains for ease of use in in vitro assays, but with the intact LFA-1 binding epitope) and MEM-48 were from R&D Systems (Minneapolis, Minn.). Mouse monoclonal anti-human 132 integrin (clone PLM2) was generated using standard procedures (Fisher et al. 1997). Small molecules and peptide antagonists were synthesized as described (Gadek et al. 2002, Burdick 1999, Liu et al. 2000). Compounds 1-5 and A-286982 are shown in FIG. 4. Compounds 1, 2A and 2B, are similar to compound 3 but with the addition of linkers to enable conjugation to fluorescein (compounds 1 and 2B; 2A was not conjugated to fluorescein). Fluorescein conjugates were prepared via coupling of an amine functionality with fluorescein-5-isothiocyanate (FITC) (Keating et al. 2000). Additional molecules analyzed include compounds 6 and 7 (Gadek et al. 2002), kistrin (Dennis et al. 1990), the non-Kistrin heptapeptides, $H_2N$—C G F D M P C—$CO_2H$ and $H_2N$—C G $Y^{(m)}$D M P C—$CO_2H$, cyclic kistrin peptide C R I P R G D M P D D R C and tetrapeptide, $H_2N$—C $N^{(F)}$ P C—$CO_2H$, wherein $Y^{(m)}$ is meta-tyrosine and $N^{(F)}$ is N'-3-phenylpropyl asparagine.

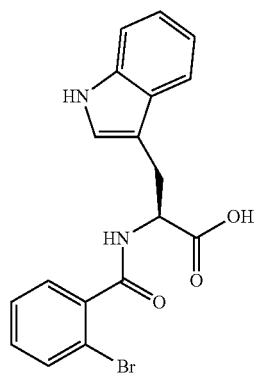

Compound 6

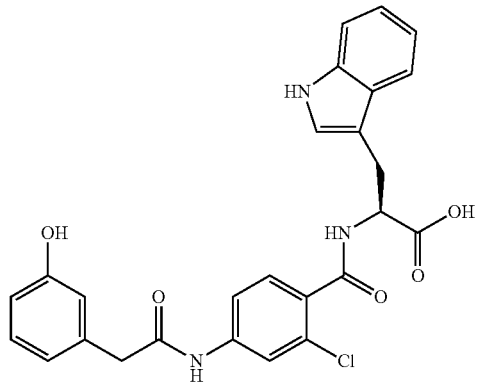

Compound 7

All small molecule antagonists were stored as 10 mM solutions in 50% DMSO at −20° C. Compound 5 was a gift from Hoffman-La Roche Inc. (Nutley, N. J.).

B. Experiments

Example 1

Affinity Measurements

The affinities of the small molecules for LFA-1 were measured using fluorescence polarization (FP) (Lakowicz 1999, Panvera 1995) in a competitive format with a small molecule antagonist, compound 1 (FIG. 2), as previously described (Keating et al. 2000). All measurements were performed in buffer containing 50 mM Hepes, pH 7.2, 150 mM NaCl, 0.05% n-octyglucoside and 0.05% bovine gamma globulins (BGG) and either 1 mM $MnCl_2$, or 1 mM $CaCl_2$ and 1 mM $MgCl_2$. The affinity of compound 1 for LFA-1 was first measured by addition of 2 nM compound 1 to serial dilutions of LFA-1 starting from 1 μM in buffer containing either $MnCl_2$ or $CaCl_2$ and $MgCl_2$. Competition experiments were performed by addition of serial dilutions of antagonists to 2 nM compound 1 (using either 3 nM LFA-1 (in $MnCl_2$) or 40 nM LFA-1 (in $CaCl_2$ and $MgCl_2$)). In the ICAM-1-Ig competition experiments, the LFA-1 concentrations were reduced to 2 and 20 nM LFA-1 in the two divalent cation buffer conditions to maximize inhibition by ICAM-1-Ig. The different LFA-1 concentrations used in the experiments were taken into account in the affinity calculations (see below). The solutions were incubated in 96-well black HE96 plates (Molecular Devices, Sunnyvale, Calif.) for 2 hours at 37° C. Fluorescence Polarization (FP) measurements were performed on an Analyst platereader (Molecular Devices, Sunnyvale, Calif.) using 485 nm excitation, 530 nm emission and 505 nm dichroic filters. All raw intensity data were corrected for background emissions by subtraction of the intensities measured from the appropriate samples without compound 1. The LFA-1 binding and antagonist competition data were analyzed using a non linear least squares fit of a four-parameter equation with KaleidaGraph software (Synergy Software, Reading, Pa.) to obtain the $EC_{50}$ values for the LFA-1 titration and the $IC_{50}$ values of the antagonists. The equation used to fit the data is $Y=((A-D)/(1+(X/C)^B))+D$, where Y is the assay response, A is Y—value at the upper asymptote, B is the slope factor, C is the $IC_{50}$ or $EC_{50}$ and D is Y—the value at the lower asymptote. In general, the data measured in both the homogeneous FP and heterogeneous ELISA formats described below, contain relatively large signal to background ratios and the error estimates in the fits are typically less than 10% of the final value of the fitted parameter. The equilibrium dissociation constants ($K_d$) of LFA-1 for compound 1 with and without A-286982 were calculated using Klotz and Hill analyses (Panvera, 1995). The affinities (K) of the antagonists for LFA-1 were calculated using the $IC_{50}$ values, the $K_d$ of compound 1/LFA-1, and the concentrations of compound 1 and LFA-1 in the competition experiments (Keating et al. 2000, Jacobs et al. 1975).

Example 2

LFA-1/ICAM-1 and LFA-1/Small Molecule Enzyme-Linked Immunosorbent Assays (ELISAs)

(A) Antagonist Competition: Small molecules and sICAM-1 were assayed for the ability to disrupt binding of ICAM-1-Ig or a fluorescein-labeled small molecule antagonist, compound 2B, to LFA-1 in a competitive format (Gadek et al. 2002, Burdick 1999, Quan et al. 1998). Compound 2B is similar to compound 1, but with a longer linker between the small molecule and fluorescein to maximize the binding of the anti-fluorescein detection antibody. 96-well plates were coated with 5 µg/ml (33.3 nM) mouse anti-human 132 integrin (a non-function blocking antibody) in phosphate-buffered saline (PBS) overnight at 4° C. The plates were blocked with assay buffer (20 mM Hepes, pH 7.2, 140 mM NaCl, 1 mM $MnCl_2$, 0.5% bovine serum albumin (BSA) and 0.05% Tween-20) for 1 hour at room temperature. After washing in buffer (50 mM Tris-HCl, pH 7.5, 100 mM NaCl, 1 mM $MnCl_2$, and 0.05% Tween-20), 8 nM LFA-1 (LFA-1/ICAM-1 ELISA) or 2 nM LFA-1 (LFA-1/small molecule ELISA) were added, followed by incubation for 1 h at 37° C. The plates were washed, and for the LFA-1/ICAM-1 ELISA, serial dilutions of the small molecule antagonists or sICAM-1 were added to the plates for 30 minutes, followed by addition of 0.89 nM ICAM-1-Ig (final concentration) for 2 hour at 37° C. After an additional wash, goat anti-huIgG (Fc specific)-HRP was added and incubated for one hour at 37° C. In the LFA-1/small molecule ELISA, the diluted antagonists and 25 nM compound 2B were added concurrently to the plates, followed by a 2-hour incubation at 37° C. Sheep anti-fluorescein-HRP was added after a wash and incubated for one hour at 37° C. For both assays, after washing, the bound HRP-conjugated antibodies were detected by addition of tetramethylbenzidine (TMB) followed by measurement of the absorbance of the product at 450 nm after the addition of 1 M $H_3PO_4$ to stop the reaction. The $IC_{50}$ values for each curve were determined by fitting to the four-parameter equation described above using KaleidaGraph software. The format and results from this form of the LFA-1/ICAM-1 assay are similar to those previously reported (Gadek et al. 2002, Burdick 1999); however, this format is more robust due to antibody capture of the LFA-1 rather than direct coating onto the ELISA plate.

(B) Ligand Binding: The LFA-1/ICAM-1 and LFA-1/small molecule ELISAs were performed as described above except that serial dilutions of either ICAM-1-Ig or compound 2B were added to plates either in the presence or absence of antagonist. In all cases the ligand was added concurrently with the antagonist. The plates were incubated for 6 h at 37° C. to approach equilibrium conditions after antagonist and ligand addition, before wash and addition of the detection antibody. The $EC_{50}$ values for each curve were determined by fitting with a four parameter model as described above. The $EC_{50}$ values generated in the presence and absence of antagonist were analyzed by Schild regression (Arunlakshana and Schild 1959, Lutz and Kenakin 1999, Pratt and Taylor 1990, Matthews 1993, Kenakin, 1997). The Schild plots of Log (Conc. ratio—1) vs. antagonist concentration are calculated from, (Conc. ratio—1)=((ligand $EC_{50}$ with antagonist)/ (ligand $EC_{50}$ without antagonist))-1. The slopes of the plots of the Log(Conc. ratio—1) vs. Antagonist concentration are calculated by fitting the line to the linear equation, $Y=A+BX$.

Example 3

Crosslinking of a Radiolabeled, Photoactivatable Analogue of Compound 3 to LFA-1

Full length human membrane-associated LFA-1 or BSA (0.35 mg/mL [1.4 and 5.3 µM, respectively] in 20 mM Hepes, 150 mM NaCl, 5 mM $CaCl_2$, 5 mM $MgCl_2$, 1 mM $MnCl_2$, and 1% n-octylglucoside, pH 7.2) was incubated overnight at 37° C. with 4.1 µM compound 5, a tritium-labeled photoactivatable analogue of compound 3 (Kauer et al. 1986), in either the presence or absence of 290 µM compound 3. The molar ratio of compound 5 to LFA-1 was 3:1. A 96-well plate precoated with 1% BSA was used for the incubation. Just prior to crosslinking, excess compound 5 was rapidly removed by gel filtration with a G-25 microspin column in a 96-well format equilibrated with the same buffer. The LFA-1/compound 5 complex was crosslinked by exposure to a high-pressure mercury-vapor lamp (450 watts, Ace glass, Vineland, N.J.). During irradiation, samples were cooled on ice and protected by a 5-mm thick plate of borosilicate glass to minimize protein degradation. Residual unlinked compound 5 was removed by gel filtration (G-25) as above. The crosslinked complex was then denatured in 8 M guanidine hydrochloride (GuHCl) and reduced and alkylated. The treated proteins were subjected to SDS-PAGE followed by Coomassie blue staining. Radiolabeled proteins were visualized by audioradiography.

To identify compound 5 binding sites, the treated αL and β2 subunits were separated by size exclusion chromatography in the presence of 6 M GuHCl, 20 mM Hepes, 10 mM EDTA, pH 6.8 and then chemically cleaved with 2.6 M hydroxylamine in 10% acetic acid with 7 M GuHCl for 4 h at 75° C. The radiolabeled protein fragments were separated by SDS-PAGE and either visualized by autoradiography or transferred onto a polyvinylidene fluoride membrane, stained with Coomassie blue, and then identified by N-terminal protein sequencing.

Example 4

Generation of the αL Construct Lacking the I domain

The construct used, pLFA.huID.Δp, contains the sequence of the αL gene from the Nar1 restriction site 5' of the I domain to the second PflM1 restriction site 3' of the I domain in which the first PflM1 restriction site 3' of the I domain was abolished (Edwards et al. 1995). In order to generate the mutant lacking the I domain, the following primers were made: the forward primer CACTGTGGCGCCCTGGTTTTCAGGAAGG-TAGTGGATCAGGCACAAGCAAACAGGAC-CTGACTTC, containing the sequence from the Nar1 site to the start of the I domain, a sequence of DNA encoding GSGSG and the 23 by of the αL sequence after the end of the I domain, and the reverse primer TCTGAGCCATGTGCTG-GTATCGAGGGGC, which primes at the second PflM1 restriction site after the I domain. PCR was performed using these primers and the pLFA.huID.Δp linearized with Bgl II, which cut at a site within the I domain. A DNA fragment was amplified that contained the sequence from the Nar 1 site to the second PflM1 site and in which the entire I domain, from C125 through G311, was replaced with a DNA sequence encoding GSGSG. This piece of DNA was purified, digested with Nar1 and PflM1 and inserted into the human αL plasmid (pRKLFAαm) at the corresponding Nar1 and PflM1 sites. Correct insertion of the DNA sequence encoding GSGSG was confirmed by sequence analysis.

Example 5

Binding of LFA-1 Lacking the I domain to ICAM-1 or Compound 2B 293 cells were transfected with the β2 construct alone (mock) or with either the wild-type αL construct (wt) or the αL construct lacking the I domain (1-less) and allowed to recover for 3 days. The cells were detached and resuspended in adhesion buffer (0.02 M HEPES, pH 7.2, 0.14 M NaCl, 0.2% glucose). Binding to plate bound ICAM-1-Ig was performed as described (Edwards et al. 1998). For binding of compound 2B, $2\times10^5$ cells were added per well in a round bottom 96-well plate in adhesion buffer containing 0.5% BGG, 0.1 mM $MnCl_2$, 1 m/ml anti-β2 activating antibody MEM-48 and 1 μM compound 2B. The cells were incubated for 1 hour at 37° C., washed with cold PBS and fixed with 1% formaldehyde/PBS. The cells were then incubated with a 1:500 dilution of sheep anti-fluorescein-HRP for 1 hour at room temperature, washed with PBS and incubated with TMB for 15 minutes. The reaction was stopped with 1M $H_3PO_4$ and read at 450 nm. In parallel, the transfectants were tested for the structural integrity of the surface-expressed αL/β2 complexes and for the presence or absence of the I domain by FACS analysis using a panel of antibodies with known binding epitopes (Edwards et al. 1998).

Example 6

Human T-Cell Adhesion Assay (Cell Attachment Assay)

The T-cell adhesion assay is performed using a human T-lymphoid cell line HuT 78. Goat anti-HuIgG (Fc) is diluted to 2 mg/ml in PBS and 96-well plates are coated with 50 ml/well at 37° C. for 1 h. Plates are washed with PBS and blocked for 1 h at room temperature with 1% BSA in PBS. 5 domain ICAM-Ig is diluted to 100 ng/ml in PBS and 50 ml/well was added to the plates 0/N at 4° C. HuT 78 cells are centrifuged at 100 g and the cell pellet is treated with 5 mM EDTA for about 5 minutes at 37° C. in a 5% $CO_2$ incubator. Cells are washed in 0.14 M NaCl, 0.02 M Hepes, 0.2% glucose and 0.1 mM $MnCl_2$ (assay buffer) and centrifuged. The cells are resuspended in assay buffer to $3.0\times10^6$ c.ml. Inhibitors are diluted in assay buffer to a 2× final concentration and pre-incubated with HuT78 cells for 30 minutes at room temperature. 100 μl/well of cells and inhibitors are added to the plates and incubated at room temperature for 1 h. 100 μl/well of PBS is added and the plates are sealed and centrifuged inverted at 100 g for 5 minutes. Unattached cells are flicked out of the plate and excess PBS is blotted on a paper towel. 60 μl/well p-nitrophenyl n-acetyl-b-D-glucosaminide (0.257 g to 100 ml citrate buffer) is added to the plate and incubated for 1.5 h at 37° C. The enzyme reaction is stopped with 90 μl/well 50 mM glycione/5 mM EDTA and read on a platereader at 405 nM. HUT 78 cell adhesion to 5dICAM-Ig is measured using the p-nitrophenyl method of Langegren, U. (1984). J. Immunol. Methods 57,379-388.

Example 7

T-Cell Proliferation Assay

This assay is an in vitro model of lymphocyte proliferation resulting from activation, induced by engagement of the T-cell receptor and LFA-1, upon interaction with antigen presenting cells. (Springer, et. al. 1990, Nature) Microtiter plates (Nunc 96 well ELISA certified) are pre-coated overnight at 4° C. with 50 μl of 2 μg/ml of goat anti-human Fc (Caltag H10700) and 50 μl of O. 07 μg/ml monoclonal antibody to CD3 (Immunotech 0178) in sterile PBS.

The next day coat solutions are aspirated. Plates are then washed twice with PBS and 100 μl of 17 ng/ml 5d-ICAM-Ig is added for 4 hours at 37° C. Plates are washed twice with PBS prior to addition of CD4+ T cells. Lymphocytes from peripheral blood are separated from heparinized whole blood drawn from healthy donors. An alternative method is to obtain whole blood from healthy donors through leukophoresis. Blood is diluted 1:1 with saline, layered, and centrifuged at 2500×g for 30 minutes on LSM (6.2 g Ficoll and 9.4 g sodium diztrizoate per 100 ml) (Organon Technica, NJ). Monocytes are depleted using a myeloid cell depletion reagent method (Myeloclear, Labs, Hornby, Ontario, Canada). PBLs are resuspended in 90% heat-inactivated Fetal Bovine serum and 10% DMSO, aliquoted, and stored in liquid nitrogen. After thawing, cells are resuspended in RPMI 1640 medium (Gibco, Grand Island, N.Y.) supplemented with 10% heat-inactivated Fetal Bovine serum (Intergen, Purchase, N.Y.), 1 mM sodium pyruvate, 3 mM L-glutamine, 1 mM nonessential amino acids, 500 μg/ml penicillin, 50 μg/ml streptomycin, 50 μg/ml gentamycin (Gibco).

Purification of CD4+ T cells are obtained by negative selection method (Human CD4 Cell Recovery Column Kit # CL110-5 Accurate). 100,000 purified CD4+ T cells (90% purity) per microtiter plate well are cultured for 72 hours at 37° C. in 5% $CO_2$ in 100 ml of culture medium (RPMI 1640 (Gibco) supplemented with 10% heat inactivated FBS (Intergen), 0.1 mM non-essential amino acids, 1 nM Sodium Pyruvate, 100 units/ml Penicillin, 100 μg/ml Streptomycin, 50 μg/ml Gentamicin, 10 mM Hepes and 2 mM Glutamine). Inhibitors are added to the plate at the initiation of culture. Proliferative responses in these cultures are measured by addition of 1 μCi/well titrated thymidine during the last 6 hours before harvesting of cells. Incorporation of radioactive label is measured by liquid scintillation counting (Packard 96 well harvester and counter). Results are expressed in counts per minute (cpm).

Example 8

In-Vitro Mixed Lymphocyte Culture Model

The mixed lymphocyte culture model, which is an in vitro model of transplantation (A. J. Cunningham, "Understanding Immunology, Transplantation Immunology" pages 157-159 (1978) examines the effects of various LFA-1 antagonists in both the proliferative and effector arms of the human mixed lymphocyte response.

Isolation of Cells: Mononuclear cells from peripheral blood (PBMC) are separated from heparanized whole blood drawn from healthy donors. Blood is diluted 1:1 with saline, layered, and centrifuged at ×2500 g for 30 minutes on LSM (6.2 g Ficoll and 9.4 g sodium diztrizoate per 100 ml) (Organon Technica, NJ). An alternative method is to obtain whole blood from healthy donors through leukophoresis. PBMCs are separated as above, resuspended in 90% heat inactivated Fetal Bovine serum and 10% DMSO, aliquoted and stored in liquid nitrogen. After thawing, cells are resuspended in RPMI 1640 medium (Gibco, Grand Island, N.Y.) supplemented with 10% heat-inactivated Fetal Bovine serum (Intergen, Purchase, N.Y.), 1 mM sodium pyruvate, 3 mM L-glutamine, 1 mM nonessential amino acids, 500 µg/ml penicillin, 50 µg/ml streptomycin, 50 Kg/ml gentamycin (Gibco).

Mixed Lymphocyte Response (MLR): One-way human mixed lymphocyte cultures are established in 96-well flat-bottomed microtiter plates. $1.5 \times 10^5$ responder PBMCs are co-cultured with an equal number of allogeneic irradiated (3000 rads for 3 minutes, 52 seconds stimulator PBMSc in 200 µl of complete medium. LFA-1 antagonists are added at the initiation of cultures.

Cultures are incubated at 37° C. in 5% $CO_2$ for 6 days, then pulsed with of $^3$H-thymidine (6.7 Ci/mmol, NEN, Boston, Mass.) for 6 hours. Cultures are harvested on a Packard cell harvester (Packard, Canberra, Canada). [$^3$H] TdR incorporation is measured by liquid scintillation counting. Results are expressed as counts per minute (cpm).

Example 9

Rabbit Model to Reverse the Onset of Dry Eye

Dry eye is created in rabbits by surgically closing the lacrimal gland excretory duct, and allowing the rabbits to remain untreated for at least four weeks. See Gilbard, J. P, 1996 "Dry Eye: pharmacological approaches, effects, and progress" CLAO J. 22, 141-145. After confirming dry eye by Schirmer test, and ocular surface staining, LFA-1 antagonists of the invention is instilled as a solution at concentrations of 0.01, 0.1, and 1.0% in neutral, isotonic buffered aqueous solution. Administration is one 50 microliter drop to the ocular surface up to 5 times a day, every day for 4 weeks. The symptoms of dry eye are monitored once a week for 4 weeks and an increase in Schirmer scores and/or a decrease in the amount of ocular surface staining indicates the efficacy of the LFA-1 antagonist in the treatment of dry eye disease.

Example 10

Phase 1 Human Study

Up to 56 healthy individuals are enrolled. A randomized, controlled, dose escalation trial of both single and multiple administrations of LFA-1 antagonist is conducted. Cohorts of 7 subjects each (5 treatment, 2 placebo) are treated at each of 6-8 dose levels of LFA-1 antagonists formulated as sterile, neutral, isotonic, buffered aqueous solutions. Subjects receive a single intra-ocular administration on Day 1. Samples are obtained for pharmacokinetic and pharmacodynamic assessments over the subsequent week. Starting Day 8, subjects receive the same dose of LFA-1 antagonist daily for a total of 14 days. PK/PD assessments, safety laboratory studies, Schirmer testing, corneal staining and conjunctival biopsies are assessed.

Example 11

Phase II Human Study 150 adult patients with dry eye as defined by key inclusion/exclusion criteria are enrolled. The patients may or may not have Sjogren's syndrome or Sjogren's disease. A randomized, controlled dose finding trial of LFA-1 antagonists is conducted. Three groups of patients receive either Restasis at the labeled dose, or, one of two dose levels of LFA-1 antagonist, formulated as a neutral, buffered, isotonic aqueous solution, daily for twelve weeks. Patients are followed for safety and for evidence of improvement in Schirmer's test, corneal staining and overall disease severity index for a follow up period of three months. Conjunctival biopsies are obtained in a subset of patients.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical composition comprising an effective amount of a compound having the following formula:

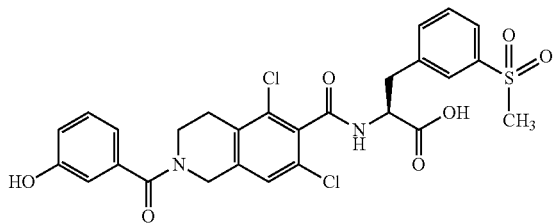 [SMILES: CS(=O)(=O)c1cccc(C[C@H](NC(=O)c2c(Cl)cc3c(c2Cl)CCN(C(=O)c2cccc(O)c2)C3)C(=O)O)c1]

or a pharmaceutically acceptable salt thereof, and a pharmaceutically acceptable vehicle,
wherein the composition is in the form of liquid drops, liquid wash, gel, ointment, liposomes, solution, cream, powder, foam, crystals, spray, aerosol, or liquid suspension.

2. A pharmaceutical composition comprising an effective amount of a compound having the following formula:

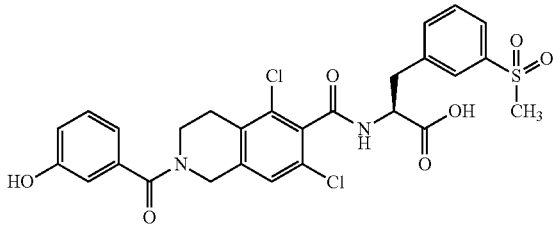 [SMILES: CS(=O)(=O)c1cccc(C[C@H](NC(=O)c2c(Cl)cc3c(c2Cl)CCN(C(=O)c2cccc(O)c2)C3)C(=O)O)c1]

or a pharmaceutically acceptable salt thereof, and a pharmaceutically acceptable vehicle, wherein the pharmaceutically acceptable vehicle is suitable for ocular administration,
wherein the composition is formulated as an insert or implant, subconjunctival injection, intraocular injection, periocular injection, retrobulbar injection, or intracameral injection.

3. The pharmaceutical composition of claim 2 wherein the insert or implant comprises a selective release device comprising a formulation wherein the compound is released in a sustained fashion.

4. The pharmaceutical composition of claim 3 wherein the formulation comprises a biocompatible polymer.

5. The pharmaceutical composition of claim 2, further comprising a preservative.

6. The pharmaceutical composition of claim 1, further comprising a preservative.

7. The pharmaceutical composition of claim 1, wherein the composition is in the form of liquid drops.

8. The pharmaceutical composition of claim 1, wherein the composition is in the form of a liquid wash.

9. The pharmaceutical composition of claim 1, wherein the composition is in the form of a gel.

10. The pharmaceutical composition of claim 1, wherein the composition is in the form of an ointment.

11. The pharmaceutical composition of claim 1, wherein the composition is in the form of liposomes.

12. The pharmaceutical composition of claim 1, wherein the composition is in the form of a solution.

13. The pharmaceutical composition of claim 1, wherein the composition is in the form of a cream.

14. The pharmaceutical composition of claim 1, wherein the composition is in the form of a powder.

15. The pharmaceutical composition of claim 1, wherein the composition is in the form of a foam.

16. The pharmaceutical composition of claim 1, wherein the composition is in the form of crystals.

17. The pharmaceutical composition of claim 1, wherein the composition is in the form of a spray.

18. The pharmaceutical composition of claim 1, wherein the composition is in the form of an aerosol.

19. The pharmaceutical composition of claim 1, wherein the composition is in the form of a liquid suspension.

\* \* \* \* \*

SEQUENCE LISTING

```
<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Asn Leu Asp Val Arg Gly Ala Arg Ser Phe Ser
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
                                        peptide

<400> SEQUENCE: 2

Gly Val Ile Val Gly Ala Pro Gly Glu Gly Asn Ser Thr
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Gly Phe Asp Met Pro Cys
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Meta-Tyr

<400> SEQUENCE: 4

Cys Gly Tyr Asp Met Pro Cys
1               5

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 5

Cys Arg Ile Pro Arg Gly Asp Met Pro Asp Asp Arg Cys
1               5                   10

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N'-3-phenylpropyl Asn

<400> SEQUENCE: 6

Cys Asn Pro Cys
1

<210> SEQ ID NO 7
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 7
cactgtggcg ccctggtttt caggaaggta gtggatcagg cacaagcaaa caggacctga    60
cttc                                                                 64

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Gly Ser Gly
1               5

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tctgagccat gtgctggtat cgaggggc                                       28
```